United States Patent
Yoneyama et al.

(10) Patent No.: US 11,352,438 B2
(45) Date of Patent: Jun. 7, 2022

(54) METHODS OF USING A BISPECIFIC ANTIBODY THAT RECOGNIZES COAGULATION FACTOR IX AND/OR ACTIVATED COAGULATION FACTOR IX AND COAGULATION FACTOR X AND/OR ACTIVATED COAGULATION FACTOR X

(71) Applicants: Chugai Seiyaku Kabushiki Kaisha, Tokyo (JP); F. Hoffmann-La Roche AG, Basel (CH)

(72) Inventors: Koichiro Yoneyama, Tokyo (JP); Christophe Schmitt, Basel (CH)

(73) Assignees: Chugai Seiyaku Kabushiki Kaisha, Tokyo (JP); F. Hoffmann-La Roche AG, Basel (CH)

( * ) Notice: Subject to any disclaimer, the term of this patent is extended or adjusted under 35 U.S.C. 154(b) by 290 days.

(21) Appl. No.: 16/330,269

(22) PCT Filed: Sep. 5, 2017

(86) PCT No.: PCT/JP2017/031933
§ 371 (c)(1),
(2) Date: Mar. 4, 2019

(87) PCT Pub. No.: WO2018/047813
PCT Pub. Date: Mar. 15, 2018

(65) Prior Publication Data
US 2019/0194352 A1 Jun. 27, 2019

Related U.S. Application Data

(60) Provisional application No. 62/485,514, filed on Apr. 14, 2017, provisional application No. 62/437,281, filed on Dec. 21, 2016, provisional application No. 62/383,933, filed on Sep. 6, 2016.

(51) Int. Cl.
C07K 16/36 (2006.01)
A61P 7/04 (2006.01)
A61K 39/00 (2006.01)

(52) U.S. Cl.
CPC .............. *C07K 16/36* (2013.01); *A61P 7/04* (2018.01); *A61K 2039/505* (2013.01); *A61K 2039/54* (2013.01); *A61K 2039/545* (2013.01); *C07K 2317/24* (2013.01); *C07K 2317/31* (2013.01); *C07K 2317/94* (2013.01)

(58) Field of Classification Search
None
See application file for complete search history.

(56) References Cited

U.S. PATENT DOCUMENTS

| | | |
|---|---|---|
| 4,208,479 A | 6/1980 | Maggio et al. |
| 4,444,878 A | 4/1984 | Paulus |
| 4,474,893 A | 10/1984 | Reading |
| 5,496,549 A | 3/1996 | Yamazaki et al. |
| 5,591,828 A | 1/1997 | Bosslet et al. |
| 5,744,446 A | 4/1998 | Lollar et al. |
| 6,005,091 A | 12/1999 | Blackburn et al. |
| 6,010,902 A | 1/2000 | Ledbetter et al. |
| 7,018,632 B2 | 3/2006 | Lindhofer et al. |
| 7,033,590 B1 | 4/2006 | Scheiflinger et al. |
| 7,538,196 B2 | 5/2009 | Jung et al. |
| 7,691,380 B2 | 4/2010 | Thorpe et al. |
| 7,732,149 B2 | 6/2010 | Kojima et al. |
| 8,030,461 B2 | 10/2011 | Kojima |
| 8,062,635 B2 * | 11/2011 | Hattori ................... C07K 16/36 424/136.1 |
| 8,337,841 B2 | 12/2012 | Kojima et al. |
| 8,765,124 B2 | 7/2014 | Saito et al. |
| 9,334,331 B2 * | 5/2016 | Igawa ..................... C07K 16/36 |
| 10,022,319 B2 | 7/2018 | Igawa et al. |
| 10,450,381 B2 | 10/2019 | Igawa et al. |
| 2002/0062010 A1 | 5/2002 | Arathoon et al. |
| 2003/0207346 A1 | 11/2003 | Arathoon et al. |
| 2005/0266425 A1 | 12/2005 | Zauderer et al. |
| 2006/0159653 A1 | 7/2006 | Saito et al. |
| 2007/0041978 A1 | 2/2007 | Hattori et al. |
| 2008/0075712 A1 | 3/2008 | Hattori et al. |
| 2010/0003254 A1 | 1/2010 | Hattori et al. |

(Continued)

FOREIGN PATENT DOCUMENTS

| | | |
|---|---|---|
| CA | 2603264 | 10/2006 |
| CA | 2019559 | 12/2019 |

(Continued)

OTHER PUBLICATIONS

Saenko et al., Vox Sang. Aug. 2002;83(2):89-96.*
Ruggeri et al., Blood. Oct. 1987;70(4):895-904.*
Amersdorfer et al., GenPept Accession No. AAC26541; Aug. 1, 2001.
Asselta et al., "Factor V Deficiency" Semin Thromb Hemost, Jun. 2009, 35(4):382-9.
Bajaj et al., "A Monoclonal Antibody to Factor IX That Inhibits the Factor VIII: Ca Potentiation of Factor X Activation," Journal of Biological Chemistiy, Sep. 25, 1985, 260(21):11574-80.

(Continued)

*Primary Examiner* — Michael Szperka
(74) *Attorney, Agent, or Firm* — Fish & Richardson P.C.

(57) ABSTRACT

An objective of the present invention is to provide an effective pharmaceutical composition or a dosage regimen for preventing and/or treating bleeding, a disease accompanying bleeding, or a disease caused by bleeding. The inventors discovered that by administering a pharmaceutical composition comprising a bispecific antigen-binding molecule that recognizes (a) blood coagulation factor IX and/or activated blood coagulation factor IX and (b) blood coagulation factor X and/or activated blood coagulation factor X according to a given dosage regimen, bleeding, a disease accompanying bleeding, or a disease caused by bleeding can be prevented and/or treated more effectively.

13 Claims, 11 Drawing Sheets
Specification includes a Sequence Listing.

(56) References Cited

U.S. PATENT DOCUMENTS

| | | |
|---|---|---|
| 2012/0237517 A1 | 9/2012 | Hattori et al. |
| 2013/0018174 A1 | 1/2013 | Igawa et al. |
| 2013/0022625 A1 | 1/2013 | Igawa et al. |
| 2013/0330345 A1 | 12/2013 | Igawa et al. |
| 2014/0037632 A1 | 2/2014 | Igawa et al. |
| 2014/0370018 A1 | 12/2014 | Igawa et al. |
| 2016/0222129 A1 | 8/2016 | Igawa et al. |
| 2017/0022293 A1 | 1/2017 | Igawa et al. |
| 2017/0145111 A1 | 5/2017 | Hattori et al. |
| 2017/0253663 A1 | 7/2017 | Yoneyama et al. |
| 2018/0002443 A1 | 1/2018 | Hattori et al. |
| 2018/0244800 A1 | 8/2018 | Hattori et al. |
| 2018/0344630 A1 | 12/2018 | Igawa et al. |
| 2019/0112390 A1 | 4/2019 | Hattori et al. |
| 2019/0309090 A1 | 10/2019 | Yoneyama et al. |
| 2019/0315884 A1 | 10/2019 | Igawa et al. |
| 2019/0359728 A1 | 11/2019 | Hattori et al. |
| 2020/0157243 A1 | 5/2020 | Yoneyama |
| 2020/0277402 A1 | 9/2020 | Hattori et al. |
| 2020/0407463 A1 | 12/2020 | Yoneyama |
| 2021/0107994 A1 | 4/2021 | Shima et al. |
| 2021/0107995 A1 | 4/2021 | Hattori et al. |
| 2021/0189006 A1 | 6/2021 | Saeki et al. |
| 2021/0238307 A1 | 8/2021 | Yoneyama |

FOREIGN PATENT DOCUMENTS

| | | | | |
|---|---|---|---|---|
| CN | 103298937 | 9/2013 | | |
| CN | 105848668 | 8/2016 | | |
| CN | 105859889 | 8/2016 | | |
| EP | 0 369 566 | 5/1990 | | |
| EP | 0 404 097 | 12/1990 | | |
| EP | 0 979 281 | 2/2000 | | |
| EP | 1 220 923 | 7/2002 | | |
| EP | 1 327 681 | 7/2003 | | |
| EP | 1 505 148 | 2/2005 | | |
| EP | 1 605 058 | 12/2005 | | |
| EP | 1 688 488 | 8/2006 | | |
| EP | 1 693 448 | 8/2006 | | |
| EP | 1 876 236 | 1/2008 | | |
| EP | 2 238 985 | 10/2010 | | |
| EP | 1 688 488 B9 | 3/2012 | | |
| EP | 2 238 895 | 8/2012 | | |
| EP | 2 526 963 | 11/2012 | | |
| EP | 2 644 698 | 10/2013 | | |
| EP | 3 159 006 A | 4/2017 | | |
| JP | H02-145187 | 6/1990 | | |
| JP | H05-184383 | 7/1993 | | |
| JP | H05-199894 | 8/1993 | | |
| JP | H05-203652 | 8/1993 | | |
| JP | H05-213775 | 8/1993 | | |
| JP | H05-304992 | 11/1993 | | |
| JP | 06-104071 | 12/1994 | | |
| JP | H08-510555 | 11/1996 | | |
| JP | H10-165184 | 6/1998 | | |
| JP | H10-511085 | 10/1998 | | |
| JP | H11-71288 | 3/1999 | | |
| JP | H11-504007 | 4/1999 | | |
| JP | H11-506310 | 6/1999 | | |
| JP | 3032287 | 4/2000 | | |
| JP | 2001-523971 | 11/2001 | | |
| JP | 2002-518041 | 6/2002 | | |
| JP | 2003-055398 | 2/2003 | | |
| JP | 2003-509049 | 3/2003 | | |
| KR | 2013/0102113 | 9/2013 | | |
| KR | 2013/0102640 | 9/2013 | | |
| KR | 2013/01026402 | 9/2013 | | |
| NO | 20062087 | 7/2006 | | |
| RU | 2339696 | 11/2008 | | |
| RU | 2534347 | 11/2014 | | |
| TW | 2007/14313 | 4/2007 | | |
| TW | 2012/43049 | 11/2012 | | |
| TW | I452135 | 9/2014 | | |
| TW | I452136 | 9/2014 | | |
| TW | 2016/00112 | 1/2016 | | |
| TW | 2016/25299 | 7/2016 | | |
| TW | 2018/22815 | 7/2018 | | |
| WO | WO 91/008770 | 6/1991 | | |
| WO | WO 93/011161 | 6/1993 | | |
| WO | WO 94/013804 | 6/1994 | | |
| WO | WO 95/001571 | 1/1995 | | |
| WO | WO 96/001653 | 1/1996 | | |
| WO | WO 96/007754 | 3/1996 | | |
| WO | WO 96/016673 | 6/1996 | | |
| WO | WO 96/026964 | 9/1996 | | |
| WO | WO 96/33208 | 10/1996 | | |
| WO | WO 98/050431 | 11/1998 | | |
| WO | WO 99/010494 | 3/1999 | | |
| WO | WO 99/067359 | 12/1999 | | |
| WO | WO 01/019992 | 3/2001 | | |
| WO | WO 01/090192 | 11/2001 | | |
| WO | WO 02/006838 | 1/2002 | | |
| WO | WO 02/030463 | 4/2002 | | |
| WO | WO 02/033073 | 4/2002 | | |
| WO | WO 03/035835 | 5/2003 | | |
| WO | WO 03/042231 | 5/2003 | | |
| WO | WO 03/087163 | 10/2003 | | |
| WO | WO 03/091424 | 11/2003 | | |
| WO | WO 2004/009618 | 1/2004 | | |
| WO | WO 2004/060919 | 7/2004 | | |
| WO | WO 2004/065611 | 8/2004 | | |
| WO | WO 2004/097041 | 11/2004 | | |
| WO | WO 2004/111233 | 12/2004 | | |
| WO | WO 2005/025615 | 3/2005 | | |
| WO | WO 2005/035753 | 4/2005 | | |
| WO | WO 2005/035754 | 4/2005 | | |
| WO | WO 2005/035756 | 4/2005 | | |
| WO | WO 2006/106905 | 10/2006 | | |
| WO | WO 2006/109592 | 10/2006 | | |
| WO | WO 2007/114319 | 10/2007 | | |
| WO | WO 2007/114325 | 10/2007 | | |
| WO | WO 2009/041643 | 4/2009 | | |
| WO | WO 2009/084659 | 7/2009 | | |
| WO | WO 2012/067176 | 11/2010 | | |
| WO | WO 2011/090088 | 2/2011 | | |
| WO | WO 2011/078332 | 6/2011 | | |
| WO | WO 2011/157283 | 12/2011 | | |
| WO | WO-2012067176 A1 * | 5/2012 | ............. | C07K 16/36 |
| WO | WO 2013/131866 | 9/2013 | | |
| WO | WO 2015/066700 | 5/2015 | | |
| WO | WO 2015/194233 | 12/2015 | | |
| WO | WO-2015194233 A1 * | 12/2015 | ............. | C07K 16/36 |
| WO | WO 2016/164708 | 10/2016 | | |
| WO | WO 2016/166014 | 10/2016 | | |
| WO | WO 2016/171202 | 10/2016 | | |
| WO | WO 2017/129585 | 8/2017 | | |
| WO | WO 2017/188356 | 11/2017 | | |
| WO | WO 2018/181870 | 10/2018 | | |
| WO | WO 2019/088143 | 5/2019 | | |
| WO | WO 2021/070885 | 4/2021 | | |

OTHER PUBLICATIONS

Bebbington et al., "High-level expression of a recombinant antibody from myeloma cells using a glutamine synthetase gene as an amplifiable selectable marker," Biotechnology (NY), Feb. 1992, 10(2):169-75.

Bessos et al., "The Characterization of a Panel of Monoclonal Antibodies to Human Coagulation Factor IX," Thromb Res, Dec. 15, 1985, 40(6):863-7.

Blazar et al., "Infusion of Anti-B7.1 (CD80) and Anti-B7.2 (CD86) Monoclonal Antibodies Inhibits Murine Graft-Versus-Host Disease Lethality in Part via Direct Effects on CD4+ and CD8+ T Cells," The Journal of Immunology, Oct. 15, 1996, 157(8):3250-9.

Bolton-Maggs et al., "Haemophilias A and B," Lancet, May 24, 2003, 361(9371):1801-9.

Borrebaeck et al., "Antibody Evolution Beyond Nature," Nature Biotechnology, Dec. 2002, 20(12):1189-90.

Bos et al., "Enhanced Transfection of a Bacterial Plasmid into Hybridoma Cells by Electroporation: Application for the Selection of Hybrid Hybridoma (Quadroma) Cell Lines," Hybridoma, Feb. 1992, 11(1):41-51.

(56) References Cited

OTHER PUBLICATIONS

Bowen et al., "Haemophilia A and Haemophilia B: molecular insights," Mol Pathol, Feb. 2002, 55(1):1-18.
Brandstetter et al., "X-ray structure of clotting factor IXa: Active site and module structure related to Xase activity and hemophilia B," Proc Natl Acad Sci USA, Oct. 10, 1995, 92(21):9796-800.
Brennan et al., "Preparation of Bispecific Antibodies by Chemical Recombination of Monoclonal Immunoglobulin G1 Fragments," Science, Jul. 5, 1985, 229(4708):81-3.
Brinkman et al., "Phospholipid-Binding Domain of Factor VIII Is Involved in Endothelial Cell-Mediated Activation of Factor X by Factor IXa," Arterioscler Thromb Vase Biol, Mar. 1, 2002, 22(3):511-6.
Carter, "Bispecific human IgG by design," J Immunol Methods, Feb. 1, 2001, 248(1-2):7-15.
Chugai Seiyaku Kabushiki Kaisha's letter dated Jun. 12, 2013, regarding oral proceedings scheduled on Jun. 26, 2013, in App. Ser. No. EP 06730769.4 (Annex A submitted with patentee's letter dated Jun. 12, 2013).
Dahlback, "Blood Coagulation," Lancet, May 6, 2000, 355(9215):1627-32.
Davie et al., "The Coagulation Cascade: Initiation, Maintenance, and Regulation," Biochemistry, Oct. 29, 1991, 30(43):40363-70.
De Pascalis et al., "Grafting of "Abbreviated" Complementarity-Determining Regions Containing Specificity-Determining Residues Essential for Ligand Contact to Engineer a Less Immunogenic Humanized Monoclonal Antibody," The Journal of Immunology, Sep. 15, 2002, 169(6):3076-84.
Deng et al., "An Agonist Murine Monoclonal Antibody to the Human c-Mpl Receptor Stimulates Megakaryocytopoiesis," Blood, Sep. 15, 1998, 92(6)4981-8.
Ewert et al., "Stability improvements of antibodies for extracellular and intracellular applications: CDR grafting to stable frameworks and structure based framework engineering," Methods, Oct. 2004, 34(2):484-99.
Fay, "Activation of Factor VIII and Mechanisms of Cofactor action," Blood Rev, Mar. 2004, 18(1):4-15.
Fay et al., "Nonenzymatic cofactors: factor VIII," Comprehensive Biochemistry, vol. 13, 1986, pp. 35-37.
Figini et al., "In Vitro Assembly of Repertoires of Antibody Chains on the Surface of Phage by Renaturation," J Mol Biol, May 27, 1994, 239(1):68-78.
Francois et al., "Construction of a Bispecific Antibody Reacting with the α- and β-Chains of the Human IL-2 Receptor," J Immunol, May 15, 1993, 150(10):4610-9.
Gelderman et al., "The Inhibitory Effect of CD46, CD55, and CD59 on Complement Activation After Immunotherapeutic Treatment of Cervical Carcinoma Cells with Monoclonal Antibodies or Bispecific Monoclonal Antibodies," Lab Invest, Apr. 2002, 82(4):483-93.
Gonzales et al., "Minimizing the Immunogenicity of Antibodies for Clinical Application," Tumour Biol, Jan.-Feb. 2005, 26(1):31-43.
Grosse-Hovest et al., "A recombinant bispecific single-chain antibody induces targeted, supra-agonistic CD28-stimulation and tumor cell killing," Eur J Immunol, May 2003, 33(5):1344-40.
Hammerling et al., "Use of Hybrid Antibody with Anti-TG and Anti-Ferritin Specificities in Locating Cell Surface Antigens by Electron Microscopy," J Exp Med, Dec. 1, 1968, 128(6):1461-73.
Helfrich et al., "A rapid and versatile method for harnessing scFv antibody fragments with various biological effector functions," J Immunol Methods, Apr. 3, 2000, 237(1-2):131-45.
Hemlibra (emicizumab-kxwh) Prescribing Information, U.S. Food and Drug Administration, Nov. 2017, 16 pages.
Hoad et al., "Characterisation of Monoclonal antibodies to human factor X/Xa Initial observations with a quantitative ELISA procedure," J Immunol Methods, Feb. 15, 1991, 136(2):269-78.
Holliger et al., "'Diabodies': Small bivalent and bispecific antibody fragments," Proc Natl Acad Sci USA, Jul. 15, 1993, 90(14):6444-8.
Hsia et al., "Treatment of acquired factor X inhibitor by plasma exchange with concomitant intravenous immunoglobulin and corticosteroids," Am J Hematol, Apr. 2008, 83(4):318-20.
Hu et al., "Development and Characterization of a Novel Fusion Protein Composed of a Human IgG1 Heavy Chain Constant Region and a Single-Chain Fragment Variable Antibody against Venezuelan Equine Encephalitis Virus," J Biochem, Jan. 2003, 133(1):59-66.
Huse et al., "Generation of a Large Combinatorial Library of the Immunoglobulin Repertoire in Phage Lambda," Science, Dec. 8, 1989, 246(4935):1275-81.
Igawa et al., "Generation of a Novel Bispecific Antibody (ACE910) Against Activated Factor IX and Factor X Mimicking the Function of Factor VIII Cofactor Activity," Blood, 2012, vol. 120, No. 21, p. 1126.
Iwahashi et al., "CDR substitutions of a humanized monoclonal antibody (CC49): contributions of individual CDRs to antigen binding and immunogenicity," Mol Immunol, Oct.-Nov. 1999, 36(15-16):1079-91.
Janeway et al., "The Immune System in Health and Disease," Immunobiology, 3rd Edition, Garland Press 1997, pp. 3:1-3:11.
Jirholt et al., "Exploiting sequence space: shuffling in vivo formed complementarity determining regions into a master framework," Gene, Jul. 30, 1998, 215(2):471-6.
Kang et al., "Linkage of recognition and replication functions by assembling combinatorial antibody Fab libraries along phage surfaces," Proc Natl Acad Sci USA, May 15, 1991, 88(10):4363-6.
Karpovsky et al., "Production of target-specific effector cells using hetero-cross-linked aggregates containing anti-target cell and anti-Fcγ receptor antibodies," J Exp Med, Dec. 1, 1984, 160(6):1686-701.
Kerschbaumer et al., "An Antibody Specific for Coagulation Factor IX Enhances the Activity of the Intrinsic Factor X-activating Complex," J Biol Chem, Sep. 24, 2004, 279(39):40445-50 Epub Jul. 20, 2004.
Kim et al., "Mammalian type I interferon receptors consists of two subunits: IFNaR1 and IFNaR2," Gene, Sep. 1, 1997, 196(1-2):279-86.
Kitazawa, "Bispecific FIX-FX antibody for bypass therapy" 12th Workshop on Novel Technologies and Gene Transfer for Hemophilia, Oct. 24, 2014.
Kitazawa, "Bispecific FIX-FX antibody for bypass therapy," 12th NHF Workshop on New Technologies and Gene Therapy, Oct. 24, 2014.
Kroesen et al., "Phase I study of intravenously applied bispecific antibody in renal cell cancer patients receiving subcutaneous interleukin 2," Br J Cancer, Oct. 1994, 70(4):652-61.
Kurokawa et al., "Enhanced fibrinolysis by a bispecific monoclonal antibody reactive to fibrin and tissue plasminogen activator," Bio/Technology, Nov. 1989, 7:1163-7.
Lacroix-Desmazes et al, "Dynamics of factor VIII interactions determine its immunologic fate in hemophilia A," Blood, Jul. 15, 2008, 112(2):240-9. doi: 10.1182/blood-2008-02-124941. Epub May 9, 2008.
Lapan et al., "Interaction of the A1 subunit of factor VIIIA and the serine protease domain of factor X identified by zero-length cross-linking," Thromb Haemost, Sep. 1998, 80(3):418-22.
Le Doussal et al., "Bispecific Monoclonal Antibody-Mediated Targeting of an Indium-111-Labeled DTPA Dimer to Primary Colorectal Tumors: Pharmacokinetics, Biodistribution, Scintigraphy and immune Response," J Nucl Med, Oct. 1993, 34(10):1662-71.
Lenting et al., "The Life Cycle of Coagulation Factor VIII in View of its Structure and Function," Blood, Dec. 1, 1998, 92(11):3983-96.
Lindsay, Chapter 4: Determination of the Kinetics and Mechamsm of tg-FIX Activation by Factor XIa, 2004.
Link et al., "Production and Characterization of a Bispecific IgG Capable of Inducing T-Cell-Mediated Lysis of Malignant B Cells," Blood, Jun. 15, 1993, 81(12):3343-9.
Lofqvist et al., "Haemophilia prophylaxis in young patients—a long-term follow-up," J Intern Med, May 1997, 241(5):395-400.
Lu et al., "Fab-scFv fusion protein: an efficient approach to production of bispecific antibody fragments," J Immunol Methods, Sep. 15, 2002, 267(2):213-26.
Lu et al., "Di-diabody: a novel tetravalent bispecific antibody molecule by design," J Immunol Methods, Aug. 2003, 279(1-2):219-32.

(56) References Cited

OTHER PUBLICATIONS

Massino et al., "Quantitative analysis of the products of IgG chain recombination in hybrid hybridomas based on affinity chromatography and radioimmunoassay," J Immunol Methods, Feb. 14, 1997, 201(1):57-66.
McCafferty et al., "Phage antibodies: filamentous phage displaying antibody variable domains," Nature, Dec. 6, 1990, 348(6301):552-4.
Menegatti et al., "Factor X Deficiency," Semin Thromb Hemost, Jun. 2009, 35(4):407-15.
Merchant et al., "An Efficient route to human bispecific IgG," Nat Biotechnol, Jul. 1998, 16(7):677-81.
Mertens et al., "Factor VIII-Factor IX Interactions: Molecular Sites Involved in Enzyme-Cofactor Complex Assembly," Thromb Haemost, Aug. 1999, 82(2):209-17.
Milstein et al., "Hybrid Hybridomas and their use in immunohistochemistry," Nature, Oct. 6-12, 1983, 305(5934):537-40.
Miyazaki et al., "Generation of bispecific IgG, which mimics the cofactor function of blood coagulation factor VIII," Poster Sessions 2P-B-161, 2006.
Morrison, "Two heads are better than one," Nat Biotechnol, Nov. 2007, 25(11):1233-4.
Muto et al., "Hemostatic Effect of a Novel Bispecific Antibody (ACE910) Against Activated Factor IX and Factor X in an Acquired Hemophilia A Model," Blood, 2012, vol. 120, No. 21, p. 42.
Muto et al., "Preventive effect of a bispecific antibody ACE910 that mimics the function of factor VIII on joint bleeding in a model of hemophilia A," Proceedings of The 36th Congress of the Japanese Society on Thrombosis and Hemostasis, May 16, 2014 (with English translation).
Muto et al., "Preventive effect of a bispecific antibody ACE910 that mimics the function of factor VIII on joint bleeding in a model of hemophilia A," Meeting of The 36th Congress of the Japanese Society on Thrombosis and Hemostasis, May 30, 2014 (with English translation).
Muto et al., "Preventive effect of a humanized bispecific antibody to factors IXa and X (ACE910) on spontaneous joint bleeding in a non-human primate model of hemophilia A," Haemophilia, 2014, 20 (Suppl. 3), 76.
Muto et al., "Preventive effect of a humanized bispecific antibody to factors IXa and X (ACE910) on spontaneous joint bleeding in a non-human primate model of hemophilia A," Meeting World Federation of Hemophilia, 2014 World Congress, May 14, 2014.
Muto et al., "Preventive Effect of Bispecific Antibody ACE910 that functionally substitutes for Factor VIII on Intraarticular Bleeding in Hemophilia A Models," Japanese Journal of Thrombosis and Hemostasis, 2014, vol. 25, No. 2:244 (0-016) (with English translation).
"National Haemophilia Foundation (NHF) Medical and Scientific Advisory Council (MASAC) Recommendations Concerning Prophylaxis," Medical Bulletin, 1994, No. 193, 1 page.
(No Authors listed), "Hemophilia and Von Willebrand's Disease: 2. Management," CMAJ, Jul. 15, 1995, 153(2):147-57.
Nilsson et al., "Induction of split tolerance and clinical cure in high-responding hemophiliacs with factor IX antibodies," Proc Natl Acad Sci USA, Dec. 1986, 83(23):9169-73.
Nilsson et al., "Twenty-five years' experience of prophylactic treatment in severe haemophilia A and B," J Intern Med, Jul. 1992, 232(1):25-32.
Nitta et al., "Preliminary trial of specific targeting therapy against malignant glioma," Lancet, Feb. 17, 1990, 335(8686):368-71.
Okubo et al., "The Production and Characterization of Four Monoclonal Antibodies to Human Factor X," J Nara Med Assoc, Jan. 1987, 38(1):20-28.
Panka et al., "Variable region framework differences result in decreased or increased affinity of variant anti-digoxin antibodies," Proc Natl Acad Sci USA, May 1988, 85(9):3080-4.
Paul et al., Fundamental Immunology, 3rd Edition, Raven Press, NY 1993, Chapter 8, p. 242.

Piper et al., "Interferon therapy in primary care," Prim Care Update Ob Gyns, Jul. 2001, 8(4):163-169.
Portolano et al., "Lack of Promiscuity in Autoantigen-Specific H and L Chain Combinations as Revealed by Human H and L chain 'Roulette'," J Immunol, Feb. 1, 1993, 150(3):880-7.
Price et al., "Tissue factor and tissue factor pathway inhibitor," Anaesthesia, May 2004, 59(5):483-92.
Ridgway et al., "Knobs-into-holes" engineering of antibody CH3 domains for heavy chain heterodimerization, Protein Eng, Jul. 1996, 9(7):617-21.
Rudikoff et al., "Single amino acid substitution altering antigen-binding specificity," Proc Natl Sci USA, Mar. 1982, 79(6):1979-83.
Ruef et al., "A Bispecific Antifibrin-antiplatelet Urokinase Conjugate (BAAUC) Induces Enhanced Clot Lysis and Inhibits Platelet Aggregation," Throb Haemost, Jul. 1999, 82(1):109-14.
Ruggeri et al., "von Willebrand Factor and von Willebrand Disease," Blood, Oct. 1987, 70(4): 895-904.
Saenko et al., "Molecular defects in coagulation Factor VIII and their impact on Factor VIII function," Vox Sang, Aug. 2002, 83(2): 89-96.
Saito et al., "Factor VIII Mimetic Antibody: (1) Establishment and Characterization of Anti-factor IX/anti-factor X Bispecific Antibodies," 2005 International Society of Thrombosis and Haemostasis.
Saito et al., "Establishment of Factor VIII Mimetic Antibodies and their IN Vitro Activities in Hemophilia A," 2006 National Hemophilia Foundation Symposia.
Sato et al., "Properties of Two VEGF Receptors, Flt-1 and KDR, in Signal Transduction," Ann NY Acad Sci, May 2000, 902:201-5, discussion 205-7.
Schmidt et al., Human Physiology, Moscow, 1996, v. 2, pp. 431-436 (including what are believed to be corresponding pages from an English language edition of Human Physiology).
Schmidt et al., Human Physiology, Moscow, 1996, v. 3, p. 764 (including what are believed to be corresponding pages from an English language edition of Human Physiology).
Schmidt et al., "Structure-Function Relationships in Factor IX and Factor IXa," Trends Cardiovasc Med Jan. 2003, 13(1):39-45.
Segal et al., "Introduction: bispecific antibodies," J Immunol Methods, Feb. 1, 2001, 248(1-2):1-6.
Shalaby et al., "Development of Humanized Bispecific Antibodies Reactive with Cytotoxic Lymphocytes and Tumor Cells Overexpressing the HER2 Protooncogene," J Exp Med, Jan. 1, 1992, 175(1):217-25.
Shima, "Bispecific antibodies to coagulation factors IXa and X mimic the function of factor VIII," Haemophilia, 2006, 12(suppl.2).
Shima et al., "Factor VIII Mimetic Antibody: (2) In Vitro Assessment of Cofactor Activity in Hemophilia A," Rinsho Ketsueki, Aug. 30, 2005, 46(8):777 (#WS-36-5) (with English translation).
Shima et al., "691 Safety and Prophylactic Efficacy Profiles of ACE910, a Humanized Bispecific Antibody Mimicking the FVIII Cofactor Function in Japanese Hemophilia A Patients Both without and with FVIII Inhibitors: First-in-Patient Phase 1 Study," 56th ASH Annual Meeting and Exposition Abstract & Program [online. Dec. 2014. URL<https://ash.confex.com/ash/2014/webprogram/Paper67797. html>.
Shima et al., "Factor VIII Mimetic Antibody: (2) In Vitro Assessment of Cofactor Activity in Hemophilia A," 2005 International Society of Thrombosis and Hemostasis.
Shima et al., "Pharmacokinetics and Pharmacodynamic Response of Bispecific Antibody ACE910 which Functionally Substitutes for Factor VIII Cofactor, in Healthy Adults," Japanese Journal of Thrombosis and Hemostasis, vol. 25, 2014, No. 2:245 (with English translation).
Shima et al., "Safety and Prophylactic Efficacy Profiles of ACE910, a Humanized Bispecific Antibody Mimicking the FVIII Cofactor Function, in Japanese Hemophilia A Patients Both without and with FVIII Inhibitors: First-in-Patient Phase 1 Study," Blood, 2014, 124:691, https://ash.confex.corn/ash/2014/webprograrn/Paper67797.html. Nov. 6, 2014.
Shima et al., "The pharmacokinetic and pharmacodynamic profiles of ACE910, a bispecific antibody mimicking the FVIII cofactor function, demonstrated in healthy adults," Meeting of The 36th

(56) References Cited

OTHER PUBLICATIONS

Congress of the Japanese Society on Thrombosis and Hemostasis, May 30, 2014 (with English translation).
Shima et al., "The pharmacokinetic and pharmacodynamic profiles of ACE910, a bispecific antibody mimicking the FVIII cofactor function, demonstrated in healthy adults," Proceedings of The 36th Congress of the Japanese Society on Thrombosis and Hemostasis, May 16, 2014 (with English translation).
Shima et al., "The safety, tolerability, pharmacokinetic and pharmacodynamic profiles of ACE910, a humanized bispecific antibody mimicking the FVIII cofactor function demonstrated in healthy adults" Haemophilia, 2014, 20 (Suppl. 3), p. 76.
Shima, "Bi-Specific Antibodies as FVIII Mimetics in Hemophilia" https://www.isth.org/page/2014Microsite/?, https://www.isth.org/page/2014FinalProgram? and http://c.ymcdn.com/sites/www.isth.org/resource/resmgr/Microsite/Milwaukee_Final_Program_6614.pdf, Jun. 10, 2014.
Shima, "Bi-Specific Antibodies as FVIII Mimetics in Hemophilia," ISTH 2014 SSC Final Program, Jun. 10, 2014, p. 56.
Shima, "Bi-Specific Antibodies as FVIII Mimetics in Hemophilia," Meeting of The ISTH 2014 SSCJ, Jun. 25, 2014, 25 pages.
Shima, "New hemophilia treatment by a bispecific antibody to factors IXa and X," The 76th Annual Meeting of the Japanese Society of Hematology, Nov. 1, 2014 (with English translation).
Shima, "New hemophilia treatment by a bispecific antibody to factors IXa and X," Proceedings of The 76th Annual Meeting of the Japanese Society of Hematology, Oct. 23, 2014.
Shima, "New hemophilia treatment by a bispecific antibody to factors IXa and X," http://www2.convention.co jp/76jsh. http://www2.convention.co.jp/76jsh/japanese/schedule.html. https://www.meetingschedule.com/76jsh/schedule.html and https://www.meetingschedule.com/76jsh/abstract.html, Oct. 24, 2014 (with English abstract).
Shima, "New hemophilia treatment by a bispecific antibody to factors IXa and X," The Japanese Journal of Clinical Hematology, 2014, vol. 55, No. 9, p. 236.
Shima, "Novel Bypassing Agents-novel bypass and adjunctive therapies," Meeting of the World Federation of Hemophilia, 2014 World Congress, May 15, 2014.
Shima, "Progress in Pathological Analysis of Hemophilia A," Japanese Journal of Thrombosis and Hemostasis, 2014, vol. 25, No. 2, p. 144 (with English translation).
Shima, "Progress in the Pathological Analysis of Hemophilia A," Proceedings of The 36th Congress of the Japanese Society on Thrombosis and Hemostasis, May 16, 2014 (with English translation).
Shima, "Progress in the Pathological Analysis of Hemophilia A," Meeting of The 36th Congress of the Japanese Society on Thrombosis and Hemostasis, May 31, 2014 (with English translation).
Shima, "The safety, tolerability, pharmacokinetic, and pharmacodynamic profiles of ACE910, a humanized bispecific antibody mimicking the FVIII cofactor function demonstrated in healthy adults," Meeting World Federation of Hemophilia 2014, World Congress, May 14, 2014.
Shima, "How to treat patients with severe haemophilia A without FVIII concentrates? New concepts in haemophilia therapy (bispecific antibody mimicking VIII)," Haemophilia, 2015, 21 (Suppl. 2), pp. 7-8.
Shirahata, "5. Future Prospects. 1) Direction for Improvement of Coagulation Factor Preparations," Iyaku (Medicine and Drug) Journal Co., Ltd., Jan. 15, 2009, 280-9 (with English Translation).
Soeda et al., "Factor VIII Mimetic Antibody: (1) Establishment of Anti-FIXa/FX Bispecific Antibodies," Aug. 30, 2005, 46(8):728 (#PL-2-4) (with English Translation).
Soeda et al., "FVIII-Mimetic Action of Anti-FIXa/Anti-FX Bispecific Antibodies Produced by the Phage Library Method," Jpn J Thromb Hemost, Oct. 1, 2005, 16(5):526 (#0-24) (with English Translation).
Stickney et al., "Bifunctional Antibody: A Binary Radiopharmaceutical Delivery System for Imaging Colorectal Carcinoma," Cancer Res Dec. 15, 1991;51(24):6650-5.
Suresh et al., "Bispecific Monoclonal Antibodies from Hybrid Hybridomas," Methods Enzymol 1986, 121:210-28.
Suresh et al., "Advantages of bispecific hybridomas in one-step immunocytochemistry and immunoassays," Proc Natl Acad Sci USA, Oct. 1986, 83(20):7989-93.
Taki, The Journal of Japanese Society on Thrombosis and Hemostasis, Feb. 2, 2002;13(1):109-13 (with concise English explanation).
Tamura et al., "Structural Correlates of an Anticarcinoma Antibody: Identification of Specificity-Determining Residues (SDRs) and Development of a Minimally Immunogenic Antibody Variant by Retention of SDRs Only," J Immunol, Feb. 1, 2000, 164(3):1432-41.
Uchida et al., "First-In-Human Trial of Bispecific Antibody ACE910 Having Factor VIII-Substituting Activity, Safety, Pharmacokinetics, and Pharmacodynamics in Healthy Adults," Jpn. J. Clin. Pharmacol. Ther., 2014, 45 Suppl:S297.
Vaughan et al., "Human Antibodies with Sub-nanomolar Affinities: Isolation from a Large Non-immunized Phage Display Library," Nat Biotechnol, Mar. 1996, 14(3):309-14.
Weiner et al., "A Human Tumor Xenograft Model of Therapy with a Bispecific Monoclonal Antibody Targeting c-erbB-2 and CD161," Cancer Res, Jan. 1, 1993, 53(1):94-100.
Weiner et al., "The Role of T Cell Activation in Anti-CD3 X Antitumor Bispecific Antibody Therapy," J Immunol, Mar. 1, 1994, 152(5):2385-92.
Xiang et al., "Production of Murine V-Human Cr1 Chimeric Antitag Antibody using V Region cDNA Amplified by PCR," Mol Immunol, Aug. 1990, 27(8):809-17.
Yoneyama et al., "A Pharmacometric Approach to Substitute for a Conventional Dose-Finding Study in Rare Diseases: Example of Phase III Dose Selection for Emicizumab in Hemophilia A," Clin. Pharmacokinet., 2018, 57:1123-1134.
Zhu et al., "An efficient route to the production of an IgG-like bispecific antibody," Protein Eng, May 2000, 13(5):361-7.
U.S. Appl. No. 16/226,798, Hattori et al., filed Dec. 20, 2018.
U.S. Appl. No. 15/132,996, Igawa et al., filed Apr. 19, 2016.
U.S. Appl. No. 15/288,965, Igawa et al., filed Oct. 7, 2016.
U.S. Appl. No. 16/093,495, Saeki et al., filed Oct. 12, 2019.
U.S. Appl. No. 15/319,016, Yoneyama, filed Dec. 15, 2016.
U.S. Appl. No. 14/921,590, filed Oct. 23, 2015, Hattori et al.
U.S. Appl. No. 15/172,727, filed Jun. 3, 2016, Hattori et al.
U.S. Appl. No. 16/093,495, filed Oct. 12, 2018, Saeki et al.
U.S. Appl. No. 16/226,798, filed Dec. 20, 2018, Hattori et al.
Fay et al., "The size of human factor VIII heterodimers and the effects produced by thrombin," Biochim Biophys Acta, Jun. 23, 1986, 871(3):268-78.
Hoyer, "The Factor VIII Complex: Structure and Function," Blood, Jul. 1981, 58(1):1-13.
Kitazawa et al., "A bispecific antibody to factors IXa and X restores factor VIII hemostatic activity in a hemophilia A model," Nat Med, Oct. 2012, 18(10):1570-4. doi: 10.1038/nm.2942. Epub Sep. 30, 2012.
Kitazawa et al., "Factor VIIIa-mimetic cofactor activity of a bispecific antibody to factors IX/IXa and X/Xa, emicizumab, depends on its ability to bridge the antigens," Thromb Haemost, Jun. 28, 2017, 117(7):1348-1357, doi: 10.1160/TH17-01-0030. Epub Apr. 28, 2017.
Muto et al., "Anti-factor IXa/X bispecific antibody (ACE910): hemostatic potency against ongoing bleeds in a hemophilia A model and the possibility of routine supplementation," J Thromb Haemost, Feb. 2014, 12(2):206-13. doi: 10.1111/jth.12474.
Muto et al., "Anti-factor IXa/X bispecific antibody ACE910 prevents joint bleeds in a long-term primate model of acquired hemophilia A," Blood, Nov. 13, 2014, 124(20):3165-71. doi: 10.1182/blood-2014-07-585737. Epub Oct. 1, 2014.
Oldenburg et al., "Emicizumab Prophylaxis in Hemophilia A with Inhibitors," The New England Journal of Medicine, Aug. 2017, 377(9):809-818. doi: 10.1056/NEJMoa1703068. Epub Jul. 10, 2017.
Sampei et al., "Identification and Multidimensional Optimization of an Asymmetric Bispecific IgG Antibody Mimicking the Function of Factor VIII Cofactor Activity," PloS One, Feb. 2013, 8(2):e57479. doi:10.1371/journal.pone.0057479. Epub Feb. 28, 2013.
Shima et al., "Long-term safety and efficacy of emicizumab in a phase 1/2 study in patients with hemophilia A with or without

(56) References Cited

OTHER PUBLICATIONS inhibitors," Blood Adv, Sep. 27, 2017, 1(22):1891-1899. doi: 10.1182/bloodadvances.2017006684. eCollection Oct. 10, 2017.
Shima et al., "Long-term safety and prophylactic efficacy of once-weekly subcutaneous administration of ACE910, in Japanese hemophilia A patients with and without FVIII inhibitors: interim results of the extension study of a phase 1 study," J Thromb Haemost, Jun. 2015, 13 Suppl 2:6-7 (Abstr AS017).
Shima et al., "Factor VIII-Mimetic Function of Humanized Bispecific Antibody in Hemophilia A," The New England Journal of Medicine, May 2016, 374(21):2044-2053. doi: 10.1056/NEJMoa1511769.
Uchida et al., "A first-in-human phase 1 study of ACE910, a novel factor VIII-mimetic bispecific antibody, in healthy subjects," Blood, Mar. 2016, 127(13):1633-1641. doi: 10.1182/blood-2015-06-650226, Epub Dec. 1, 2015.
Vehar et al., "Structure of human factor VIII," Nature, Nov. 22-28, 1984, 312(5992):337-42.
Wood et al., "Expression of active human factor VIII from recombinant DNA clones," Nature, Nov. 22-28, 1984, 312(5992):330-7.
Yoneyama et al., "Repeated Time-to-Event Modeling to Characterize the Bleeding-Prophylactic Efficacy of ACE910, a Bispecific Antibody to Factors IXA and X, in Patients with Hemophilia," Clin Pharmacol Ther, 2016, 99(Suppl 1):S33.
Young et al., "Efficacy, Safety and Pharmacokinetics (PK) of Once-weekly Prophylactic (Px) Emicizumab (ACE910) in Pediatric (< 12 years) Persons with Hemophilia A with Inhibitors (PwHAwI): Interim Analysis of Single-arm, Multicenter, Open-label, Phase 3 Study (HAVEN 2)," Res Pract Thromb Haemost, 2017, 1(Suppl 2):5.
International Search Report and Written Opinion for App. Ser. No. PCT/JP2017/031933, dated Nov. 28, 2017, 9 pages.
U.S. Appl. No. 16/825,513, Hattori et al., filed Mar. 20, 2020.
U.S. Appl. No. 14/019,117, Igawa et al., filed Sep. 5, 2013.
U.S. Appl. No. 16/459,791, Igawa et al., filed Jul. 2, 2019.
U.S. Appl. No. 16/780,977, Yoneyama, filed Feb. 4, 2020.
U.S. Appl. No. 16/780,977, filed Feb. 4, 2020, Yoneyama.
U.S. Appl. No. 16/825,513, filed Mar. 20, 2020, Hattori et al..
ALPROLIX Intravenous, 2019, 16 pages (with English translation).
Astermark et al., "A randomized comparison of bypassing agents in hemophilia complicated by an inhibitor: the FEIBA NovoSeven Comparative (FENOC) Study," Blood, Jan. 15, 2007, 109(2):546-51. Epub Sep. 21, 2006.
Collins et al., "Implications of coagulation factor VIII and IX pharmaco-kinetics in the prophylactic treatment of haemophilia," Haemophilia, Jan. 2011, 17(1):2-10. doi: 10.1111/j.1365-2516.2010.02370.x. Epub Aug. 22, 2010.
Coppola et al., "Acquired Inhibitors of Coagulation Factors: Part I—Acquired Hemophilia A," Semin Thromb Hemost, Jul. 2012, 38(5):433-46. doi: 10.1055/s-0032-1315757. Epub Jun. 27, 2012.
Franchini et al., "Acquired haemophilia A: A 2013 update," Thromb Haemost, Dec. 2013, 110(6):1114-20. doi:10.1160/TH13-05-0363. Epub Sep. 5, 2013.
Guidelines for the Management of Hemophilia, 2005, World Federation of Hemophilia, 52 pages.
Hagiwara et al., "Effect of Emicizumab in improving coagulation ability in the presence of minor amount of Factor IX," Japanese Journal of Thrombosis and Hemostasis, 2017, 28(2):1900-012 (with English translation).
"Hemostatic Therapy Guideline for Inhibitor-negative Hemophilia Patients," Japanese Journal of Thrombosis and Hemostasis, 2013, 24(6):619-639 (with English translation).
"Hemostatic Therapy Guideline for Inhibitor-positive Hemophilia Patients," Japanese Journal of Thrombosis and Hemostasis, 2013, 24(6):640-658 (with English translation).
Kruse-Jarres, "Inhibitors: our greatest challenge. Can we minimize the incidence?," Haemophilia, Jan. 2013, 19(Suppl 1):2-7, doi: 10.1111/hae. 12049.
Lillicrap, "von Willebrand disease: advances in pathogenetic understanding, diagnosis, and therapy," Blood, Nov. 28, 2013, 122(23):3735-40. doi: 10.1182/blood-2013-06-498303. Epub Sep. 24, 2013.

Minami et al., "Bispecific Antibody ACE910 Improves Coagulation Function in Plasma of Patients withFactor XI Deficiency," Japanese Journal of Thrombosis and Hemostasis, 2015, 26(2):188 0-024 (with English translation).
Miyata, "Factor IX Abnormality—Molecular defects of Factor IX," Japanese Journal of Thrombosis and Hemostasis, 1991, 2(1):1-11 (with English translation).
Nishimura et al., "Factor IX Fukuoka. Substitution of ASN$^{92}$ by His in the second epidermal growth factor-like domain results in defective interaction with factors VIIIa/X," Journal of Biological Chemistiy, Nov. 15, 1993, 268(32):24041-24046.
Nogami, "Bispecific Antibody that Substitutes for Factor VIII in the Treatment of Childhood Hemophilia A," The Japanese Journal of Pediatric Hematology/Oncology, 2016, 53(2):69-74 (with English translation).
Shima, "The Forefront and Prospects of Hemophilia Treatment," J Jpn Pediatr Soc, Mar. 1, 2017, 121(3):543-552 (with English translation).
Tarantino et al., "Safety of human plasma-derived clotting factor products and their role in haemostasis in patients with haemophilia: meeting report," Haemophilia, Sep. 2007, 13(5):663-9.
U.S. Appl. No. 16/536,385, Hattori et al., filed Aug. 9, 2019.
U.S. Appl. No. 16/432,790, Yoneyama, filed Jun. 5, 2019.
U.S. Appl. No. 16/536,385, filed Aug. 9, 2019, Hattori et al.
U.S. Appl. No. 16/432,790, filed Jun. 5, 2019, Yoneyama et al.
U.S. Appl. No. 16/459,791, filed Jul. 2, 2019, Igawa et al.
Davie, "A Brief Historical Review of the Waterfall/Cascade of Blood Coagulation," J Biol Chem, Dec. 19, 2003, 278(51):50819-32, Epub Oct. 21, 2003.
Schmidt et al., Chapter 18, Section 18.6, "Hemostasis and Coagulation," Human Physiology, Second, Completely Revised Edition, Springer-Verlag, 1989, pp. 418-423.
Schmidt et al., Chapter 29, "Enzymes of the pancreatic juice," Human Physiology, Second, Completely Revised Edition, Springer-Verlag, 1989, p. 716.
U.S. Appl. No. 15/701,630, Hattori et al., filed Sep. 12, 2017.
U.S. Appl. No. 17/130,736, Hattori et al., filed Dec. 22, 2020.
U.S. Appl. No. 17/017,971, Yoneyama, filed Sep. 11, 2020.
U.S. Appl. No. 17/130,736, filed Dec. 22, 2020, Hattori et al.
Murray et al., Chapter 55 "Blood plasma and coagulation process," Human Biochemistry (Biokhimia tsheloveka), Moscow, Mir Binton, 2009, 2:328-329 (in Russian, with English translation).
Taylor et al., "A new era for hemophilia B treatment," Blood, Apr. 7, 2016, 127(14):1734-1736.
U.S. Appl. No. 16/25,513, Hattori et al., filed Mar. 20, 2020.
U.S. Appl. No. 17/017,971, filed Sep. 11, 2020, Yoneyama.
Mahlangu et al., "Emicizumab Prophylaxis in Patients Who Have Hemophilia A without Inhibitors," N Engl J Med, Aug. 30, 2018, 379(9):811-822.
Shima, "New hemophilia treatment by a bispecific antibody to factors IXa and X," http://www2.convention.co.jp/76jsh, http://www2.convention.co.jp/76jsh/japanese/schedule.html, https://www.meeting-schedule.eom/jsh76/schedule.html and https://www.meetingschedule.com/jsh76/abstract.html, Oct. 24, 2014, 11 pages (with English abstract).
U.S. Appl. No. 16/496,089, filed Sep. 20, 2019, Shima et al.
U.S. Appl. No. 10/575,905, Hattori et al., filed Apr. 30, 2007 (abandoned).
U.S. Pat. No. 8,062,635, Hattori et al., issued Nov. 22, 2011.
U.S. Appl. No. 11/910,836, Hattori et al., filed Jan. 12, 2009 (abandoned).
U.S. Appl. No. 13/434,643, Hattori et al., filed Mar. 29, 2012 (abandoned).
U.S. Appl. No. 14/921,590, Hattori et al., filed Oct. 23, 2015 (abandoned).
U.S. Appl. No. 15/172,727, Hattori et al., filed Jun. 3, 2016 (abandoned).
U.S. Appl. No. 15/402,580, Hattori et al., filed Jan. 10, 2017 (abandoned).
U.S. Appl. No. 15/701,630, Hattori et al., filed Sep. 12, 2017 (abandoned).
U.S. Appl. No. 15/963,345, Hattori et al., filed Apr. 26, 2018 (abandoned).

(56) References Cited

OTHER PUBLICATIONS

U.S. Appl. No. 16/226,798, Hattori et al., filed Dec. 20, 2018 (abandoned).
U.S. Appl. No. 16/536,385, Hattori et al., filed Aug. 9, 2019 (abandoned).
U.S. Appl. No. 16/825,513, Hattori et al., filed Mar. 20, 2020 (abandoned).
U.S. Appl. No. 17/130,736, Hattori et al., filed Dec. 22, 2020 (abandoned).
U.S. Appl. No. 17/389,534, Hattori et al., filed Jul. 30, 2021.
U.S. Pat. No. 9,334,331, Igawa et al., issued May 10, 2016.
U.S. Appl. No. 14/019,117, Igawa et al., filed Sep. 5, 2013 (abandoned).
U.S. Appl. No. 14/019,712, Igawa et al., filed Sep. 6, 2013 (abandoned).
U.S. Pat. No. 10,450,381, Igawa et al., issued Oct. 22, 2019.
U.S. Appl. No. 15/288,965, Igawa et al., filed Oct. 7, 2016 (abandoned).
U.S. Appl. No. 16/459,791, Igawa et al., filed Jul. 2, 2019 (abandoned).
U.S. Appl. No. 17/485,818, Igawa et al., filed Sep. 27, 2021.
U.S. Appl. No. 16/093,495, Saeki et al., filed Oct. 12, 2018.
U.S. Appl. No. 15/319,016, Yoneyama, filed Dec. 15, 2016 (abandoned).
U.S. Appl. No. 16/432,790, Yoneyama, filed Jun. 5, 2019 (abandoned).
U.S. Appl. No. 16/780,977, Yoneyama, filed Feb. 4, 2020 (abandoned).
U.S. Appl. No. 17/017,971, Yoneyama, filed Sep. 11, 2020 (abandoned).
U.S. Appl. No. 17/235,445, Yoneyama, filed Apr. 20, 2021.
U.S. Appl. No. 16/496,089, Shima et al., filed Sep. 20, 2019.
U.S. Appl. No. 16/758,128, Hosoguchi et al., filed Apr. 22, 2020.
U.S. Appl. No. 16/061,429, filed Jun. 12, 2018, Igawa et al.
U.S. Appl. No. 16/758,128, filed Apr. 22, 2020, Hosoguchi et al.
U.S. Appl. No. 17/235,445, filed Apr. 20, 2021, Yoneyama.
U.S. Appl. No. 17/389,534, filed Jul. 30, 2021, Hattori et al.
U.S. Appl. No. 17/485,818, filed Sep. 27, 2021, Igawa et al.
Al-Banaa et al., "Emicizumab Use in Treatment of Acquired Hemophilia A: A Case Report," Am J Case Rep, Jul. 18, 2019, 20:1046-1048.
Dane et al., "Successful use of emicizumab in patient with refractory acquired hemophilia A and acute coronary syndrome requiring percutaneous coronary intervention," Res Pract Thromb Haemost, Apr. 9, 2019, 3(3):420-423.

Glatter, "Evaluation of Small-Angle Scattering Data from Lamellar and Cylindrical Particles by the Indirect Transformation Method," J Appl Ciyst, 1980, 13:577-584.
Knoebl et al., "Emicizumab for the treatment of acquired hemophilia A," Blood, Jan. 21, 2021, 137(3):410-419. First Edition: Aug. 7, 2020.
Mohnle et al., "Emicizumab in the Treatment of Acquired Haemophilia: A Case Report," Transfus Med Hemother, Apr. 2019, 46(2):121-123.
Retout et al., "Population Pharmacokinetic Analysis and Exploratory Exposure-Bleeding Rate Relationship of Emicizumab in Adult and Pediatric Persons with Hemophilia A," Clin Pharmacokinet, Dec. 2020, 59(12):1611-1625. Published online Jun. 5, 2020.
Sakai et al., "Guidelines for the management of acquired hemophilia: A: 2017 revision," Jpn J Thromb Hemost, 28(6):715-747 (with English translation).
Supplementary Appendix, 2016, to Shima et al., "Factor VIII—Mimetic Function of Humanized Bispecific Antibody in Hemophilia A," The New England Journal of Medicine, May 2016, 374(21):2044-2053. doi: 10.1056/NEJMoa1511769, which was cited in the IDS filed on Apr. 8, 2019.
Supplemental Data, 2017, to Shima et al., "Long-term safety and efficacy of emicizumab in a phase 1/2 study in hemophilia A patients with or without inhibitors," Blood Adv, Sep. 27, 2017, 1(22):1891-1899. doi: 10.1182/bloodadvances.2017006684. eCollection Oct. 10, 2017, which was cited in the IDS filed on Apr. 8, 2019.
Takeyama et al., "An anti-factor IXa/factor X bispecific antibody, emicizumab, improves ex vivo coagulant potentials in plasma from patients with acquired hemophilia A," J Thromb Haemost, Apr. 2020, 18(4):825-833.
Tian et al., "In-depth analysis of subclass-specific conformational preferences of IgG antibodies," IUCrJ, Jan. 1, 2015, 2(Pt 1):9-18. doi: 10.1107/S205225251402209X. eCollection Jan. 1, 2015.
Yada et al., "Spotlight on emicizumab in the management of hemophilia A: patient selection and special considerations," J Blood Med, Jul. 2, 2019, 10:171-181.
USPTO Restriction Requirement in U.S. Appl. No. 10/575,193, dated Mar. 24, 2009, 7 pages.
USPTO Non-Final Office Action in U.S. Appl. No. 10/575,193, dated Sep. 24, 2009, 22 pages.
USPTO Final Office Action in U.S. Appl. No. 10/575,193, dated Jun. 23, 2010, 17 pages.
USPTO Restriction Requirement in U.S. Appl. No. 16/099,341, dated Apr. 17, 2020, 8 pages.

* cited by examiner

[Fig. 1]
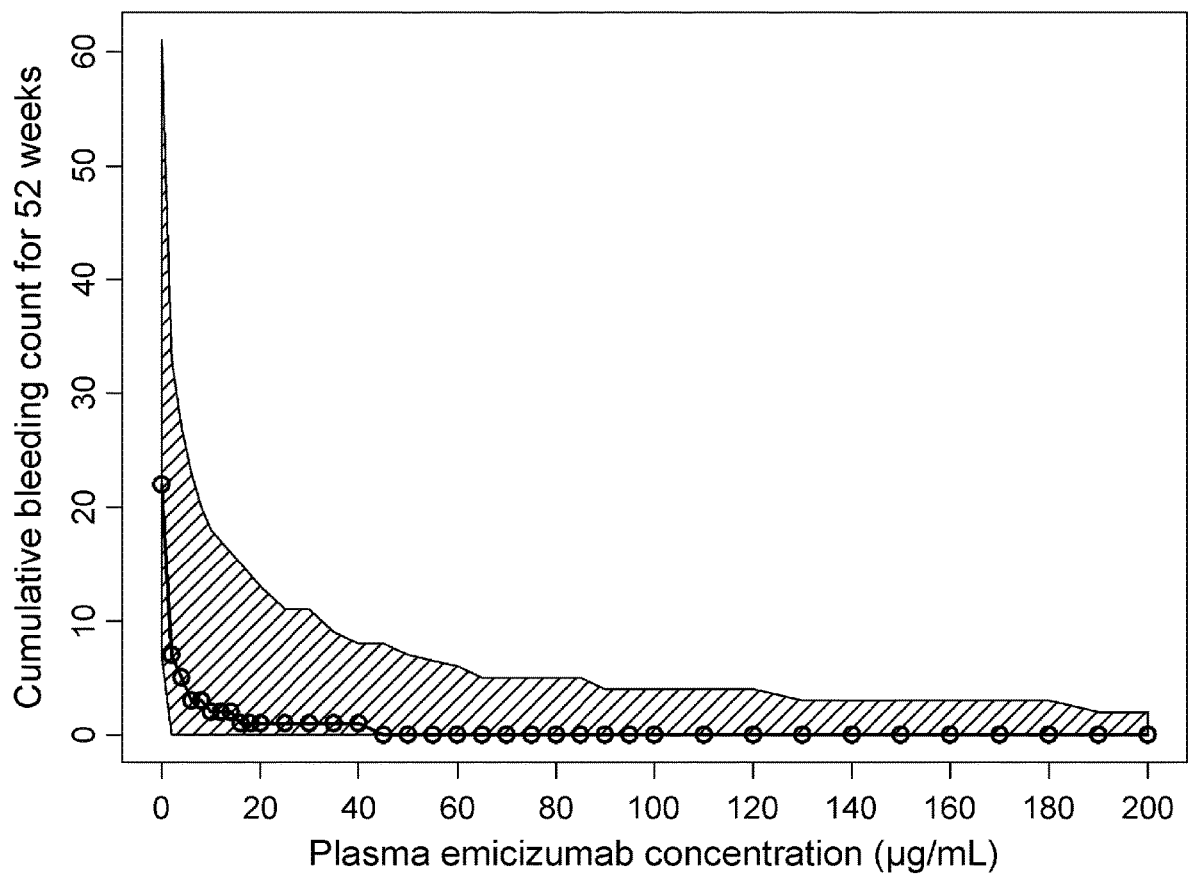

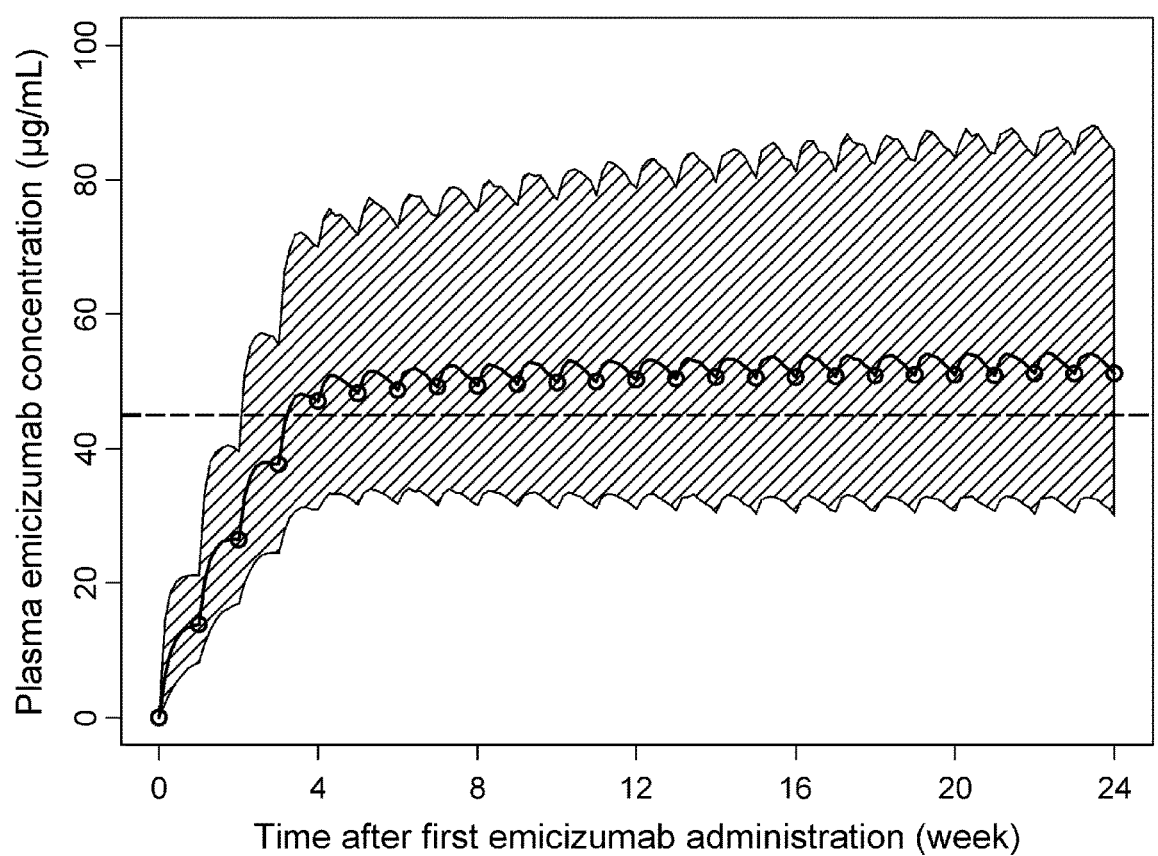
[Fig. 2]
3 mg/kg once weekly for first 4 weeks followed by 1.5 mg/kg once weekly

[Fig. 3]
3 mg/kg once weekly for first 4 weeks followed by 3 mg/kg once every two weeks
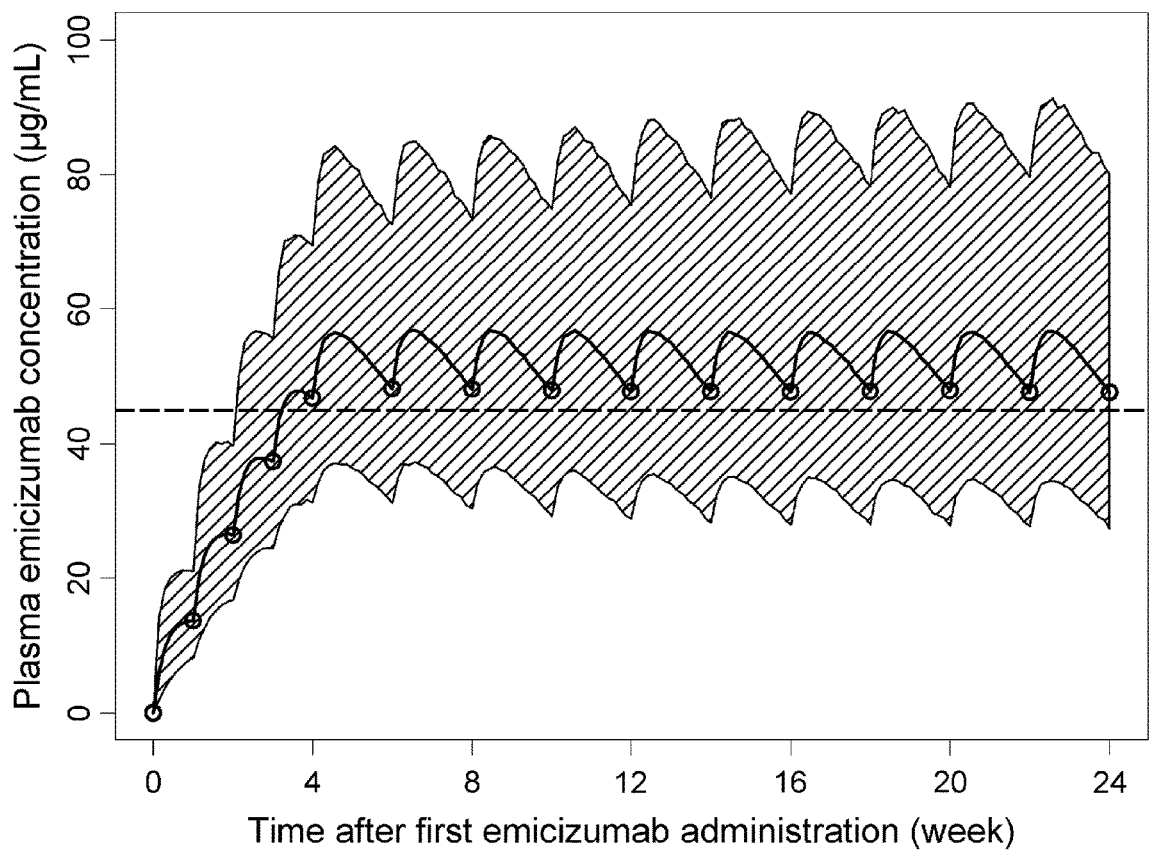

[Fig. 4]
3mg/kg once weekly for first 4 weeks followed by 6 mg/kg once every four weeks
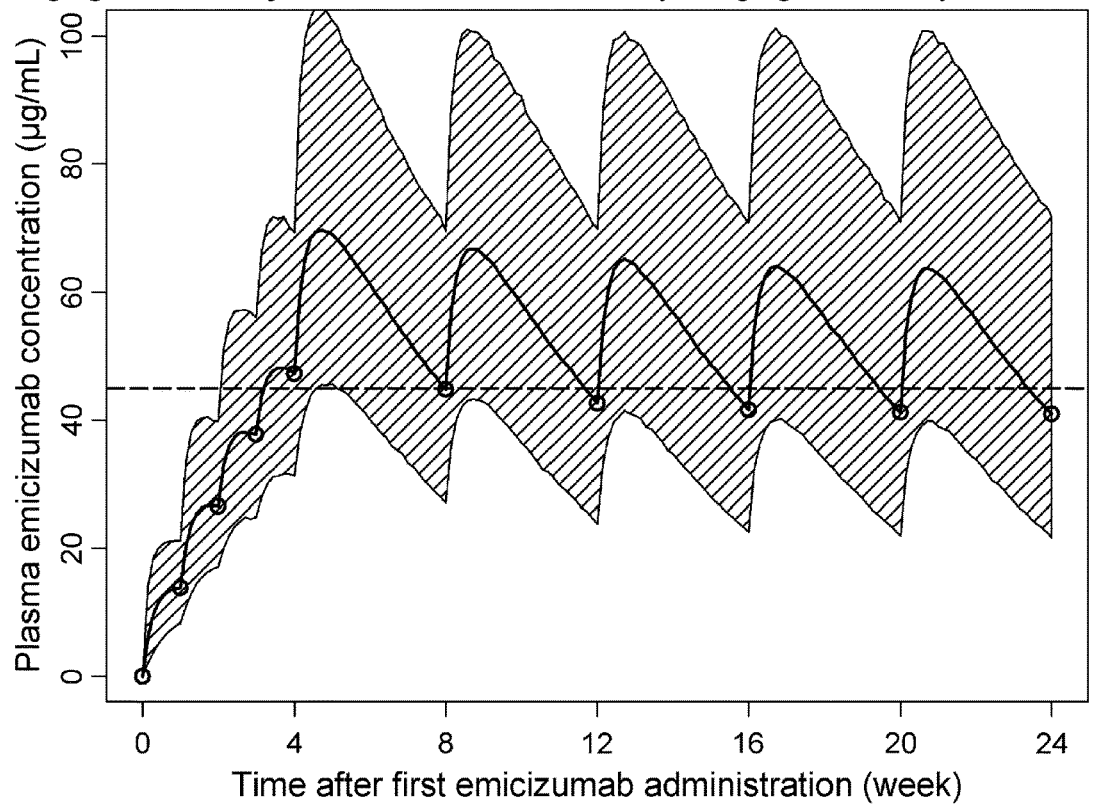
[Fig. 5]
3 mg/kg once weekly for first 4 weeks followed by 1.5 mg/kg once weekly
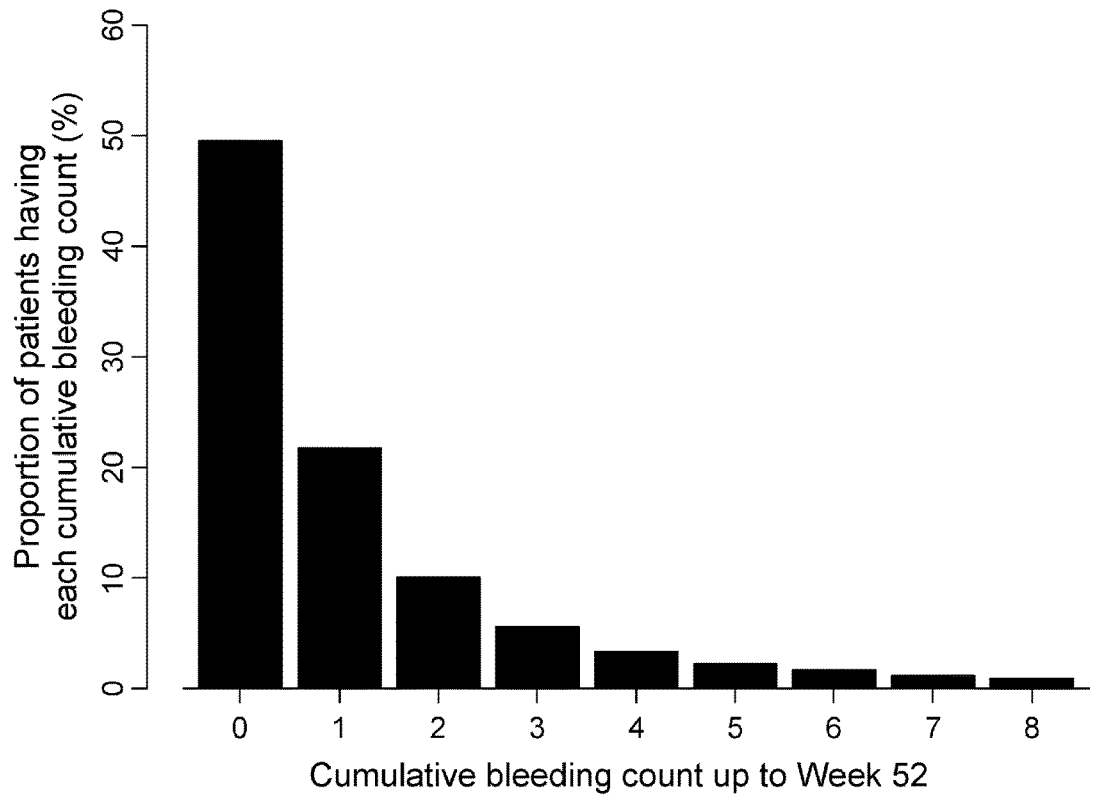

[Fig. 6]
3mg/kg once weekly for first 4 weeks followed by 3 mg/kg once every two weeks
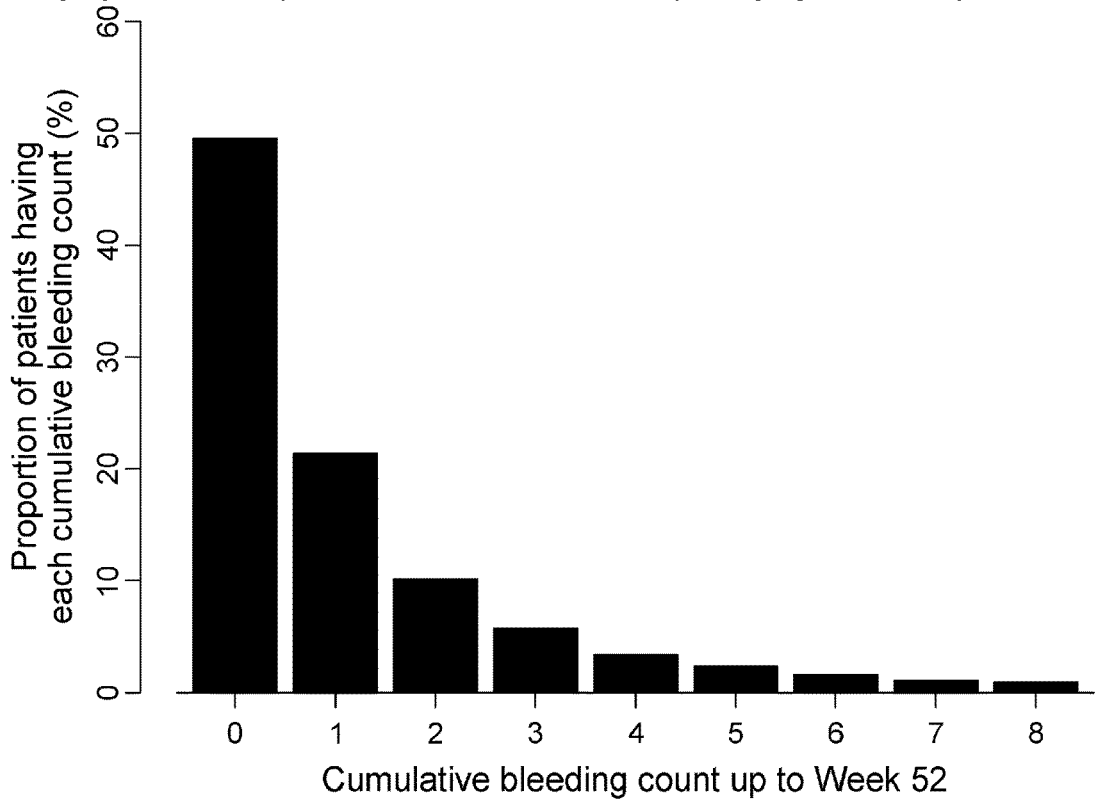
[Fig. 7]
3mg/kg once weekly for first 4 weeks followed by 6 mg/kg once every four weeks
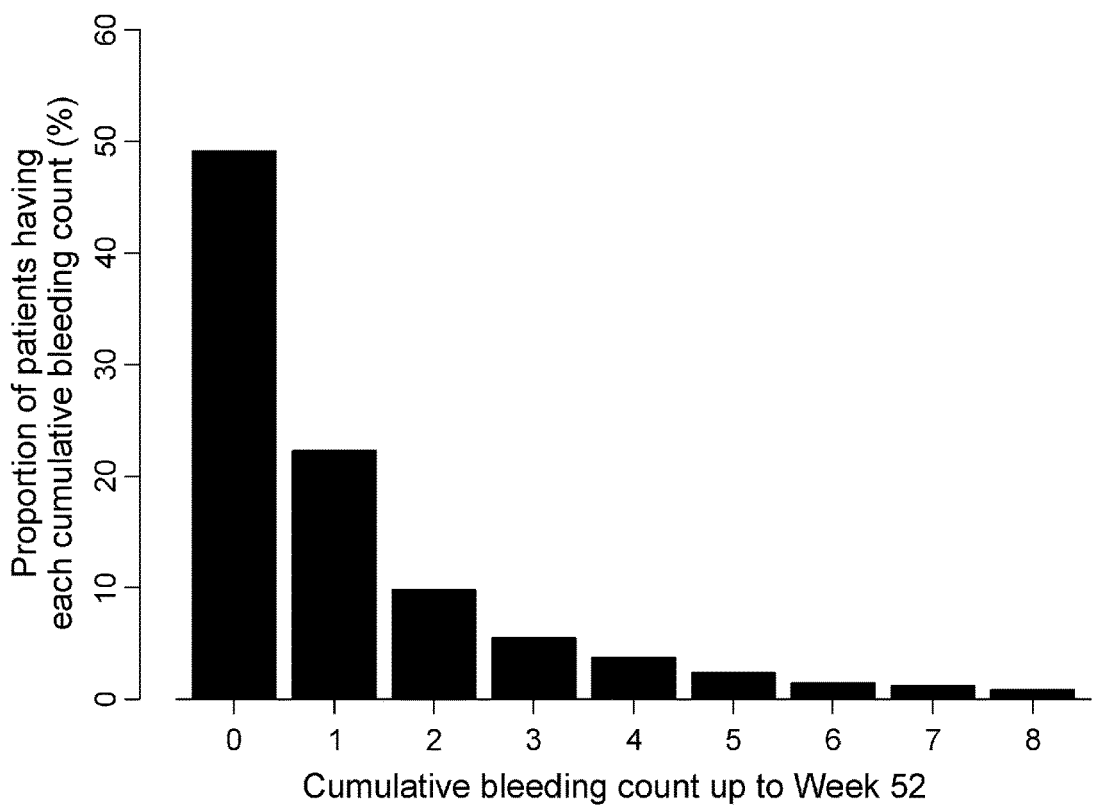

[Fig. 8]
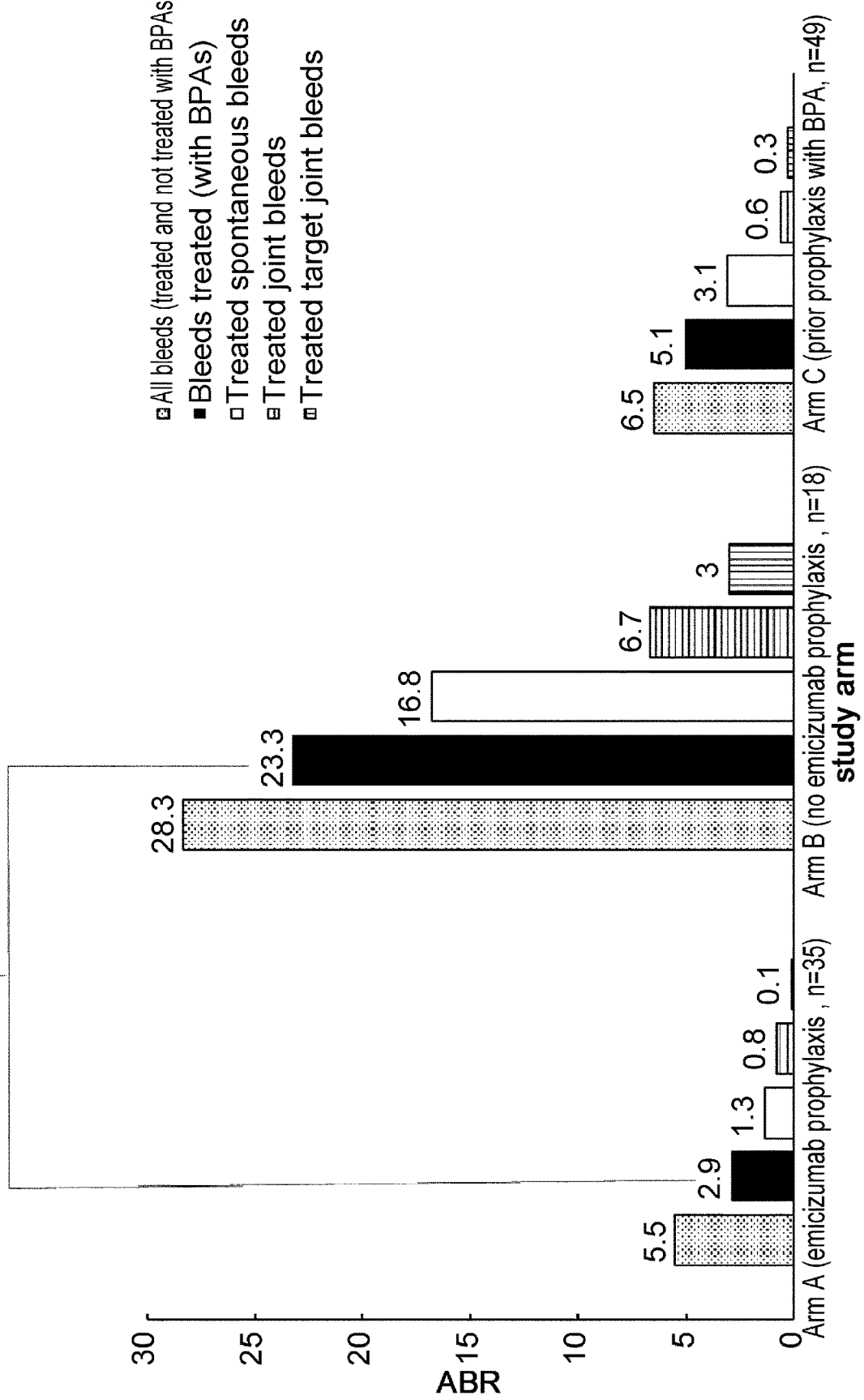

[Fig. 9]
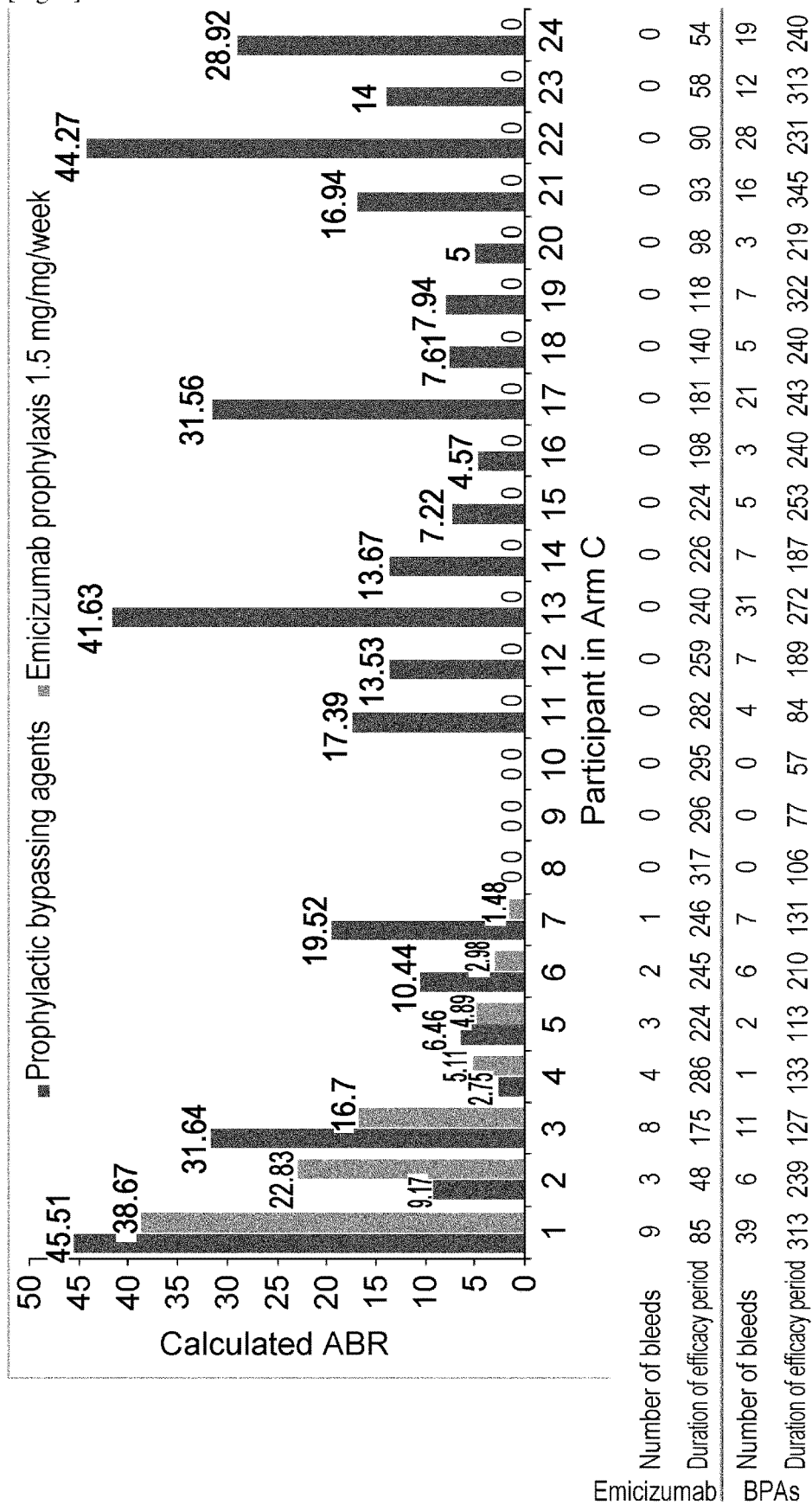

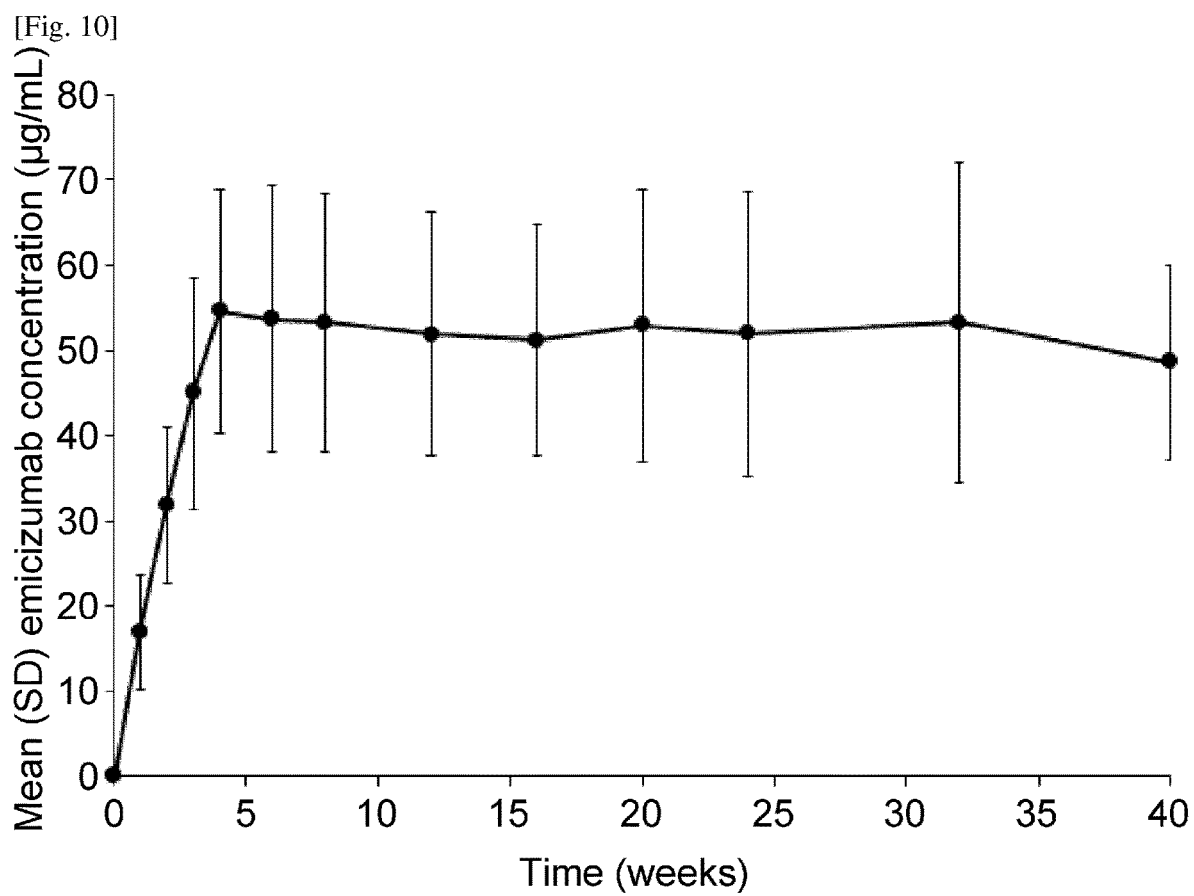
[Fig. 10]

[Fig. 11]
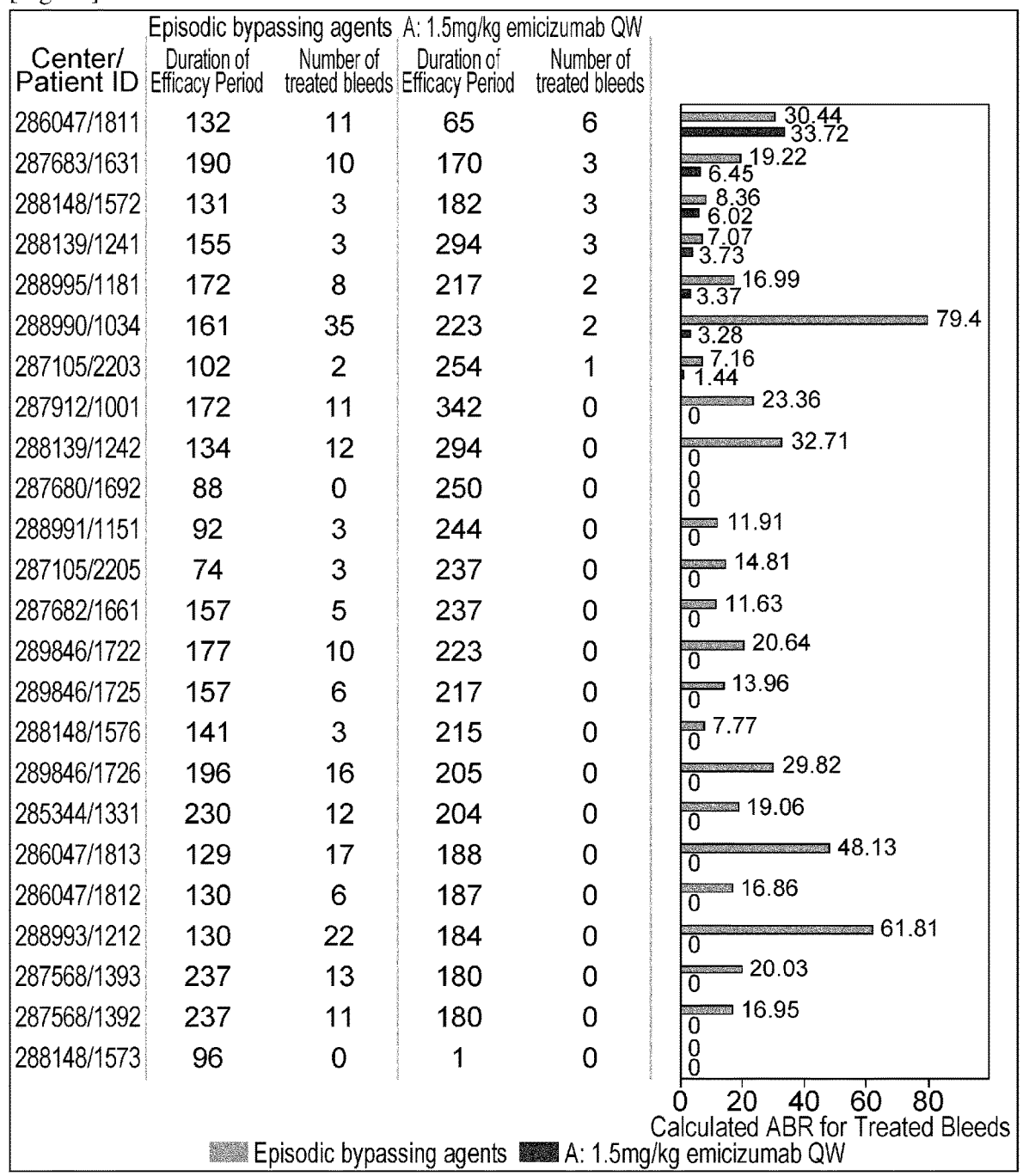
| Center/Patient ID | Episodic bypassing agents | | A: 1.5mg/kg emicizumab QW | |
|---|---|---|---|---|
| | Duration of Efficacy Period | Number of treated bleeds | Duration of Efficacy Period | Number of treated bleeds |
| 286047/1811 | 132 | 11 | 65 | 6 |
| 287683/1631 | 190 | 10 | 170 | 3 |
| 288148/1572 | 131 | 3 | 182 | 3 |
| 288139/1241 | 155 | 3 | 294 | 3 |
| 288995/1181 | 172 | 8 | 217 | 2 |
| 288990/1034 | 161 | 35 | 223 | 2 |
| 287105/2203 | 102 | 2 | 254 | 1 |
| 287912/1001 | 172 | 11 | 342 | 0 |
| 288139/1242 | 134 | 12 | 294 | 0 |
| 287680/1692 | 88 | 0 | 250 | 0 |
| 288991/1151 | 92 | 3 | 244 | 0 |
| 287105/2205 | 74 | 3 | 237 | 0 |
| 287682/1661 | 157 | 5 | 237 | 0 |
| 289846/1722 | 177 | 10 | 223 | 0 |
| 289846/1725 | 157 | 6 | 217 | 0 |
| 288148/1576 | 141 | 3 | 215 | 0 |
| 289846/1726 | 196 | 16 | 205 | 0 |
| 285344/1331 | 230 | 12 | 204 | 0 |
| 286047/1813 | 129 | 17 | 188 | 0 |
| 286047/1812 | 130 | 6 | 187 | 0 |
| 288993/1212 | 130 | 22 | 184 | 0 |
| 287568/1393 | 237 | 13 | 180 | 0 |
| 287568/1392 | 237 | 11 | 180 | 0 |
| 288148/1573 | 96 | 0 | 1 | 0 |

[Fig. 12]
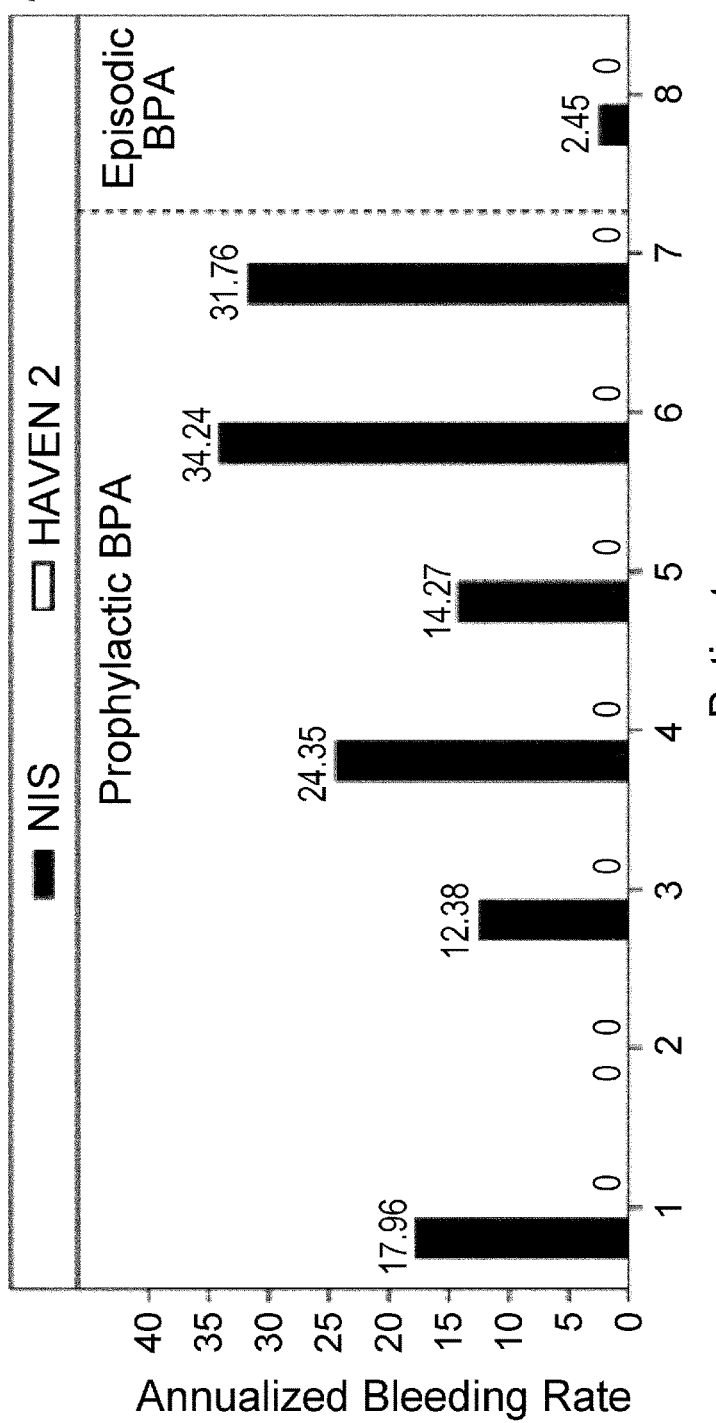

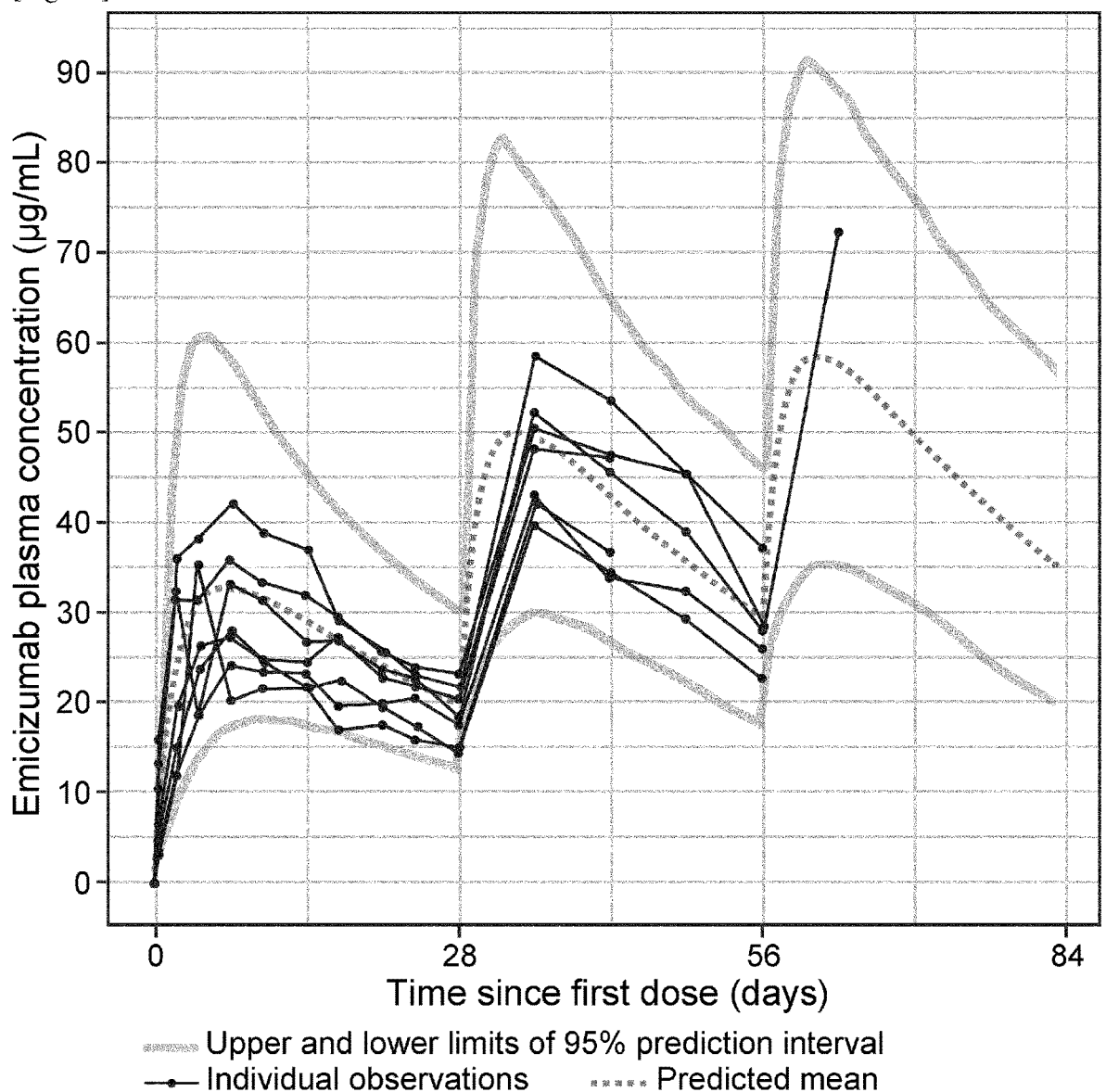
[Fig. 13]

SEQUENCE LISTING

```
<160> NUMBER OF SEQ ID NOS: 15

<210> SEQ ID NO 1
<211> LENGTH: 5
<212> TYPE: PRT
<213> ORGANISM: Artificial Sequence
<220> FEATURE:
<223> OTHER INFORMATION: Heavy chain variable region CDR1

<400> SEQUENCE: 1

Tyr Tyr Asp Ile Gln
1               5

<210> SEQ ID NO 2
<211> LENGTH: 17
<212> TYPE: PRT
<213> ORGANISM: Artificial Sequence
<220> FEATURE:
<223> OTHER INFORMATION: Heavy chain variable region CDR2
```

<400> SEQUENCE: 2

Ser Ile Ser Pro Ser Gly Gln Ser Thr Tyr Tyr Arg Arg Glu Val Lys
1               5                   10                  15

Gly

<210> SEQ ID NO 3
<211> LENGTH: 14
<212> TYPE: PRT
<213> ORGANISM: Artificial Sequence
<220> FEATURE:
<223> OTHER INFORMATION: Heavy chain variable region CDR3

<400> SEQUENCE: 3

Arg Thr Gly Arg Glu Tyr Gly Gly Gly Trp Tyr Phe Asp Tyr
1               5                   10

<210> SEQ ID NO 4
<211> LENGTH: 123
<212> TYPE: PRT
<213> ORGANISM: Artificial Sequence
<220> FEATURE:
<223> OTHER INFORMATION: Heavy chain variable region

<400> SEQUENCE: 4

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Gln Trp Val Arg Gln Ala Pro Gly Lys Gly Leu Glu Trp Val
        35                  40                  45

Ser Ser Ile Ser Pro Ser Gly Gln Ser Thr Tyr Tyr Arg Arg Glu Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Gly Arg Glu Tyr Gly Gly Gly Trp Tyr Phe Asp Tyr
            100                 105                 110

Trp Gly Gln Gly Thr Leu Val Thr Val Ser Ser
        115                 120

<210> SEQ ID NO 5
<211> LENGTH: 448
<212> TYPE: PRT
<213> ORGANISM: Artificial Sequence
<220> FEATURE:
<223> OTHER INFORMATION: Heavy chain

<400> SEQUENCE: 5

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Gln Trp Val Arg Gln Ala Pro Gly Lys Gly Leu Glu Trp Val
        35                  40                  45

Ser Ser Ile Ser Pro Ser Gly Gln Ser Thr Tyr Tyr Arg Arg Glu Val
    50                  55                  60

Lys Gly Arg Phe Thr Ile Ser Arg Asp Asn Ser Lys Asn Thr Leu Tyr
65                  70                  75                  80

-continued

```
Leu Gln Met Asn Ser Leu Arg Ala Glu Asp Thr Ala Val Tyr Tyr Cys
                 85                  90                  95

Ala Arg Arg Thr Gly Arg Glu Tyr Gly Gly Trp Tyr Phe Asp Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Cys Ser Arg Ser Thr Ser Glu Ser
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Thr Cys Asn Val
            195                 200                 205

Asp His Lys Pro Ser Asn Thr Lys Val Asp Lys Arg Val Glu Ser Lys
210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Lys Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Glu Gly Asn Val Phe Ser Cys Ser Val Met His
            420                 425                 430

Glu Ala Leu His Asn Arg Tyr Thr Gln Lys Ser Leu Ser Leu Ser Pro
            435                 440                 445

<210> SEQ ID NO 6
<211> LENGTH: 5
<212> TYPE: PRT
<213> ORGANISM: Artificial Sequence
<220> FEATURE:
<223> OTHER INFORMATION: Heavy chain variable region CDR1

<400> SEQUENCE: 6
```

Asp Asn Asn Met Asp
1               5

<210> SEQ ID NO 7
<211> LENGTH: 17
<212> TYPE: PRT
<213> ORGANISM: Artificial Sequence
<220> FEATURE:
<223> OTHER INFORMATION: Heavy chain variable region CDR2

<400> SEQUENCE: 7

Asp Ile Asn Thr Arg Ser Gly Gly Ser Ile Tyr Asn Glu Glu Phe Gln
1               5                   10                  15

Asp

<210> SEQ ID NO 8
<211> LENGTH: 10
<212> TYPE: PRT
<213> ORGANISM: Artificial Sequence
<220> FEATURE:
<223> OTHER INFORMATION: Heavy chain variable region CDR3

<400> SEQUENCE: 8

Arg Lys Ser Tyr Gly Tyr Tyr Leu Asp Glu
1               5                   10

<210> SEQ ID NO 9
<211> LENGTH: 119
<212> TYPE: PRT
<213> ORGANISM: Artificial Sequence
<220> FEATURE:
<223> OTHER INFORMATION: Heavy chain variable region

<400> SEQUENCE: 9

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Gly Ser Ile Tyr Asn Glu Glu Phe
    50                  55                  60

Gln Asp Arg Val Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Glu Trp Gly Glu Gly
            100                 105                 110

Thr Leu Val Thr Val Ser Ser
        115

<210> SEQ ID NO 10
<211> LENGTH: 444
<212> TYPE: PRT
<213> ORGANISM: Artificial Sequence
<220> FEATURE:
<223> OTHER INFORMATION: Heavy chain

<400> SEQUENCE: 10

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn

```
                  20                  25                  30
Asn Met Asp Trp Val Arg Gln Ala Pro Gly Gln Gly Leu Glu Trp Met
                35                  40                  45

Gly Asp Ile Asn Thr Arg Ser Gly Gly Ser Ile Tyr Asn Glu Glu Phe
         50                  55                  60

Gln Asp Arg Val Ile Met Thr Val Asp Lys Ser Thr Asp Thr Ala Tyr
 65                  70                  75                  80

Met Glu Leu Ser Ser Leu Arg Ser Glu Asp Thr Ala Thr Tyr His Cys
                 85                  90                  95

Ala Arg Arg Lys Ser Tyr Gly Tyr Tyr Leu Asp Glu Trp Gly Glu Gly
                100                 105                 110

Thr Leu Val Thr Val Ser Ser Ala Ser Thr Lys Gly Pro Ser Val Phe
                115                 120                 125

Pro Leu Ala Pro Cys Ser Arg Ser Thr Ser Glu Ser Thr Ala Ala Leu
                130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Thr Cys Asn Val Asp His Lys Pro
                195                 200                 205

Ser Asn Thr Lys Val Asp Lys Arg Val Glu Ser Lys Tyr Gly Pro Pro
        210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Glu Gly Asn Val Phe Ser Cys Ser Val Met His Glu Ala Leu His
                420                 425                 430

Asn His Tyr Thr Gln Glu Ser Leu Ser Leu Ser Pro
                435                 440
```

<210> SEQ ID NO 11
<211> LENGTH: 11
<212> TYPE: PRT
<213> ORGANISM: Artificial Sequence
<220> FEATURE:
<223> OTHER INFORMATION: Light chain variable region CDR1

<400> SEQUENCE: 11

Lys Ala Ser Arg Asn Ile Glu Arg Gln Leu Ala
1               5                   10

<210> SEQ ID NO 12
<211> LENGTH: 7
<212> TYPE: PRT
<213> ORGANISM: Artificial Sequence
<220> FEATURE:
<223> OTHER INFORMATION: Light chain variable region CDR2

<400> SEQUENCE: 12

Gln Ala Ser Arg Lys Glu Ser
1               5

<210> SEQ ID NO 13
<211> LENGTH: 9
<212> TYPE: PRT
<213> ORGANISM: Artificial Sequence
<220> FEATURE:
<223> OTHER INFORMATION: Light chain variable region CDR3

<400> SEQUENCE: 13

Gln Gln Tyr Ser Asp Pro Pro Leu Thr
1               5

<210> SEQ ID NO 14
<211> LENGTH: 107
<212> TYPE: PRT
<213> ORGANISM: Artificial Sequence
<220> FEATURE:
<223> OTHER INFORMATION: Light chain variable region

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Glu Arg Gln
            20                  25                  30

Leu Ala Trp Tyr Gln Gln Lys Pro Gly Gln Ala Pro Glu Leu Leu Ile
        35                  40                  45

Tyr Gln Ala Ser Arg Lys Glu Ser Gly Val Pro Asp Arg Phe Ser Gly
    50                  55                  60

Ser Arg Tyr Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Asp Pro Pro Leu
                85                  90                  95

Thr Phe Gly Gly Gly Thr Lys Val Glu Ile Lys
            100                 105

<210> SEQ ID NO 15
<211> LENGTH: 214
<212> TYPE: PRT
<213> ORGANISM: Artificial Sequence
<220> FEATURE:
<223> OTHER INFORMATION: Light chain -continued

```
<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Glu Arg Gln
            20                  25                  30

Leu Ala Trp Tyr Gln Gln Lys Pro Gly Gln Ala Pro Glu Leu Leu Ile
        35                  40                  45

Tyr Gln Ala Ser Arg Lys Glu Ser Gly Val Pro Asp Arg Phe Ser Gly
    50                  55                  60

Ser Arg Tyr Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Asp Pro Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210
```

METHODS OF USING A BISPECIFIC ANTIBODY THAT RECOGNIZES COAGULATION FACTOR IX AND/OR ACTIVATED COAGULATION FACTOR IX AND COAGULATION FACTOR X AND/OR ACTIVATED COAGULATION FACTOR X

The present application is the National Stage of International Application No. PCT/JP2017/031933, filed Sep. 5, 2017, which claims the benefit of U.S. Provisional Application No. 62/383,933 filed Sep. 6, 2016, U.S. Provisional Application No. 62/437,281 filed Dec. 21, 2016, and U.S. Provisional Application No. 62/485,514 filed Apr. 14, 2017. The entire disclosures of these applications are hereby incorporated by reference.

TECHNICAL FIELD

The present invention relates generally to the field of therapeutics for bleeding disorders.

BACKGROUND ART

Hemophilia is a hemorrhagic disease caused by a congenital deficiency or dysfunction of coagulation factor VIII (FVIII) or coagulation factor IX (FIX). The former is called hemophilia A and the latter is called hemophilia B. Genes for both factors are located on the X chromosome, and since genetic defects take the X-chromosome-linked recessive hereditary form, 99% or more of the patients who develop the disease are men. It is known that the prevalence rate is approximately one in 10,000 live male births, and the ratio between hemophilia A and hemophilia B is approximately 5:1.

The severity of hemophilia A is defined by the FVIII activity in blood. Patients with an activity of less than 1% are classified as severe, patients with an activity of 1% to 5% are classified as moderate, and patients with an activity of more than 5% and less than 40% are classified as mild. Severe patients who account for approximately half of hemophilia A patients exhibit bleeding symptoms several times a month, and this frequency is markedly high as compared to those of moderate and mild patients.

For bleeding in hemophilia A patients, FVIII formulations are generally administered on demand (on-demand therapy). In recent years, FVIII formulations are also administered prophylactically to prevent bleeding events (regular replacement therapy; NPLs 1 and 2). The half-life of FVIII formulations in blood is approximately 8 to 19 hours. Therefore, for continuous prevention, FVIII formulations are administered to patients three times a week (NPLs 3 and 4). In on-demand therapy, FVIII formulations are also additionally administered at regular intervals as necessary to prevent reoccurrence of bleeding. In addition, FVIII formulations are mainly administered at home, but since they are administered intravenously, the difficulty of securing a blood vessel is a problem. Therefore, there has been a strong need for pharmaceutical agents with a lesser burden regarding their administration as compared to FVIII formulations.

Occasionally, antibodies against FVIII (inhibitors) develop in hemophilia A patients. Such inhibitors counteract the effects of the FVIII formulations. For bleeding in patients who have developed inhibitors (inhibitor patients), bypassing agents are administered. Their mechanisms of action are not dependent on FVIII function, that is, on the function of catalyzing the activation of blood coagulation factor X (FX) by activated blood coagulation factor IX (FIXa). Therefore, in some cases, bypassing agents cannot sufficiently stop the bleeding. Recently, results suggesting the effectiveness of regular administration therapy of bypassing agents have been obtained, but this has not yielded a sufficient effect to suppress bleeding as compared to FVIII formulations. Accordingly, there has been a strong need for therapeutic agents that can be administered subcutaneously, as well as long-acting therapeutic agents that can be administered less frequently, regardless of the presence of inhibitors.

Recently, as a means for solving the problem, an antibody that functionally substitutes for FVIII, emicizumab (ACE910, R05534262) and its use were disclosed (PTLs 1, 2, 3, 4, and 5, NPLs 5, 6, 7, and 8).

Emicizumab is a recombinant humanized bispecific antibody that binds to (a) FIX and/or FIXa and (b) FX and/or activated blood coagulation factor FX (FXa), and mimics the cofactor function of FVIII. Japanese patients with severe hemophilia A (with or without factor VIII inhibitors) were enrolled in an open-label, non-randomized, inter-individual dose-escalation study of emicizumab. Enrolled patients were assigned to cohort 1, cohort 2, or cohort 3, and received subcutaneous emicizumab at an initial dose of 1.0 mg per kilogram of body weight (cohort 1) or 3 mg per kilogram (cohorts 2 and 3) at week 0 (day 1), followed by a once-weekly subcutaneous dose of 0.3, 1.0, or 3 mg per kilogram (cohorts 1, 2, and 3, respectively) from week 1 through week 12. The initial and subsequent doses for cohort 3 were the same. Emicizumab decreased the annualized bleeding rates (ABR) in patients who had hemophilia A with or without factor VIII inhibitors (NPL 9). At the completion of the 12-week study, eligible patients were able to participate in an extension study (NPL 10).

CITATION LIST

Patent Literature

[PTL 1] WO 2005/035754
[PTL 2] WO 2005/035756
[PTL 3] WO 2006/109592
[PTL 4] WO 2012/067176
[PTL 5] WO 2015/194233

Non-Patent Literature

[NPL 1] Blood 58, 1-13 (1981)
[NPL 2] Nature 312, 330-337 (1984)
[NPL 3] Nature 312, 337-342 (1984)
[NPL 4] Biochim. Biophys. Acta 871, 268-278 (1986)
[NPL 5] Nature Medicine 18, 1570-1574(2012)
[NPL 6] PLOS ONE 8, 1-13(2013)
[NPL 7] J Thromb Haemost. 12, 206-213(2014)
[NPL 8] Blood 127(13), 1633-1641(2016)
[NPL 9] N Engl J Med. 374(21), 2044-2053(2016)
[NPL 10] XXV Congress of the International Society on Thrombosis and Haemostasis, Toronto, Canada, Jun. 20-25, 2015. Abstr AS017.

SUMMARY OF INVENTION

Technical Problem

An objective of the present invention is to provide another effective pharmaceutical composition or a dosage regimen for treating and/or reducing the incidence of a disease that develops and/or progresses due to a decrease or deficiency in the activity of FVIII and/or activated blood coagulation factor VIII (FVIIIa).

Solution to Problem

As a result of dedicated research, the present inventors succeeded in discovering an effective dosage regimen for a pharmaceutical composition containing a bispecific antigen-binding molecule (antibody) that recognizes (a) FIX and/or FIXa and (b) FX and/or FXa for treating and/or reducing the incidence of a disease that develops and/or progresses due to a decrease or deficiency in the activity of FVIII and/or FVIIIa.

Specifically, the present invention relates to a pharmaceutical composition or a dosage regimen used for treating and/or reducing the incidence of a disease that develops and/or progresses due to a decrease or deficiency in the activity of FVIII and/or FVIIIa, and specifically relates to the following:

[1] a method for treating and/or reducing the incidence of a disease that develops and/or progresses due to a decrease or deficiency in the activity of blood coagulation factor VIII and/or activated blood coagulation factor VIII (FVIIIa), the method comprising: administering to a subject a bispecific antibody that recognizes (a) blood coagulation factor IX and/or activated blood coagulation factor IX and (b) blood coagulation factor X and/or activated blood coagulation factor X at a weekly loading dose of 3 mg/kg or 4.5 mg/kg of the antibody for one or more weeks or at an every-two-week loading dose of 6 mg/kg of the antibody for two or more weeks; and, after the loading dose administration(s) are complete, administering a maintenance dose of the antibody to the subject one or more times, the maintenance dose being 6 mg/kg of the antibody;

[2] the method of [1], wherein the maintenance dose of 6 mg/kg of the antibody is administered to the subject every four weeks or every month in a single dose or multiple divided doses;

[3] the method of [1] or [2], wherein the antibody is administered at the weekly loading dose of 3 mg/kg of the antibody for four weeks, followed by the maintenance dose;

[4] the method of [1] or [2], wherein the antibody is administered at the weekly loading dose of 4.5 mg/kg of the antibody for two weeks, followed by the maintenance dose;

[5] the method of [1] or [2], wherein the antibody is administered at the every-two-week loading dose of 6 mg/kg of the antibody for four weeks, followed by the maintenance dose;

[6] the method of any one of [1] to [5], wherein the maintenance dose is administered in one single dose at 6 mg/kg of the antibody monthly or every four weeks;

[7] the method of any one of [1] to [5], wherein the maintenance dose is administered in two single doses of the antibody, each at 3 mg/kg, monthly or every four weeks, wherein one single dose of the maintenance dose at 3 mg/kg of the antibody is administered once every two weeks;

[8] the method of any one of [1] to [5], wherein the maintenance dose is administered in four single doses each at 1.5 mg/kg of the antibody monthly or every four weeks, wherein one single dose of the maintenance dose at 1.5 mg/kg of the antibody is administered once every week;

[9] the method of any one of [1] to [8] further comprising, in a case of no or insufficient effect of treating and/or reducing the incidence of the disease by administering the maintenance dose of the antibody, stopping administering the maintenance dose of the antibody and starting administering an alternative maintenance dose of the antibody to the subject, the alternative maintenance dose being a weekly dose of 3 mg/kg of the antibody or an every-two-week dose of 6 mg/kg of the antibody;

[10] a method for treating and/or reducing the incidence of a disease that develops and/or progresses due to a decrease or deficiency in the activity of blood coagulation factor VIII and/or activated blood coagulation factor VIII (FVIIIa), the method comprising: administering to a subject a bispecific antibody that recognizes (a) blood coagulation factor IX and/or activated blood coagulation factor IX and (b) blood coagulation factor X and/or activated blood coagulation factor X at a weekly loading dose of 4.5 mg/kg of the antibody for four weeks; and thereafter administering a maintenance dose of the antibody to the subject one or more times, the maintenance dose being 9 mg/kg of the antibody which is administered every four weeks or every month in two or four divided doses;

[11] a method for treating and/or reducing the incidence of a disease that develops and/or progresses due to a decrease or deficiency in the activity of blood coagulation factor VIII and/or activated blood coagulation factor VIII (FVIIIa), the method comprising: administering to a subject a bispecific antibody that recognizes (a) blood coagulation factor IX and/or activated blood coagulation factor IX and (b) blood coagulation factor X and/or activated blood coagulation factor X at a weekly loading dose of 6 mg/kg of the antibody for four weeks; and thereafter administering a maintenance dose of the antibody to the subject one or more times, the maintenance dose being 12 mg/kg of the antibody which is administered every four weeks or every month in two or four divided doses;

[12] the method of [10] further comprising, in a case of no or insufficient effect of treating and/or reducing the incidence of the disease by administering the maintenance dose of the antibody, stopping administering the maintenance dose of the antibody and starting administering an alternative maintenance dose of the antibody to the subject, the alternative maintenance dose being a weekly dose of 4.5 mg/kg of the antibody;

[13] the method of [11] further comprising, in a case of no or insufficient effect of treating and/or reducing the incidence of the disease by administering the maintenance dose of the antibody, stopping administering the maintenance dose of the antibody and starting administering an alternative maintenance dose of the antibody to the subject, the alternative maintenance dose being a weekly dose of 6 mg/kg of the antibody;

[14] the method of any one of [1] to [13], wherein the antibody is emicizumab; and

[15] the method of [14], wherein the disease that develops and/or progresses due to a decrease or deficiency in the activity of blood coagulation factor VIII and/or activated blood coagulation factor VIII is selected from the group consisting of hemophilia A, acquired hemophilia A, von Willebrand disease, and hemophilia A with emergence of an inhibitor against blood coagulation factor VIII and/or activated blood coagulation factor VIII.

Furthermore, the present invention relates to:

[16] a pharmaceutical composition for use in treating and/or reducing the incidence of a disease that develops and/or progresses due to a decrease or deficiency in the activity of blood coagulation factor VIII and/or activated blood coagulation factor VIII (FVIIIa), wherein the composition comprises a bispecific antibody that recognizes (a) blood coagulation factor IX and/or activated blood coagulation factor IX and (b) blood coagulation factor X and/or activated blood coagulation factor X, wherein the bispecific antibody is administered at a weekly loading dose of 3 mg/kg or 4.5 mg/kg of the antibody for one or more weeks or at an every-two-week loading dose of 6 mg/kg of the antibody for two or more weeks and, after the loading dose administration(s) are complete, is administered at a maintenance dose one or more times, the maintenance dose being 6 mg/kg of the antibody;

[17] a pharmaceutical composition for use in treating and/or reducing the incidence of a disease that develops and/or progresses due to a decrease or deficiency in the activity of blood coagulation factor VIII and/or activated blood coagulation factor VIII (FVIIIa), wherein the composition comprises a bispecific antibody that recognizes (a) blood coagulation factor IX and/or activated blood coagulation factor IX and (b) blood coagulation factor X and/or activated blood coagulation factor X, wherein the bispecific antibody is administered at a weekly loading dose of 4.5 mg/kg of the antibody for four weeks and thereafter is administered at a maintenance dose one or more times, the maintenance dose being 9 mg/kg of the antibody which is administered every four weeks or every month in two or four divided doses;

[18] a pharmaceutical composition for use in treating and/or reducing the incidence of a disease that develops and/or progresses due to a decrease or deficiency in the activity of blood coagulation factor VIII and/or activated blood coagulation factor VIII (FVIIIa), wherein the composition comprises a bispecific antibody that recognizes (a) blood coagulation factor IX and/or activated blood coagulation factor IX and (b) blood coagulation factor X and/or activated blood coagulation factor X, wherein the bispecific antibody is administered at a weekly loading dose of 6 mg/kg of the antibody for four weeks and thereafter is administered at a maintenance dose one or more times, the maintenance dose being 12 mg/kg of the antibody which is administered every four weeks or every month in two or four divided doses;

[19] a product comprising (i) a container; (ii) a pharmaceutical composition in the container, wherein the composition comprises a bispecific antibody that recognizes (a) blood coagulation factor IX and/or activated blood coagulation factor IX and (b) blood coagulation factor X and/or activated blood coagulation factor X; and (iii) a document instructing (a) administration of the bispecific antibody at a weekly loading dose of 3 mg/kg or 4.5 mg/kg of the antibody for one or more weeks or at an every-two-week loading dose of 6 mg/kg of the antibody for two or more weeks and (b) one or more administration(s) of a maintenance dose of the bispecific antibody after the loading dose administration(s) are complete, the maintenance dose being 6 mg/kg of the antibody;

[20] a product comprising (i) a container; (ii) a pharmaceutical composition in the container, wherein the composition comprises a bispecific antibody that recognizes (a) blood coagulation factor IX and/or activated blood coagulation factor IX and (b) blood coagulation factor X and/or activated blood coagulation factor X; and (iii) a document instructing (a) administration of the bispecific antibody at a weekly loading dose of 4.5 mg/kg of the antibody for four weeks and (b) one or more administrations of a maintenance dose of the bispecific antibody after the loading dose administration(s) are complete, the maintenance dose being 9 mg/kg of the antibody which is administered every four weeks or every month in two or four divided doses;

[21] a product comprising (i) a container; (ii) a pharmaceutical composition in the container, wherein the composition comprises a bispecific antibody that recognizes (a) blood coagulation factor IX and/or activated blood coagulation factor IX and (b) blood coagulation factor X and/or activated blood coagulation factor X; and (iii) a document instructing (a) administration of the bispecific antibody at a weekly loading dose of 6 mg/kg of the antibody for four weeks and (b) one or more administrations of a maintenance dose of the bispecific antibody after the loading dose administration(s) are complete, the maintenance dose being 12 mg/kg of the antibody which is administered every four weeks or every month in two or four divided doses;

[22] a bispecific antibody for use in treating and/or reducing the incidence of a disease that develops and/or progresses due to a decrease or deficiency in the activity of blood coagulation factor VIII and/or activated blood coagulation factor VIII (FVIIIa), wherein the bispecific antibody recognizes (a) blood coagulation factor IX and/or activated blood coagulation factor IX and (b) blood coagulation factor X and/or activated blood coagulation factor X and is administered at a weekly loading dose of 3 mg/kg or 4.5 mg/kg of the antibody for one or more weeks or at an every-two-week loading dose of 6 mg/kg of the antibody for two or more weeks and, after the loading dose administration(s) are complete, is administered at a maintenance dose one or more times, the maintenance dose being 6 mg/kg of the antibody;

[23] a bispecific antibody for use in treating and/or reducing the incidence of a disease that develops and/or progresses due to a decrease or deficiency in the activity of blood coagulation factor VIII and/or activated blood coagulation factor VIII (FVIIIa), wherein the bispecific antibody recognizes (a) blood coagulation factor IX and/or activated blood coagulation factor IX and (b) blood coagulation factor X and/or activated blood coagulation factor X and is administered at a weekly loading dose of 4.5 mg/kg of the antibody for four weeks and thereafter is administered at a maintenance dose one or more times, the maintenance dose being 9 mg/kg of the antibody which is administered every four weeks or every month in two or four divided doses;

[24] a bispecific antibody for use in treating and/or reducing the incidence of a disease that develops and/or progresses due to a decrease or deficiency in the activity of blood coagulation factor VIII and/or activated blood coagulation factor VIII (FVIIIa), wherein the bispecific antibody recognizes (a) blood coagulation factor IX and/or activated blood coagulation factor IX and (b) blood coagulation factor X and/or activated blood coagulation factor X and is administered at a weekly loading dose of 6 mg/kg of the antibody for four weeks and thereafter is administered a maintenance dose one or more times, the maintenance dose being 12 mg/kg of the antibody which is administered every four weeks or every month in two or four divided doses;

[25] use of a bispecific antibody in the manufacture of a pharmaceutical composition used for treating and/or reducing the incidence of a disease that develops and/or progresses due to a decrease or deficiency in the activity of blood coagulation factor VIII and/or activated blood coagulation factor VIII (FVIIIa), wherein the bispecific antibody recognizes (a) blood coagulation factor IX and/or activated blood coagulation factor IX and (b) blood coagulation factor X and/or activated blood coagulation factor X, and is administered at a weekly loading dose of 3 mg/kg or 4.5 mg/kg of the antibody for one or more weeks or at an every-two-week loading dose of 6 mg/kg of the antibody for two or more weeks and, after the loading dose administration(s) are complete, is administered at a maintenance dose one or more times, the maintenance dose being 6 mg/kg of the antibody;

[26] use of a bispecific antibody in the manufacture of a pharmaceutical composition used for treating and/or reducing the incidence of a disease that develops and/or progresses due to a decrease or deficiency in the activity of blood coagulation factor VIII and/or activated blood coagulation factor VIII (FVIIIa), wherein the bispecific antibody recognizes (a) blood coagulation factor IX and/or activated blood coagulation factor IX and (b) blood coagulation factor X and/or activated blood coagulation factor X, and is administered at a weekly loading dose of 4.5 mg/kg of the antibody for four weeks and thereafter is administered at a maintenance dose one or more times, the maintenance dose being 9 mg/kg of the antibody which is administered every four weeks or every month in two or four divided doses; and

[27] use of a bispecific antibody in the manufacture of a pharmaceutical composition used for treating and/or reducing the incidence of a disease that develops and/or progresses due to a decrease or deficiency in the activity of blood coagulation factor VIII and/or activated blood coagulation factor VIII (FVIIIa), wherein the bispecific antibody recognizes (a) blood coagulation factor IX and/or activated blood coagulation factor IX and (b) blood coagulation factor X and/or activated blood coagulation factor X, and is administered at a weekly loading dose of 6 mg/kg of the antibody for four weeks and thereafter is administered at a maintenance dose one or more times, the maintenance dose being 12 mg/kg of the antibody which is administered every four weeks or every month in two or four divided doses.

BRIEF DESCRIPTION OF DRAWINGS

FIG. 1 shows the simulated annual bleeding rate over plasma emicizumab concentrations. X-axis shows plasma emicizumab concentration (micro g/mL). Y-axis shows cumulative bleeding count for 52 weeks. Circles and solid line show the simulated medians plotted at each plasma emicizumab concentration. Shaded area shows the simulated 5th- to 95th-percentile range.

FIG. 2 shows the simulated change in plasma emicizumab concentration over time (weekly dosing). X-axis shows time (week) after first emicizumab administration. Y-axis shows plasma emicizumab concentration (micro g/mL). Circles and solid line show the simulated medians plotted at each trough sampling time point. Shaded area shows the simulated 5th- to 95th-percentile range. Broken line shows the target exposure level of 45 micro g/mL. Once-weekly loading dose of 3 mg/kg for first 4 weeks followed by once-weekly maintenance dose of 1.5 mg/kg was applied.

FIG. 3 shows the simulated change in plasma emicizumab concentration over time (two-weekly dosing). X-axis shows time (week) after first emicizumab administration. Y-axis shows plasma emicizumab concentration (micro g/mL). Circles and solid line show the simulated medians plotted at each trough sampling time point. Shaded area shows the simulated 5th- to 95th-percentile range. Broken line shows the target exposure level of 45 micro g/mL. Once-weekly loading dose of 3 mg/kg for first 4 weeks followed by once-every-two-week maintenance dose of 3 mg/kg was applied.

FIG. 4 shows the simulated change in plasma emicizumab concentration over time (four-weekly dosing). X-axis shows time (week) after first emicizumab administration. Y-axis shows plasma emicizumab concentration (micro g/mL). Circles and solid line show the simulated medians plotted at each trough sampling time point. Shaded area shows the simulated 5th- to 95th-percentile range. Broken line shows the target exposure level of 45 micro g/mL. Once-weekly loading dose of 3 mg/kg for first 4 weeks followed by once-every-four-week maintenance dose of 6 mg/kg was applied.

FIG. 5 shows the simulated distribution of annual bleeding rate (weekly dosing). X-axis shows cumulative bleeding count for 52 weeks. Y-axis shows proportion of patients having each cumulative bleeding count for 52 weeks (%). Bars show the simulated proportions. Once-weekly loading dose of 3 mg/kg for first 4 weeks followed by once-weekly maintenance dose of 1.5 mg/kg was applied.

FIG. 6 shows the simulated distribution of annual bleeding rate (two-weekly dosing). X-axis shows cumulative bleeding count for 52 weeks. Y-axis shows proportion of patients having each cumulative bleeding count for 52 weeks (%). Bars show the simulated proportions. Once-weekly loading dose of 3 mg/kg for first 4 weeks followed by once-every-two-week maintenance dose of 3 mg/kg was applied.

FIG. 7 shows the simulated distribution of annual bleeding rate (four-weekly dosing). X-axis shows cumulative bleeding count for 52 weeks. Y-axis shows proportion of patients having each cumulative bleeding count for 52 weeks (%). Bars show the simulated proportions. Once-weekly loading dose of 3 mg/kg for first 4 weeks followed by once-every-four-week maintenance dose of 6 mg/kg was applied.

FIG. 8 shows the annualized bleeding rates for study Arms A, B, and C in HAVEN 1 (Example 2). ABR, annualized bleeding rate; BPA, bypassing agent; RR, relative risk.

FIG. 9 shows the intra-participant comparison for treated bleeds in participants who received emicizumab prophylaxis (Arm C). Treated bleeds during the period when a participant received emicizumab prophylaxis are compared with treated bleeds during the period when the same participant had received previous prophylactic BPA treatment in 24 weeks prior to study entry in HAVEN 1.

FIG. 10 shows the observed trough emicizumab concentrations over time with once-weekly dosing (once-weekly loading dose of 3 mg/kg for first 4 weeks followed by once-weekly maintenance dose of 1.5 mg/kg) in HAVEN 1. SD, standard deviation.

FIG. 11 shows the intra-participant comparison for treated bleeds in participants who received emicizumab prophylaxis (Arm A). Treated bleeds during the period when a participant received emicizumab prophylaxis are compared with treated bleeds during the period when the same participant had received previous episodic BPA treatment in 24 weeks prior to study entry in HAVEN 1.

FIG. 12 shows the individual patient-calculated ABR for treated bleeds in HAVEN 2. The intra-participant comparison included patients previously enrolled in the NIS who were enrolled in HAVEN 2 for at least 12 weeks. Seven patients received prophylactic treatment with bypassing agents prior to the study, one received episodic treatment with bypassing agents. ABR, annualized bleeding rate; BPA, bypassing agent; NIS, non-interventional study.

FIG. 13 shows the observed and predicted emicizumab concentrations over time with once-four-weekly dosing in the PK Run-in Part of HAVEN 4 (Example 5). Emicizumab was administered subcutaneously at 6 mg/kg once every 4 weeks. Black dots and solid lines show the individual observations. Gray broken line shows the predicted mean. Gray bold solid lines indicate the upper and lower limits of the 95% prediction interval.

DESCRIPTION OF EMBODIMENTS

A bispecific antigen-binding molecule that recognizes (a) blood coagulation factor IX (FIX) and/or activated blood coagulation factor IX (FIXa) and (b) blood coagulation factor X (FX) and/or activated blood coagulation factor X (FXa) preferably has an activity of functionally substituting for coagulation factor VIII (FVIII).

In the present invention, the phrase "functionally substitute for FVIII" means that (a) FIX and/or FIXa, and (b) FX and/or FXa are recognized, and the activation of FX by FIXa is promoted (FXa generation by FIXa is promoted). FXa generation-promoting activity can be evaluated using, for example, a measurement system comprising FIXa, FX, the synthetic substrate S-2222 (a synthetic substrate of FXa), and phospholipids. Such a measurement system shows the correlation between the severity of the disease and the clinical symptoms in hemophilia A cases (Rosen S, Andersson M, Blomback M et al. Clinical applications of a chromogenic substrate method for determination of FVIII activity. Thromb Haemost 1985; 54: 811-23).

Such antigen-binding molecules (such as antibodies) recognizing (a) FIX and/or FIXa and (b) FX and/or FXa can be obtained according to methods described, for example, in WO2005/035756, WO2006/109592, and WO2012/067176. Specifically, based on the sequences of antibodies against FIX and/or FIXa and antibodies against FX and/or FXa, antibodies can be generated using genetic recombination techniques known to those skilled in the art. Polynucleotide (s) encoding an antibody can be constructed based on the sequences of the antibodies against FIX and/or FIXa and antibodies against FX and/or FXa, and this can be inserted into an expression vector and subsequently expressed in appropriate host cells (see for example, Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; and Bird, R. E. and Walker, B. W., Trends Biotechnol. (1991) 9, 132-137).

In the present invention, the phrases "functionally substitute for FVIII" and "functionally substitute for FVIIIa" are used interchangeably.

Such bispecific antigen-binding molecules can be isolated from inside host cells or from outside the cells (such as from the medium), and can be purified as substantially pure and homogeneous antibodies. Isolation and purification of antibodies can be carried out using methods generally used for isolating and purifying antibodies. The methods are not limited and, for example, antibodies can be isolated and purified by appropriately selecting and combining column chromatography columns, filters, ultrafiltration, salting-out, solvent precipitation, solvent extraction, distillation, immunoprecipitation, SDS-polyacrylamide gel electrophoresis, isoelectric focusing, dialysis, recrystallization, and such.

The bispecific antigen-binding molecules of the present invention include the antibodies described, for example, in WO2005/035756, WO2006/109592, and WO2012/067176.

A bispecific antigen-binding molecule comprises a first antigen-binding site and a second antigen-binding site which can specifically bind to at least two different types of antigens. While the first antigen-binding site and the second antigen-binding site of the bispecific antigen-binding molecule of the present invention are not particularly limited as long as they have an activity to bind to (a) FIX and/or FIXa, and (b) FX and/or FXa, respectively, examples include sites necessary for binding with antigens, such as antibodies, scaffold molecules (antibody-like molecules), and peptides, and fragments containing such sites. A scaffold molecule is a molecule that exhibits a function by binding to a target molecule, and any polypeptide may be used as long as it is a conformationally stable polypeptide that can bind to at least one target antigen. Examples of such polypeptides include antibody variable regions, fibronectin (WO 2002/032925), protein A domain (WO 1995/001937), LDL receptor A domain (WO 2004/044011, WO 2005/040229), ankyrin (WO 2002/020565), as well as the molecules described in Nygren et al. (Current Opinion in Structural Biology, 7: 463-469 (1997); and Journal of Immunol Methods, 290: 3-28 (2004)), Binz et al. (Nature Biotech 23: 1257-1266 (2005)), and Hosse et al. (Protein Science 15: 14-27(2006)). Furthermore, as described in Curr Opin Mol Ther. 2010 August; 12(4): 487-95 and Drugs. 2008; 68(7): 901-12, peptide molecules that can bind to the target antigens can also be used.

Bispecific antigen-binding molecules can be produced using, for example, genetic recombination techniques (see, for example, Borrebaeck C A K and Larrick J W, THERAPEUTIC MONOCLONAL ANTIBODIES, Published in the United Kingdom by MACMILLAN PUBLISHERS LTD, 1990). Recombinant antibodies can be obtained by cloning DNAs encoding the antibodies from hybridomas or antibody-producing cells, such as sensitized lymphocytes that produce antibodies, inserting them into suitable vectors, and then introducing them into hosts (host cells) to produce the antibodies.

Furthermore, bispecific antigen-binding molecules may be whole antibodies, and may also be antibody fragments and low-molecular-weight antibodies, and modified antibodies.

For example, antibody fragments and low-molecular-weight antibodies include diabodies (Dbs), linear antibodies, and single chain antibody (hereinafter, also denoted as scFv) molecules. Herein, an "Fv" fragment is a smallest antibody fragment and comprises a full antigen recognition site and binding site.

Bispecific antibodies include human antibodies, mouse antibodies, rat antibodies, and such, and their origins are not limited. They may also be genetically modified antibodies, such as chimeric antibodies and humanized antibodies.

Methods for obtaining human antibodies are already known. For example, a human antibody of interest can be obtained by immunizing a transgenic animal carrying the entire repertoire of human antibody genes with an antigen of interest (see International Publication No. WO 93/12227, WO 92/03918, WO 94/02602, WO 94/25585, WO 96/34096, and WO 96/33735).

Genetically modified antibodies can also be produced using known methods. Specifically, for example, a chimeric antibody is an antibody that comprises H chain and L chain variable regions of an immunized animal antibody, and H chain and L chain constant regions of a human antibody. Chimeric antibodies can be obtained by linking DNAs encoding the variable regions of an antibody derived from an immunized animal with DNAs encoding the constant regions of a human antibody, inserting this into an expression vector, and then introducing this into host cells to produce the antibodies.

A humanized antibody is a modified antibody which is also often referred to as a reshaped human antibody. A humanized antibody is constructed by transferring the CDRs of an antibody derived from an immunized animal to the complementarity determining regions of a human antibody. General genetic recombination techniques for producing them are also known (see European Patent Application Publication No. EP 239400; International Publication No.

WO 96/02576; Sato K et al., Cancer Research 1993, 53: 851-856; International Publication No. WO 99/51743).

More specifically, the bispecific antigen-binding molecule of the present invention is a bispecific antibody in which a first polypeptide and a third polypeptide are associated and a second polypeptide and a fourth polypeptide are associated, and is preferably emicizumab (ACE910, R05534262) described below:

(a) a bispecific antibody comprising a first polypeptide which is an H chain containing an H chain variable region containing CDR 1, 2, and 3 amino acid sequences of SEQ ID NOs: 1, 2, and 3, respectively; a second polypeptide which is an H chain containing an H chain variable region containing CDR 1, 2, and 3 amino acid sequences of SEQ ID NOs: 6, 7, and 8, respectively; and a third and fourth polypeptide which are a commonly shared L chain containing an L chain variable region containing CDR 1, 2, and 3 amino acid sequences of SEQ ID NOs: 11, 12, and 13, respectively;

(b) a bispecific antibody comprising a first polypeptide which is an H chain containing an H chain variable region amino acid sequence of SEQ ID NO: 4; a second polypeptide which is an H chain containing an H chain variable region amino acid sequence of SEQ ID NO: 9; and a third and fourth polypeptide which are a commonly shared L chain containing an L chain variable region amino acid sequence of SEQ ID NO: 14; or (c) a bispecific antibody comprising a first polypeptide which is an H chain containing the amino acid sequence of SEQ ID NO: 5; a second polypeptide which is an H chain containing the amino acid sequence of SEQ ID NO: 10; and a third and fourth polypeptide which are a commonly shared L chain containing the amino acid sequence of SEQ ID NO: 15 (Q499-z121/J327-z119/L404-k).

Pharmaceutical compositions of the present invention which are used for therapeutic or preventive purposes can be prepared by mixing a therapeutic agent, if necessary, with suitable pharmaceutically acceptable carriers, vehicles, and such and made into a freeze-dry formulation or a solution formulation.

A "therapeutic agent" herein refers to the bispecific antigen-binding molecules of the present invention.

Examples of suitable pharmaceutically acceptable carriers and vehicles include sterilized water, physiological saline, stabilizers, excipients, antioxidants (such as ascorbic acid), buffers (such as phosphate, citrate, histidine, and other organic acids), antiseptics, surfactants (such as PEG and Tween), chelating agents (such as EDTA), and binders. They may also contain other low-molecular-weight polypeptides, proteins such as serum albumin, gelatin, and immunoglobulins, amino acids such as glycine, glutamine, asparagine, glutamic acid, aspartic acid, methionine, arginine, and lysine, sugars and carbohydrates such as polysaccharides and monosaccharides, and sugar alcohols such as mannitol and sorbitol. When preparing an aqueous solution for injection, for example, physiological saline and isotonic solutions containing glucose and other adjuvants such as D-sorbitol, D-mannose, D-mannitol, and sodium chloride may be used, and appropriate solubilizers such as alcohol (for example, ethanol), polyalcohols (such as propylene glycol and PEG), and nonionic surfactants (such as polysorbate 80, polysorbate 20, poloxamer 188, and HCO-50) may be used in combination. By mixing hyaluronidase into the formulation, a larger fluid volume can be administered subcutaneously (Expert Opin Drug Deliv. 2007 July; 4(4): 427-40). Further, the pharmaceutical compositions of the present invention may be preliminarily loaded in a syringe. Meanwhile, the solution formulation can be prepared according to the method described in WO 2011/090088.

If necessary, the antigen-binding molecules of the present invention can be encapsulated in microcapsules (e.g., those made of hydroxymethylcellulose, gelatin, and poly(methylmetacrylate)), or prepared as colloidal drug delivery systems (e.g., liposomes, albumin microspheres, microemulsion, nanoparticles, and nanocapsules) (see, for example, "Remington's Pharmaceutical Science 16th edition", Oslo Ed. (1980)). Methods for preparing the pharmaceutical agents as controlled-release pharmaceutical agents are also well known, and such methods may be applied to the antigen-binding molecules of the present invention (Langer et al., J. Biomed. Mater. Res. 15: 267-277 (1981); Langer, Chemtech. 12: 98-105 (1982); U.S. Pat. No. 3,773,919; European Patent Application Publication No. EP 58,481; Sidman et al., Biopolymers 22: 547-556 (1983); EP 133, 988).

A preferable liquid formulation is as follows.
20 mg/ml to 180 mg/ml emicizumab,
0.2 mg/ml to 1 mg/ml of poloxamer 188,
10 mM to 40 mM of histidine-aspartic acid buffer,
100 mM to 300 mM of arginine, at a pH of about 4.5 to 6.5.

The pharmaceutical compositions of the present invention can be administered to a patient via any appropriate route, for example, intravenously by bolus injection or continuous infusion for a given period, intramuscularly, intraperitoneally, intracerebrospinally, transdermally, subcutaneously, intraarticularly, sublingually, intrasynovially, orally, by inhalation, locally, or externally. Intravenous administration or subcutaneous administration is preferred.

The term "4 weeks" or "a month" as used herein are used interchangeably and the term "every 4 weeks", "4-weekly", "every month", or "monthly" as used herein are used interchangeably.

The term "every 2 weeks", "2-weekly", or "bi-weekly" as used herein are used interchangeably.

A "maintenance" dose herein refers to one or more doses of a therapeutic agent administered to the patient over a treatment period. Different maintenance doses and different administration intervals can be combined.

In one aspect, the maintenance dose is between 0.3 mg/kg to 24 mg/kg of the antibody.

In one aspect, the administration interval is between one week to 24 weeks or 6 months.

In one aspect, the maintenance dose is 6 mg/kg of the antibody. The maintenance dose of 6 mg/kg refers to, for example, administering total 6 mg/kg of the antibody during 4 weeks or every month in a single dose or multiple divided doses.

In certain embodiment, the maintenance dose is 6 mg/kg of the antibody and this is administered in a single dose and the administration interval is 4 weeks (every month). In this case one single dose is administered during a month or 4 weeks.

In another embodiment, the maintenance dose is 6 mg/kg of the antibody and this is administered in two divided doses each containing 3 mg/kg of the antibody and the administration interval is two weeks (every 2 weeks). In this case two doses are administered during a month or 4 weeks.

In another embodiment, the maintenance dose is 6 mg/kg of the antibody and this is administered in four divided doses each containing 1.5 mg/kg of the antibody and the administration interval is one week (every week). In this case four doses are administered during a month or 4 weeks.

In certain embodiment, the maintenance dose is 6 mg/kg of the antibody in a single dose and the administration interval is 4 weeks (every month) and in this case one dose is administered during a month or 4 weeks.

In another embodiment, the maintenance dose is 3 mg/kg of the antibody in a single dose and the administration interval is two weeks (every 2 weeks) and in this case two doses are administered during a month or 4 weeks.

In another embodiment, the maintenance dose is 1.5 mg/kg of the antibody in a single dose and the administration interval is one week (every week) and in this case four doses are administered during a month or 4 weeks.

In another aspect, the maintenance dose is 9 mg/kg of the antibody. The maintenance dose of 9 mg/kg refers to, for example, administering total 9 mg/kg of the antibody during 4 weeks or every month in a single dose or multiple divided doses. This can be applicable for pediatric patients or such special population of patients likely to exhibit lower exposure.

In certain embodiment, the maintenance dose is 9 mg/kg of the antibody and this is administered in two divided doses each containing 4.5 mg/kg of the antibody and the administration interval is two weeks (every 2 weeks). In this case two doses are administered during a month or 4 weeks.

In another embodiment, the maintenance dose is 9 mg/kg of the antibody and this is administered in four divided doses each containing 2.25 mg/kg of the antibody and the administration interval is one week (every week). In this case four doses are administered during a month or 4 weeks.

In certain another embodiment, the maintenance dose is 4.5 mg/kg of the antibody in a single dose and the administration interval is two weeks (every 2 weeks) and in this case two doses are administered during a month or 4 weeks.

In another embodiment, the maintenance dose is 2.25 mg/kg of the antibody in a single dose and the administration interval is one week (every week) and in this case four doses are administered during a month or 4 weeks.

In another aspect, the maintenance dose is 12 mg/kg of the antibody. The maintenance dose of 12 mg/kg refers to, for example, administering total 12 mg/kg of the antibody during 4 weeks or every month in a single dose or multiple divided doses. This can be applicable for pediatric patients or such special population of patients likely to exhibit lower exposure.

In certain embodiment, the maintenance dose is 12 mg/kg of the antibody and this is administered in two divided doses each containing 6 mg/kg of the antibody and the administration interval is two weeks (every 2 weeks). In this case two doses are administered during a month or 4 weeks.

In another embodiment, the maintenance dose is 12 mg/kg of the antibody and this is administered in four divided doses each containing 3 mg/kg of the antibody and the administration interval is one week (every week). In this case four doses are administered during a month or 4 weeks.

In certain embodiment, the maintenance dose is 6 mg/kg of the antibody in a single dose and the administration interval is two weeks (every 2 weeks) and in this case two doses are administered during a month or 4 weeks.

In another embodiment, the maintenance dose is 3 mg/kg of the antibody in a single dose and the administration interval is one week (every week) and in this case four doses are administered during a month or 4 weeks.

In another aspect, a different or alternative maintenance dose and administration interval can be applicable.

In certain embodiments, a different or alternative maintenance dose and administration interval can be applicable after the above-mentioned initial maintenance doses and administration intervals. More specifically, one may modify the above-mentioned every-4-week 6 mg/kg antibody maintenance dosing regimen, every-4-week 9 mg/kg antibody maintenance dosing regimen, and/or every-4-week 12 mg/kg antibody maintenance dosing regimen to apply a different, alternative, or modified maintenance dose and administration interval. For example, after carrying out the administration in any of the above-mentioned every-4-week 6 mg/kg antibody maintenance dosing regimen, every-4-week 9 mg/kg antibody maintenance dosing regimen, and every-4-weeks 12 mg/kg antibody maintenance dosing regimen, one may assess whether the administration of the maintenance dose was sufficient to treat the subject. If the administration of the maintenance dose is turned out to be insufficient or to cause no or insufficient treatment effect and/or preventive effect, then, one may stop administering the maintenance dose of the antibody and start administering a modified maintenance dose. The effect of the administration of the maintenance dose may be assessed at least 1, 2, 3, 4, 5, 6, 7, 8, 9, 10, 11, 12, 16, 20, 24, 36, 48, 60, or more weeks after the start of the administration of the maintenance dose. There is no particular limitation on the number of times that one can change the maintenance dose. The changes of the maintenance dose may be made several times, e.g., once to four times. In other words, one to several, e.g. one to five, different maintenance doses may be applied in a sequential manner, such as (0) administering a maintenance dose, (1) stopping administering the maintenance dose and starting administering a first modified maintenance dose, (2) stopping administering the first modified maintenance dose and starting administering a second modified maintenance dose, (3) stopping administering the second modified maintenance dose and starting administering a third modified maintenance dose, (4) stopping administering the third modified maintenance dose and starting administering a fourth modified maintenance dose.

In some embodiments, the modified maintenance dose may be applied from the beginning, without using the above-mentioned every-4-week 6 mg/kg antibody maintenance dosing regimen, every-4-week 9 mg/kg antibody maintenance dosing regimen, and/or every-4-week 12 mg/kg antibody maintenance dosing regimen.

In certain embodiment, the modified maintenance dose is 6 mg/kg of the antibody. The modified maintenance dose of 6 mg/kg refers to, for example, administering total 6 mg/kg of the antibody during 2 weeks or every 2 weeks as a single dose or multiple divided doses.

In certain embodiment, the modified maintenance dose is 6 mg/kg of the antibody and this is administered in a single dose and the modified administration interval is 2 weeks (every 2 weeks). In this case one single dose is administered during 2 weeks.

In another embodiment, the modified maintenance dose is 6 mg/kg of the antibody and this is administered in two divided doses each containing 3 mg/kg of the antibody and the modified administration interval is one week (every week). In this case two doses are administered during 2 weeks.

In certain embodiment, the modified maintenance dose is 6 mg/kg of the antibody in a single dose and the modified administration interval is two weeks (every 2 weeks) and in this case two doses are administered during a month or 4 weeks, or in other words one single dose is administered during 2 weeks.

In another embodiment, the modified maintenance dose is 3 mg/kg of the antibody in a single dose and the modified administration interval is one week (every week) and in this case two doses are administered during 2 weeks.

In certain embodiment, the modified maintenance dose is 9 mg/kg of the antibody. The modified maintenance dose of 9 mg/kg refers to, for example, administering total 9 mg/kg of the antibody during 2 weeks or every 2 weeks as a single dose or multiple divided doses. This can be applicable for pediatric patients or such special population of patients likely to exhibit lower exposure.

In another embodiment, the modified maintenance dose is 9 mg/kg of the antibody and this is administered in two divided doses each containing 4.5 mg/kg of the antibody and the modified administration interval is one week (every week). In this case two doses are administered during 2 weeks.

In another embodiment, the modified maintenance dose is 4.5 mg/kg of the antibody in a single dose and the modified administration interval is one week (every week) and in this case four doses are administered during a month or 4 weeks, or in other words two doses are administered during 2 weeks.

In certain embodiment, the modified maintenance dose is 12 mg/kg of the antibody. The modified maintenance dose of 12 mg/kg refers to, for example, administering total 12 mg/kg of the antibody during 2 weeks or every 2 weeks as a single dose or multiple divided doses. This can be applicable for pediatric patients or such special population of patients likely to exhibit lower exposure.

In another embodiment, the modified maintenance dose is 12 mg/kg of the antibody and this is administered in two divided doses each containing 6 mg/kg of the antibody and the modified administration interval is one week (every week). In this case two doses are administered during 2 weeks.

In another embodiment with referring to each divided dose above as the modified maintenance dose, the modified maintenance dose is 6 mg/kg of the antibody in a single dose and the modified administration interval is one week (every week) and in this case four doses are administered during a month or 4 weeks, or in other words two doses are administered during 2 weeks.

A "loading" dose herein generally comprises an initial dose of a therapeutic agent administered to a patient, and is followed by one or more maintenance dose(s) thereof. In one aspect, the loading dose refers to the amount given at each individual administration and the administration can be carried out between zero time to 24 times, preferably at least once, at least twice, at least three times, at least four times, or more and preferably twice or four times. Usually, the loading doses are administered at spaced treatment intervals, such as between one week to 4 weeks apart and preferably approximately every week, approximately every 2 weeks, approximately every 3 weeks, or approximately every 4 weeks (every month). In one aspect, the loading dose is between 0.3 mg/kg to 30 mg/kg and preferably 3 mg/kg, 4.5 mg/kg, or 6 mg/kg of the antibody. The loading doses were intended to achieve the steady-state therapeutic plasma concentration as early as possible.

In certain embodiment, the loading dose is 3 mg/kg and the administration interval is one week (every week) and the administration is repeated four times.

In another embodiment, the loading dose is 4.5 mg/kg and the administration interval is one week (every week) and the administration is repeated twice or four times.

In another embodiment, the loading dose is 6 mg/kg and the administration interval is one week (every week) and the administration is repeated four times.

In another embodiment, the loading dose is 6 mg/kg and the administration interval is two weeks (every 2 weeks) and the administration is repeated twice.

The number of times the maintenance dose is administered is not particularly limited, and the number is for example at least once, at least twice, at least three times, at least four times, at least five times, at least six times, at least seven times, at least eight times, at least nine times, at least ten times, at least 15 times, at least 20 times, at least 25 times, at least 35 times, at least 40 times, at least 50 times, at least 60 times, at least 70 times, at least 80 times, at least 90 times, at least 100 times, at least 500 times, at least 1000 times, at least 10000 times, or more.

"Administration interval" (an interval between individual administrations) indicates the interval between administration of the $n^{th}$ loading dose (n is an integer of 1 or greater) and administration of the $(n+1)^{th}$ loading dose, and the interval between administration of the $n^{th}$ maintenance dose (n is an integer of 1 or greater) and administration of the $(n+1)^{th}$ maintenance dose.

In certain embodiment, the antibody is administered as follows.

Regimen A: administration at the loading dose of 3 mg/kg of the antibody once every week for four weeks followed by administration at the maintenance dose of 1.5 mg/kg of the antibody once every week (weekly).

Regimen B: administration at the loading dose of 3 mg/kg of the antibody once every week for four weeks followed by administration at the maintenance dose of 1.5 mg/kg of the antibody once every week (weekly) followed by administration at the modified maintenance dose of 3 mg/kg of the antibody once every week.

Regimen C: administration at the loading dose of 3 mg/kg of the antibody once every week for four weeks followed by administration at the maintenance dose of 1.5 mg/kg of the antibody once every week (weekly) followed by administration at the modified maintenance dose of 6 mg/kg of the antibody once every two weeks.

Regimen D: administration at the loading dose of 3 mg/kg of the antibody once every week for four weeks followed by administration at the maintenance dose of 3 mg/kg of the antibody once every two weeks.

Regimen E: administration at the loading dose of 3 mg/kg of the antibody once every week for four weeks followed by administration at the maintenance dose of 3 mg/kg of the antibody once every two weeks followed by administration at the modified maintenance dose of 3 mg/kg of the antibody once every week.

Regimen F: administration at the loading dose of 3 mg/kg of the antibody once every week for four weeks followed by administration at the maintenance dose of 3 mg/kg of the antibody once every two weeks followed by administration at the modified maintenance dose of 6 mg/kg of the antibody once every two weeks.

Regimen G: administration at the loading dose of 3 mg/kg of the antibody once every week for four weeks followed by administration at the maintenance dose of 6 mg/kg of the antibody once every four weeks (every month).

Regimen H: administration at the loading dose of 3 mg/kg of the antibody once every week for four weeks followed by administration at the maintenance dose of 6 mg/kg of the antibody once every four weeks (every month) followed by administration at the modified maintenance dose of 3 mg/kg of the antibody once every week.

Regimen I: administration at the loading dose of 3 mg/kg of the antibody once every week for four weeks followed by administration at the maintenance dose of 6 mg/kg of the antibody once every four weeks (every month) followed by administration at the modified maintenance dose of 6 mg/kg of the antibody once every two weeks.

Regimen J: administration at the loading dose of 4.5 mg/kg of the antibody once every week for two weeks followed by administration at the maintenance dose of 1.5 mg/kg of the antibody once every week (weekly).

Regimen K: administration at the loading dose of 4.5 mg/kg of the antibody once every week for two weeks followed by administration at the maintenance dose of 1.5 mg/kg of the antibody once every week (weekly) followed by administration at the modified maintenance dose of 3 mg/kg of the antibody once every week.

Regimen L: administration at the loading dose of 4.5 mg/kg of the antibody once every week for two weeks followed by administration at the maintenance dose of 1.5 mg/kg of the antibody once every week (weekly) followed by administration at the modified maintenance dose of 6 mg/kg of the antibody once every two weeks.

Regimen M: administration at the loading dose of 4.5 mg/kg of the antibody once every week for two weeks followed by administration at the maintenance dose of 3 mg/kg of the antibody once every two weeks.

Regimen N: administration at the loading dose of 4.5 mg/kg of the antibody once every week for two weeks followed by administration at the maintenance dose of 3 mg/kg of the antibody once every two weeks followed by administration at the modified maintenance dose of 3 mg/kg of the antibody once every week.

Regimen O: administration at the loading dose of 4.5 mg/kg of the antibody once every week for two weeks followed by administration at the maintenance dose of 3 mg/kg of the antibody once every two weeks followed by administration at the modified maintenance dose of 6 mg/kg of the antibody once every two weeks.

Regimen P: administration at the loading dose of 4.5 mg/kg of the antibody once every week for two weeks followed by administration at the maintenance dose of 6 mg/kg of the antibody once every four weeks (every month).

Regimen Q: administration at the loading dose of 4.5 mg/kg of the antibody once every week for two weeks followed by administration at the maintenance dose of 6 mg/kg of the antibody once every four weeks (every month) followed by administration at the modified maintenance dose of 3 mg/kg of the antibody once every week.

Regimen R: administration at the loading dose of 4.5 mg/kg of the antibody once every week for two weeks followed by administration at the maintenance dose of 6 mg/kg of the antibody once every four weeks (every month) followed by administration at the modified maintenance dose of 6 mg/kg of the antibody once every two weeks.

Regimen S: administration at the loading dose of 6 mg/kg of the antibody once every two weeks for four weeks followed by administration at the maintenance dose of 1.5 mg/kg of the antibody once every week (weekly).

Regimen T: administration at the loading dose of 6 mg/kg of the antibody once every two weeks for four weeks followed by administration at the maintenance dose of 1.5 mg/kg of the antibody once every week (weekly) followed by administration at the modified maintenance dose of 3 mg/kg of the antibody once every week.

Regimen U: administration at the loading dose of 6 mg/kg of the antibody once every two weeks for four weeks followed by administration at the maintenance dose of 1.5 mg/kg of the antibody once every week (weekly) followed by administration at the modified maintenance dose of 6 mg/kg of the antibody once every two weeks.

Regimen V: administration at the loading dose of 6 mg/kg of the antibody once every two weeks for four weeks followed by administration at the maintenance dose of 3 mg/kg of the antibody once every two weeks.

Regimen W: administration at the loading dose of 6 mg/kg of the antibody once every two weeks for four weeks followed by administration at the maintenance dose of 3 mg/kg of the antibody once every two weeks followed by administration at the modified maintenance dose of 3 mg/kg of the antibody once every week.

Regimen X: administration at the loading dose of 6 mg/kg of the antibody once every two weeks for four weeks followed by administration at the maintenance dose of 3 mg/kg of the antibody once every two weeks followed by administration at the modified maintenance dose of 6 mg/kg of the antibody once every two weeks.

Regimen Y: administration at the loading dose of 6 mg/kg of the antibody once every two weeks for four weeks followed by administration at the maintenance dose of 6 mg/kg of the antibody once every four weeks (every month).

Regimen Z: administration at the loading dose of 6 mg/kg of the antibody once every two weeks for four weeks followed by administration at the maintenance dose of 6 mg/kg of the antibody once every four weeks (every month) followed by administration at the modified maintenance dose of 3 mg/kg of the antibody once every week.

Regimen AA: administration at the loading dose of 6 mg/kg of the antibody once every two weeks for four weeks followed by administration at the maintenance dose of 6 mg/kg of the antibody once every four weeks (every month) followed by administration at the modified maintenance dose of 6 mg/kg of the antibody once every two weeks.

Regimen AB: administration at the loading dose of 4.5 mg/kg of the antibody once every week (weekly) for four weeks followed by administration at the maintenance dose of 2.25 mg/kg of the antibody once every week (weekly).

Regimen AC: administration at the loading dose of 4.5 mg/kg of the antibody once every week (weekly) for four weeks followed by administration at the maintenance dose of 2.25 mg/kg of the antibody once every week (weekly) followed by administration at the modified maintenance dose of 4.5 mg/kg of the antibody once every week (weekly).

Regimen AD: administration at the loading dose of 4.5 mg/kg of the antibody once every week (weekly) for four weeks followed by administration at the maintenance dose of 4.5 mg/kg of the antibody once every two weeks.

Regimen AE: administration at the loading dose of 4.5 mg/kg of the antibody once every week (weekly) for four weeks followed by administration at the maintenance dose of 4.5 mg/kg of the antibody once every two weeks followed by administration at the modified maintenance dose of 4.5 mg/kg of the antibody once every week (weekly).

Regimen AF: administration at the loading dose of 6 mg/kg of the antibody once every week (weekly) for four weeks followed by administration at the maintenance dose of 3 mg/kg of the antibody once every week (weekly).

Regimen AG: administration at the loading dose of 6 mg/kg of the antibody once every week (weekly) for four weeks followed by administration at the maintenance dose of 3 mg/kg of the antibody once every week (weekly) followed by administration at the modified maintenance dose of 6 mg/kg of the antibody once every week (weekly).

Regimen AH: administration at the loading dose of 6 mg/kg of the antibody once every week (weekly) for four weeks followed by administration at the maintenance dose of 6 mg/kg of the antibody once every two weeks.

Regimen AI: administration at the loading dose of 6 mg/kg of the antibody once every week (weekly) for four weeks followed by administration at the maintenance dose of 6 mg/kg of the antibody once every two weeks followed by administration at the modified maintenance dose of 6 mg/kg of the antibody once every week (weekly).

Regimen AJ: administration at the loading dose of 4.5 mg/kg of the antibody once every week (weekly) for four weeks followed by administration at the maintenance dose of 2.25 mg/kg of the antibody once every week (weekly) followed by administration at the modified maintenance dose of 9 mg/kg of the antibody once every two weeks.

Regimen AK: administration at the loading dose of 4.5 mg/kg of the antibody once every week (weekly) for four weeks followed by administration at the maintenance dose of 4.5 mg/kg of the antibody once every two weeks followed by administration at the modified maintenance dose of 9 mg/kg of the antibody once every two weeks.

Regimen AL: administration at the loading dose of 4.5 mg/kg of the antibody once every week (weekly) for four weeks followed by administration at the maintenance dose of 9 mg/kg of the antibody once every four weeks (every month).

Regimen AM: administration at the loading dose of 4.5 mg/kg of the antibody once every week (weekly) for four weeks followed by administration at the maintenance dose of 9 mg/kg of the antibody once every four weeks (every month) followed by administration at the modified maintenance dose of 4.5 mg/kg of the antibody once every week (weekly).

Regimen AN: administration at the loading dose of 4.5 mg/kg of the antibody once every week (weekly) for four weeks followed by administration at the maintenance dose of 9 mg/kg of the antibody once every four weeks (every month) followed by administration at the modified maintenance dose of 9 mg/kg of the antibody once every two weeks.

Regimen AO: administration at the loading dose of 6.75 mg/kg of the antibody once every week (weekly) for two weeks followed by administration at the maintenance dose of 2.25 mg/kg of the antibody once every week (weekly).

Regimen AP: administration at the loading dose of 6.75 mg/kg of the antibody once every week (weekly) for two weeks followed by administration at the maintenance dose of 2.25 mg/kg of the antibody once every week (weekly) followed by administration at the modified maintenance dose of 4.5 mg/kg of the antibody once every week (weekly).

Regimen AQ: administration at the loading dose of 6.75 mg/kg of the antibody once every week (weekly) for two weeks followed by administration at the maintenance dose of 2.25 mg/kg of the antibody once every week (weekly) followed by administration at the modified maintenance dose of 9 mg/kg of the antibody once every two weeks.

Regimen AR: administration at the loading dose of 6.75 mg/kg of the antibody once every week (weekly) for two weeks followed by administration at the maintenance dose of 4.5 mg/kg of the antibody once every two weeks.

Regimen AS: administration at the loading dose of 6.75 mg/kg of the antibody once every week (weekly) for two weeks followed by administration at the maintenance dose of 4.5 mg/kg of the antibody once every two weeks followed by administration at the modified maintenance dose of 4.5 mg/kg of the antibody once every week (weekly).

Regimen AT: administration at the loading dose of 6.75 mg/kg of the antibody once every week (weekly) for two weeks followed by administration at the maintenance dose of 4.5 mg/kg of the antibody once every two weeks followed by administration at the modified maintenance dose of 9 mg/kg of the antibody once every two weeks.

Regimen AU: administration at the loading dose of 6.75 mg/kg of the antibody once every week (weekly) for two weeks followed by administration at the maintenance dose of 9 mg/kg of the antibody once every four weeks (every month).

Regimen AV: administration at the loading dose of 6.75 mg/kg of the antibody once every week (weekly) for two weeks followed by administration at the maintenance dose of 9 mg/kg of the antibody once every four weeks (every month) followed by administration at the modified maintenance dose of 4.5 mg/kg of the antibody once every week (weekly).

Regimen AW: administration at the loading dose of 6.75 mg/kg of the antibody once every week (weekly) for two weeks followed by administration at the maintenance dose of 9 mg/kg of the antibody once every four weeks (every month) followed by administration at the modified maintenance dose of 9 mg/kg of the antibody once every two weeks.

Regimen AX: administration at the loading dose of 9 mg/kg of the antibody once every two weeks for four weeks followed by administration at the maintenance dose of 2.25 mg/kg of the antibody once every week (weekly).

Regimen AY: administration at the loading dose of 9 mg/kg of the antibody once every two weeks for four weeks followed by administration at the maintenance dose of 2.25 mg/kg of the antibody once every week (weekly) followed by administration at the modified maintenance dose of 4.5 mg/kg of the antibody once every week (weekly).

Regimen AZ: administration at the loading dose of 9 mg/kg of the antibody once every two weeks for four weeks followed by administration at the maintenance dose of 2.25 mg/kg of the antibody once every week (weekly) followed by administration at the modified maintenance dose of 9 mg/kg of the antibody once every two weeks.

Regimen BA: administration at the loading dose of 9 mg/kg of the antibody once every two weeks for four weeks followed by administration at the maintenance dose of 4.5 mg/kg of the antibody once every two weeks.

Regimen BB: administration at the loading dose of 9 mg/kg of the antibody once every two weeks for four weeks followed by administration at the maintenance dose of 4.5 mg/kg of the antibody once every two weeks followed by administration at the modified maintenance dose of 4.5 mg/kg of the antibody once every week (weekly).

Regimen BC: administration at the loading dose of 9 mg/kg of the antibody once every two weeks for four weeks followed by administration at the maintenance dose of 4.5 mg/kg of the antibody once every two weeks followed by administration at the modified maintenance dose of 9 mg/kg of the antibody once every two weeks.

Regimen BD: administration at the loading dose of 9 mg/kg of the antibody once every two weeks for four weeks followed by administration at the maintenance dose of 9 mg/kg of the antibody once every four weeks (every month).

Regimen BE: administration at the loading dose of 9 mg/kg of the antibody once every two weeks for four weeks followed by administration at the maintenance dose of 9 mg/kg of the antibody once every four weeks (every month) followed by administration at the modified maintenance dose of 4.5 mg/kg of the antibody once every week (weekly).

Regimen BF: administration at the loading dose of 9 mg/kg of the antibody once every two weeks for four weeks followed by administration at the maintenance dose of 9 mg/kg of the antibody once every four weeks (every month) followed by administration at the modified maintenance dose of 9 mg/kg of the antibody once every two weeks.

Regimen BG: administration at the loading dose of 6 mg/kg of the antibody once every week (weekly) for four weeks followed by administration at the maintenance dose of 3 mg/kg of the antibody once every week (weekly) followed by administration at the modified maintenance dose of 12 mg/kg of the antibody once every two weeks.

Regimen BH: administration at the loading dose of 6 mg/kg of the antibody once every week (weekly) for four weeks followed by administration at the maintenance dose of 6 mg/kg of the antibody once every two weeks followed by administration at the modified maintenance dose of 12 mg/kg of the antibody once every two weeks.

Regimen BI: administration at the loading dose of 6 mg/kg of the antibody once every week (weekly) for four weeks followed by administration at the maintenance dose of 12 mg/kg of the antibody once every four weeks (every month).

Regimen BJ: administration at the loading dose of 6 mg/kg of the antibody once every week (weekly) for four weeks followed by administration at the maintenance dose of 12 mg/kg of the antibody once every four weeks (every month) followed by administration at the modified maintenance dose of 6 mg/kg of the antibody once every week (weekly).

Regimen BK: administration at the loading dose of 6 mg/kg of the antibody once every week (weekly) for four weeks followed by administration at the maintenance dose of 12 mg/kg of the antibody once every four weeks (every month) followed by administration at the modified maintenance dose of 12 mg/kg of the antibody once every two weeks.

Regimen BL: administration at the loading dose of 9 mg/kg of the antibody once every week (weekly) for two weeks followed by administration at the maintenance dose of 3 mg/kg of the antibody once every week (weekly).

Regimen BM: administration at the loading dose of 9 mg/kg of the antibody once every week (weekly) for two weeks followed by administration at the maintenance dose of 3 mg/kg of the antibody once every week (weekly) followed by administration at the modified maintenance dose of 6 mg/kg of the antibody once every week (weekly).

Regimen BN: administration at the loading dose of 9 mg/kg of the antibody once every week (weekly) for two weeks followed by administration at the maintenance dose of 3 mg/kg of the antibody once every week (weekly) followed by administration at the modified maintenance dose of 12 mg/kg of the antibody once every two weeks.

Regimen BO: administration at the loading dose of 9 mg/kg of the antibody once every week (weekly) for two weeks followed by administration at the maintenance dose of 6 mg/kg of the antibody once every two weeks.

Regimen BP: administration at the loading dose of 9 mg/kg of the antibody once every week (weekly) for two weeks followed by administration at the maintenance dose of 6 mg/kg of the antibody once every two weeks followed by administration at the modified maintenance dose of 6 mg/kg of the antibody once every week (weekly).

Regimen BQ: administration at the loading dose of 9 mg/kg of the antibody once every week (weekly) for two weeks followed by administration at the maintenance dose of 6 mg/kg of the antibody once every two weeks followed by administration at the modified maintenance dose of 12 mg/kg of the antibody once every two weeks.

Regimen BR: administration at the loading dose of 9 mg/kg of the antibody once every week (weekly) for two weeks followed by administration at the maintenance dose of 12 mg/kg of the antibody once every four weeks (every month).

Regimen BS: administration at the loading dose of 9 mg/kg of the antibody once every week (weekly) for two weeks followed by administration at the maintenance dose of 12 mg/kg of the antibody once every four weeks (every month) followed by administration at the modified maintenance dose of 6 mg/kg of the antibody once every week (weekly).

Regimen BT: administration at the loading dose of 9 mg/kg of the antibody once every week (weekly) for two weeks followed by administration at the maintenance dose of 12 mg/kg of the antibody once every four weeks (every month) followed by administration at the modified maintenance dose of 12 mg/kg of the antibody once every two weeks.

Regimen BU: administration at the loading dose of 12 mg/kg of the antibody once every two weeks for four weeks followed by administration at the maintenance dose of 3 mg/kg of the antibody once every week (weekly).

Regimen BV: administration at the loading dose of 12 mg/kg of the antibody once every two weeks for four weeks followed by administration at the maintenance dose of 3 mg/kg of the antibody once every week (weekly) followed by administration at the modified maintenance dose of 6 mg/kg of the antibody once every week (weekly).

Regimen BW: administration at the loading dose of 12 mg/kg of the antibody once every two weeks for four weeks followed by administration at the maintenance dose of 3 mg/kg of the antibody once every week (weekly) followed by administration at the modified maintenance dose of 12 mg/kg of the antibody once every two weeks.

Regimen BX: administration at the loading dose of 12 mg/kg of the antibody once every two weeks for four weeks followed by administration at the maintenance dose of 6 mg/kg of the antibody once every two weeks.

Regimen BY: administration at the loading dose of 12 mg/kg of the antibody once every two weeks for four weeks followed by administration at the maintenance dose of 6 mg/kg of the antibody once every two weeks followed by administration at the modified maintenance dose of 6 mg/kg of the antibody once every week (weekly).

Regimen BZ: administration at the loading dose of 12 mg/kg of the antibody once every two weeks for four weeks followed by administration at the maintenance dose of 6 mg/kg of the antibody once every two weeks followed by administration at the modified maintenance dose of 12 mg/kg of the antibody once every two weeks.

Regimen CA: administration at the loading dose of 12 mg/kg of the antibody once every two weeks for four weeks followed by administration at the maintenance dose of 12 mg/kg of the antibody once every four weeks (every month).

Regimen CB: administration at the loading dose of 12 mg/kg of the antibody once every two weeks for four weeks followed by administration at the maintenance dose of 12 mg/kg of the antibody once every four weeks (every month) followed by administration at the modified maintenance dose of 6 mg/kg of the antibody once every week (weekly).

Regimen CC: administration at the loading dose of 12 mg/kg of the antibody once every two weeks for four weeks followed by administration at the maintenance dose of 12 mg/kg of the antibody once every four weeks (every month) followed by administration at the modified maintenance dose of 12 mg/kg of the antibody once every two weeks.

Regimen CD: administration at the maintenance dose of 3 mg/kg of the antibody once every week (weekly).

Regimen CE: administration at the maintenance dose of 3 mg/kg of the antibody once every week (weekly) followed by administration at the modified maintenance dose of 4.5 mg/kg of the antibody once every week (weekly).

Regimen CF: administration at the maintenance dose of 3 mg/kg of the antibody once every week (weekly) followed by administration at the modified maintenance dose of 9 mg/kg of the antibody once every two weeks.

Regimen CG: administration at the maintenance dose of 3 mg/kg of the antibody once every week (weekly) followed by administration at the first modified maintenance dose of 4.5 mg/kg of the antibody once every week (weekly) followed by administration at the second modified maintenance dose of 6 mg/kg of the antibody once every week (weekly).

Regimen CH: administration at the maintenance dose of 3 mg/kg of the antibody once every week (weekly) followed by administration at the first modified maintenance dose of 4.5 mg/kg of the antibody once every week (weekly) followed by administration at the second modified maintenance dose of 12 mg/kg of the antibody once every two weeks.

Regimen CI: administration at the maintenance dose of 3 mg/kg of the antibody once every week (weekly) followed by administration at the first modified maintenance dose of 9 mg/kg of the antibody once every two weeks followed by administration at the second modified maintenance dose of 6 mg/kg of the antibody once every week (weekly).

Regimen CJ: administration at the maintenance dose of 3 mg/kg of the antibody once every week (weekly) followed by administration at the first modified maintenance dose of 9 mg/kg of the antibody once every two weeks followed by administration at the second modified maintenance dose of 12 mg/kg of the antibody once every two weeks.

Regimen CK: administration at the maintenance dose of 3 mg/kg of the antibody once every week (weekly) followed by administration at the modified maintenance dose of 6 mg/kg of the antibody once every week (weekly).

Regimen CL: administration at the maintenance dose of 3 mg/kg of the antibody once every week (weekly) followed by administration at the modified maintenance dose of 12 mg/kg of the antibody once every two weeks.

Regimen CM: administration at the maintenance dose of 6 mg/kg of the antibody once every two weeks.

Regimen CN: administration at the maintenance dose of 6 mg/kg of the antibody once every two weeks followed by administration at the modified maintenance dose of 4.5 mg/kg of the antibody once every week (weekly).

Regimen CO: administration at the maintenance dose of 6 mg/kg of the antibody once every two weeks followed by administration at the modified maintenance dose of 9 mg/kg of the antibody once every two weeks.

Regimen CP: administration at the maintenance dose of 6 mg/kg of the antibody once every two weeks followed by administration at the first modified maintenance dose of 4.5 mg/kg of the antibody once every week (weekly) followed by administration at the second modified maintenance dose of 6 mg/kg of the antibody once every week (weekly).

Regimen CQ: administration at the maintenance dose of 6 mg/kg of the antibody once every two weeks followed by administration at the first modified maintenance dose of 4.5 mg/kg of the antibody once every week (weekly) followed by administration at the second modified maintenance dose of 12 mg/kg of the antibody once every two weeks.

Regimen CR: administration at the maintenance dose of 6 mg/kg of the antibody once every two weeks followed by administration at the first modified maintenance dose of 9 mg/kg of the antibody once every two weeks followed by administration at the second modified maintenance dose of 6 mg/kg of the antibody once every week (weekly).

Regimen CS: administration at the maintenance dose of 6 mg/kg of the antibody once every two weeks followed by administration at the first modified maintenance dose of 9 mg/kg of the antibody once every two weeks followed by administration at the second modified maintenance dose of 12 mg/kg of the antibody once every two weeks.

Regimen CT: administration at the maintenance dose of 6 mg/kg of the antibody once every two weeks followed by administration at the modified maintenance dose of 6 mg/kg of the antibody once every week (weekly).

Regimen CU: administration at the maintenance dose of 6 mg/kg of the antibody once every two weeks followed by administration at the modified maintenance dose of 12 mg/kg of the antibody once every two weeks.

Regimen CV: administration at the maintenance dose of 12 mg/kg of the antibody once every four weeks (every month).

Regimen CW: administration at the maintenance dose of 12 mg/kg of the antibody once every four weeks (every month) followed by administration at the modified maintenance dose of 4.5 mg/kg of the antibody once every week (weekly).

Regimen CX: administration at the maintenance dose of 12 mg/kg of the antibody once every four weeks (every month) followed by administration at the modified maintenance dose of 9 mg/kg of the antibody once every two weeks.

Regimen CY: administration at the maintenance dose of 12 mg/kg of the antibody once every four weeks (every month) followed by administration at the first modified maintenance dose of 4.5 mg/kg of the antibody once every week (weekly) followed by administration at the second modified maintenance dose of 6 mg/kg of the antibody once every week (weekly).

Regimen CZ: administration at the maintenance dose of 12 mg/kg of the antibody once every four weeks (every month) followed by administration at the first modified maintenance dose of 4.5 mg/kg of the antibody once every week (weekly) followed by administration at the second modified maintenance dose of 12 mg/kg of the antibody once every two weeks.

Regimen DA: administration at the maintenance dose of 12 mg/kg of the antibody once every four weeks (every month) followed by administration at the first modified maintenance dose of 9 mg/kg of the antibody once every two weeks followed by administration at the second modified maintenance dose of 6 mg/kg of the antibody once every week (weekly).

Regimen DB: administration at the maintenance dose of 12 mg/kg of the antibody once every four weeks (every month) followed by administration at the first modified maintenance dose of 9 mg/kg of the antibody once every two weeks followed by administration at the second modified maintenance dose of 12 mg/kg of the antibody once every two weeks.

Regimen DC: administration at the maintenance dose of 12 mg/kg of the antibody once every four weeks (every month) followed by administration at the modified maintenance dose of 6 mg/kg of the antibody once every week (weekly).

Regimen DD: administration at the maintenance dose of 12 mg/kg of the antibody once every four weeks (every month) followed by administration at the modified maintenance dose of 12 mg/kg of the antibody once every two weeks.

Regimen DE: administration at the maintenance dose of 4.5 mg/kg of the antibody once every week (weekly).

Regimen DF: administration at the maintenance dose of 4.5 mg/kg of the antibody once every week (weekly) followed by administration at the modified maintenance dose of 6 mg/kg of the antibody once every week (weekly).

Regimen DG: administration at the maintenance dose of 4.5 mg/kg of the antibody once every week (weekly) followed by administration at the modified maintenance dose of 12 mg/kg of the antibody once every two weeks.

Regimen DH: administration at the maintenance dose of 9 mg/kg of the antibody once every two weeks.

Regimen DI: administration at the maintenance dose of 9 mg/kg of the antibody once every two weeks followed by administration at the modified maintenance dose of 6 mg/kg of the antibody once every week (weekly).

Regimen DJ: administration at the maintenance dose of 9 mg/kg of the antibody once every two weeks followed by administration at the modified maintenance dose of 12 mg/kg of the antibody once every two weeks.

Regimen DK: administration at the maintenance dose of 6 mg/kg of the antibody once every week (weekly).

Regimen DL: administration at the maintenance dose of 12 mg/kg of the antibody once every two weeks.

Regimen DM: administration at the loading dose of 3 mg/kg of the antibody once every week (weekly) for four weeks followed by administration at the maintenance dose of 1.5 mg/kg of the antibody once every week (weekly) followed by administration at the modified maintenance dose of 2.25 mg/kg of the antibody once every week (weekly).

Regimen DN: administration at the loading dose of 3 mg/kg of the antibody once every week (weekly) for four weeks followed by administration at the maintenance dose of 1.5 mg/kg of the antibody once every week (weekly) followed by administration at the first modified maintenance dose of 2.25 mg/kg of the antibody once every week (weekly) followed by administration at the second modified maintenance dose of 3 mg/kg of the antibody once every week (weekly).

Regimen DO: administration at the loading dose of 3 mg/kg of the antibody once every week (weekly) for four weeks followed by administration at the maintenance dose of 1.5 mg/kg of the antibody once every week (weekly) followed by administration at the first modified maintenance dose of 2.25 mg/kg of the antibody once every week (weekly) followed by administration at the second modified maintenance dose of 3 mg/kg of the antibody once every week (weekly) followed by administration at the third modified maintenance dose of 4.5 mg/kg of the antibody once every week (weekly).

Regimen DP: administration at the loading dose of 3 mg/kg of the antibody once every week (weekly) for four weeks followed by administration at the maintenance dose of 1.5 mg/kg of the antibody once every week (weekly) followed by administration at the first modified maintenance dose of 2.25 mg/kg of the antibody once every week (weekly) followed by administration at the second modified maintenance dose of 3 mg/kg of the antibody once every week (weekly) followed by administration at the third modified maintenance dose of 4.5 mg/kg of the antibody once every week (weekly) followed by administration at the fourth modified maintenance dose of 6 mg/kg of the antibody once every week (weekly).

Regimen DQ: administration at the loading dose of 3 mg/kg of the antibody once every week (weekly) for four weeks followed by administration at the maintenance dose of 1.5 mg/kg of the antibody once every week (weekly) followed by administration at the first modified maintenance dose of 2.25 mg/kg of the antibody once every week (weekly) followed by administration at the second modified maintenance dose of 3 mg/kg of the antibody once every week (weekly) followed by administration at the third modified maintenance dose of 6 mg/kg of the antibody once every week (weekly).

Regimen DR: administration at the loading dose of 3 mg/kg of the antibody once every week (weekly) for four weeks followed by administration at the maintenance dose of 1.5 mg/kg of the antibody once every week (weekly) followed by administration at the first modified maintenance dose of 2.25 mg/kg of the antibody once every week (weekly) followed by administration at the second modified maintenance dose of 4.5 mg/kg of the antibody once every week (weekly).

Regimen DS: administration at the loading dose of 3 mg/kg of the antibody once every week (weekly) for four weeks followed by administration at the maintenance dose of 1.5 mg/kg of the antibody once every week (weekly) followed by administration at the first modified maintenance dose of 2.25 mg/kg of the antibody once every week (weekly) followed by administration at the second modified maintenance dose of 4.5 mg/kg of the antibody once every week (weekly) followed by administration at the third modified maintenance dose of 6 mg/kg of the antibody once every week (weekly).

Regimen DT: administration at the loading dose of 3 mg/kg of the antibody once every week (weekly) for four weeks followed by administration at the maintenance dose of 1.5 mg/kg of the antibody once every week (weekly) followed by administration at the first modified maintenance dose of 3 mg/kg of the antibody once every week (weekly) followed by administration at the second modified maintenance dose of 4.5 mg/kg of the antibody once every week (weekly).

Regimen DU: administration at the loading dose of 3 mg/kg of the antibody once every week (weekly) for four weeks followed by administration at the maintenance dose of 1.5 mg/kg of the antibody once every week (weekly) followed by administration at the first modified maintenance dose of 3 mg/kg of the antibody once every week (weekly) followed by administration at the second modified maintenance dose of 4.5 mg/kg of the antibody once every week (weekly) followed by administration at the third modified maintenance dose of 6 mg/kg of the antibody once every week (weekly).

Regimen DV: administration at the loading dose of 3 mg/kg of the antibody once every week (weekly) for four weeks followed by administration at the maintenance dose of 1.5 mg/kg of the antibody once every week (weekly) followed by administration at the first modified maintenance dose of 3 mg/kg of the antibody once every week (weekly) followed by administration at the second modified maintenance dose of 6 mg/kg of the antibody once every week (weekly).

Regimen DW: administration at the loading dose of 3 mg/kg of the antibody once every week (weekly) for four weeks followed by administration at the maintenance dose of 2.25 mg/kg of the antibody once every week (weekly).

Regimen DX: administration at the loading dose of 3 mg/kg of the antibody once every week (weekly) for four weeks followed by administration at the maintenance dose of 2.25 mg/kg of the antibody once every week (weekly) followed by administration at the modified maintenance dose of 3 mg/kg of the antibody once every week (weekly).

Regimen DY: administration at the loading dose of 3 mg/kg of the antibody once every week (weekly) for four weeks followed by administration at the maintenance dose of 2.25 mg/kg of the antibody once every week (weekly) followed by administration at the first modified maintenance dose of 3 mg/kg of the antibody once every week (weekly) followed by administration at the second modified maintenance dose of 4.5 mg/kg of the antibody once every week (weekly).

Regimen DZ: administration at the loading dose of 3 mg/kg of the antibody once every week (weekly) for four weeks followed by administration at the maintenance dose of 2.25 mg/kg of the antibody once every week (weekly) followed by administration at the first modified maintenance dose of 3 mg/kg of the antibody once every week (weekly) followed by administration at the second modified maintenance dose of 4.5 mg/kg of the antibody once every week (weekly) followed by administration at the third modified maintenance dose of 6 mg/kg of the antibody once every week (weekly).

Regimen EA: administration at the loading dose of 3 mg/kg of the antibody once every week (weekly) for four weeks followed by administration at the maintenance dose of 2.25 mg/kg of the antibody once every week (weekly) followed by administration at the first modified maintenance dose of 3 mg/kg of the antibody once every week (weekly) followed by administration at the second modified maintenance dose of 6 mg/kg of the antibody once every week (weekly).

Regimen EB: administration at the loading dose of 3 mg/kg of the antibody once every week (weekly) for four weeks followed by administration at the maintenance dose of 2.25 mg/kg of the antibody once every week (weekly) followed by administration at the modified maintenance dose of 4.5 mg/kg of the antibody once every week (weekly).

Regimen EC: administration at the loading dose of 3 mg/kg of the antibody once every week (weekly) for four weeks followed by administration at the maintenance dose of 2.25 mg/kg of the antibody once every week (weekly) followed by administration at the first modified maintenance dose of 4.5 mg/kg of the antibody once every week (weekly) followed by administration at the second modified maintenance dose of 6 mg/kg of the antibody once every week (weekly).

Regimen ED: (I) administration at the loading dose of (I-i) 3 mg/kg of the antibody once every week (weekly) for four weeks, (I-ii) 4.5 mg/kg of the antibody once every week (weekly) for two weeks, or (I-iii) 6 mg/kg of the antibody once every two weeks for four weeks, followed by (II) administration at the maintenance dose of (II-i) 1.5 mg/kg of the antibody once every week (weekly), (II-ii) 3 mg/kg of the antibody once every two weeks, or (II-iii) 6 mg/kg of the antibody once every four weeks (every month), followed by (III) administration at the modified maintenance dose of (III-i) 2.25 mg/kg of the antibody once every week (weekly), (III-ii) 4.5 mg/kg of the antibody once every two weeks, or (III-iii) 9 mg/kg of the antibody once every four weeks (every month).

Regimen EE: (I) administration at the loading dose of (I-i) 3 mg/kg of the antibody once every week (weekly) for four weeks, (I-ii) 4.5 mg/kg of the antibody once every week (weekly) for two weeks, or (I-iii) 6 mg/kg of the antibody once every two weeks for four weeks, followed by (II) administration at the maintenance dose of (II-i) 1.5 mg/kg of the antibody once every week (weekly), (II-ii) 3 mg/kg of the antibody once every two weeks, or (II-iii) 6 mg/kg of the antibody once every four weeks (every month), followed by (III) administration at the first modified maintenance dose of (III-i) 2.25 mg/kg of the antibody once every week (weekly), (III-ii) 4.5 mg/kg of the antibody once every two weeks, or (III-iii) 9 mg/kg of the antibody once every four weeks (every month), followed by (IV) administration at the second modified maintenance dose of (IV-i) 3 mg/kg of the antibody once every week (weekly), (IV-ii) 6 mg/kg of the antibody once every two weeks, or (IV-iii) 12 mg/kg of the antibody once every four weeks (every month).

Regimen EF: (I) administration at the loading dose of (I-i) 3 mg/kg of the antibody once every week (weekly) for four weeks, (I-ii) 4.5 mg/kg of the antibody once every week (weekly) for two weeks, or (I-iii) 6 mg/kg of the antibody once every two weeks for four weeks, followed by (II) administration at the maintenance dose of (II-i) 1.5 mg/kg of the antibody once every week (weekly), (II-ii) 3 mg/kg of the antibody once every two weeks, or (II-iii) 6 mg/kg of the antibody once every four weeks (every month), followed by (III) administration at the first modified maintenance dose of (III-i) 2.25 mg/kg of the antibody once every week (weekly), (III-ii) 4.5 mg/kg of the antibody once every two weeks, or (III-iii) 9 mg/kg of the antibody once every four weeks (every month), followed by (IV) administration at the second modified maintenance dose of (IV-i) 3 mg/kg of the antibody once every week (weekly), (IV-ii) 6 mg/kg of the antibody once every two weeks, or (IV-iii) 12 mg/kg of the antibody once every four weeks (every month), followed by (V) administration at the third modified maintenance dose of (V-i) 4.5 mg/kg of the antibody once every week (weekly), or (V-ii) 9 mg/kg of the antibody once every two weeks.

Regimen EG: (I) administration at the loading dose of (I-i) 3 mg/kg of the antibody once every week (weekly) for four weeks, (I-ii) 4.5 mg/kg of the antibody once every week (weekly) for two weeks, or (I-iii) 6 mg/kg of the antibody once every two weeks for four weeks, followed by (II) administration at the maintenance dose of (II-i) 1.5 mg/kg of the antibody once every week (weekly), (II-ii) 3 mg/kg of the antibody once every two weeks, or (II-iii) 6 mg/kg of the antibody once every four weeks (every month), followed by (III) administration at the first modified maintenance dose of (III-i) 2.25 mg/kg of the antibody once every week (weekly), (III-ii) 4.5 mg/kg of the antibody once every two weeks, or (III-iii) 9 mg/kg of the antibody once every four weeks (every month), followed by (IV) administration at the second modified maintenance dose of (IV-i) 3 mg/kg of the antibody once every week (weekly), (IV-ii) 6 mg/kg of the antibody once every two weeks, or (IV-iii) 12 mg/kg of the antibody once every four weeks (every month), followed by (V) administration at the third modified maintenance dose of (V-i) 4.5 mg/kg of the antibody once every week (weekly), or (V-ii) 9 mg/kg of the antibody once every two weeks, followed by (VI) administration at the fourth modified maintenance dose of (VI-i) 6 mg/kg of the antibody once every week (weekly), or (VI-ii) 12 mg/kg of the antibody once every two weeks.

Regimen EH: (I) administration at the loading dose of (I-i) 3 mg/kg of the antibody once every week (weekly) for four weeks, (I-ii) 4.5 mg/kg of the antibody once every week (weekly) for two weeks, or (I-iii) 6 mg/kg of the antibody once every two weeks for four weeks, followed by (II) administration at the maintenance dose of (II-i) 1.5 mg/kg of the antibody once every week (weekly), (II-ii) 3 mg/kg of the antibody once every two weeks, or (II-iii) 6 mg/kg of the antibody once every four weeks (every month), followed by (III) administration at the first modified maintenance dose of (III-i) 2.25 mg/kg of the antibody once every week (weekly), (III-ii) 4.5 mg/kg of the antibody once every two weeks, or (III-iii) 9 mg/kg of the antibody once every four weeks (every month), followed by (IV) administration at the second modified maintenance dose of (IV-i) 3 mg/kg of the antibody once every week (weekly), (IV-ii) 6 mg/kg of the antibody once every two weeks, or (IV-iii) 12 mg/kg of the antibody once every four weeks (every month), followed by (V) administration at the third modified maintenance dose of (V-i) 6 mg/kg of the antibody once every week (weekly), or (V-ii) 12 mg/kg of the antibody once every two weeks.

Regimen EI: (I) administration at the loading dose of (I-i) 3 mg/kg of the antibody once every week (weekly) for four weeks, (I-ii) 4.5 mg/kg of the antibody once every week (weekly) for two weeks, or (I-iii) 6 mg/kg of the antibody once every two weeks for four weeks, followed by (II) administration at the maintenance dose of (II-i) 1.5 mg/kg of the antibody once every week (weekly), (II-ii) 3 mg/kg of the antibody once every two weeks, or (II-iii) 6 mg/kg of the antibody once every four weeks (every month), followed by (III) administration at the first modified maintenance dose of (III-i) 2.25 mg/kg of the antibody once every week (weekly), (III-ii) 4.5 mg/kg of the antibody once every two weeks, or (III-iii) 9 mg/kg of the antibody once every four weeks (every month), followed by (IV) administration at the second modified maintenance dose of (IV-i) 4.5 mg/kg of the antibody once every week (weekly), or (IV-ii) 9 mg/kg of the antibody once every two weeks.

Regimen EJ: (I) administration at the loading dose of (I-i) 3 mg/kg of the antibody once every week (weekly) for four weeks, (I-ii) 4.5 mg/kg of the antibody once every week (weekly) for two weeks, or (I-iii) 6 mg/kg of the antibody once every two weeks for four weeks, followed by (II) administration at the maintenance dose of (II-i) 1.5 mg/kg of the antibody once every week (weekly), (II-ii) 3 mg/kg of the antibody once every two weeks, or (II-iii) 6 mg/kg of the antibody once every four weeks (every month), followed by (III) administration at the first modified maintenance dose of (III-i) 2.25 mg/kg of the antibody once every week (weekly), (III-ii) 4.5 mg/kg of the antibody once every two weeks, or (III-iii) 9 mg/kg of the antibody once every four weeks (every month), followed by (IV) administration at the second modified maintenance dose of (IV-i) 4.5 mg/kg of the antibody once every week (weekly), or (IV-ii) 9 mg/kg of the antibody once every two weeks, followed by (V) administration at the third modified maintenance dose of (V-i) 6 mg/kg of the antibody once every week (weekly), or (V-ii) 12 mg/kg of the antibody once every two weeks.

Regimen EK: (I) administration at the loading dose of (I-i) 3 mg/kg of the antibody once every week (weekly) for four weeks, (I-ii) 4.5 mg/kg of the antibody once every week (weekly) for two weeks, or (I-iii) 6 mg/kg of the antibody once every two weeks for four weeks, followed by (II) administration at the maintenance dose of (II-i) 1.5 mg/kg of the antibody once every week (weekly), (II-ii) 3 mg/kg of the antibody once every two weeks, or (II-iii) 6 mg/kg of the antibody once every four weeks (every month), followed by (III) administration at the first modified maintenance dose of (III-i) 3 mg/kg of the antibody once every week (weekly), (III-ii) 6 mg/kg of the antibody once every two weeks, or (III-iii) 12 mg/kg of the antibody once every four weeks (every month), followed by (IV) administration at the second modified maintenance dose of (IV-i) 4.5 mg/kg of the antibody once every week (weekly), or (IV-ii) 9 mg/kg of the antibody once every two weeks.

Regimen EL: (I) administration at the loading dose of (I-i) 3 mg/kg of the antibody once every week (weekly) for four weeks, (I-ii) 4.5 mg/kg of the antibody once every week (weekly) for two weeks, or (I-iii) 6 mg/kg of the antibody once every two weeks for four weeks, followed by (II) administration at the maintenance dose of (II-i) 1.5 mg/kg of the antibody once every week (weekly), (II-ii) 3 mg/kg of the antibody once every two weeks, or (II-iii) 6 mg/kg of the antibody once every four weeks (every month), followed by (III) administration at the first modified maintenance dose of (III-i) 3 mg/kg of the antibody once every week (weekly), (III-ii) 6 mg/kg of the antibody once every two weeks, or (III-iii) 12 mg/kg of the antibody once every four weeks (every month), followed by (IV) administration at the second modified maintenance dose of (IV-i) 4.5 mg/kg of the antibody once every week (weekly), or (IV-ii) 9 mg/kg of the antibody once every two weeks, followed by (V) administration at the third modified maintenance dose of (V-i) 6 mg/kg of the antibody once every week (weekly), or (V-ii) 12 mg/kg of the antibody once every two weeks.

Regimen EM: (I) administration at the loading dose of (I-i) 3 mg/kg of the antibody once every week (weekly) for four weeks, (I-ii) 4.5 mg/kg of the antibody once every week (weekly) for two weeks, or (I-iii) 6 mg/kg of the antibody once every two weeks for four weeks, followed by (II) administration at the maintenance dose of (II-i) 1.5 mg/kg of the antibody once every week (weekly), (II-ii) 3 mg/kg of the antibody once every two weeks, or (II-iii) 6 mg/kg of the antibody once every four weeks (every month), followed by (III) administration at the first modified maintenance dose of (III-i) 3 mg/kg of the antibody once every week (weekly), (III-ii) 6 mg/kg of the antibody once every two weeks, or (III-iii) 12 mg/kg of the antibody once every four weeks (every month), followed by (IV) administration at the second modified maintenance dose of (IV-i) 6 mg/kg of the antibody once every week (weekly), or (IV-ii) 12 mg/kg of the antibody once every two weeks.

Regimen EN: (I) administration at the loading dose of (I-i) 3 mg/kg of the antibody once every week (weekly) for four weeks, (I-ii) 4.5 mg/kg of the antibody once every week (weekly) for two weeks, or (I-iii) 6 mg/kg of the antibody once every two weeks for four weeks, followed by (II) administration at the maintenance dose of (II-i) 2.25 mg/kg of the antibody once every week (weekly), (II-ii) 4.5 mg/kg of the antibody once every two weeks, or (II-iii) 9 mg/kg of the antibody once every four weeks (every month).

Regimen EO: (I) administration at the loading dose of (I-i) 3 mg/kg of the antibody once every week (weekly) for four weeks, (I-ii) 4.5 mg/kg of the antibody once every week (weekly) for two weeks, or (I-iii) 6 mg/kg of the antibody once every two weeks for four weeks, followed by (II) administration at the maintenance dose of (II-i) 2.25 mg/kg of the antibody once every week (weekly), (II-ii) 4.5 mg/kg of the antibody once every two weeks, or (II-iii) 9 mg/kg of the antibody once every four weeks (every month), followed by (III) administration at the modified maintenance dose of (III-i) 3 mg/kg of the antibody once every week (weekly), (III-ii) 6 mg/kg of the antibody once every two weeks, or (III-iii) 12 mg/kg of the antibody once every four weeks (every month).

Regimen EP: (I) administration at the loading dose of (I-i) 3 mg/kg of the antibody once every week (weekly) for four weeks, (I-ii) 4.5 mg/kg of the antibody once every week (weekly) for two weeks, or (I-iii) 6 mg/kg of the antibody once every two weeks for four weeks, followed by (II) administration at the maintenance dose of (II-i) 2.25 mg/kg of the antibody once every week (weekly), (II-ii) 4.5 mg/kg of the antibody once every two weeks, or (II-iii) 9 mg/kg of the antibody once every four weeks (every month), followed by (III) administration at the first modified maintenance dose of (III-i) 3 mg/kg of the antibody once every week (weekly), (III-ii) 6 mg/kg of the antibody once every two weeks, or (III-iii) 12 mg/kg of the antibody once every four weeks (every month), followed by (IV) administration at the second modified maintenance dose of (IV-i) 4.5 mg/kg of the antibody once every week (weekly), or (IV-ii) 9 mg/kg of the antibody once every two weeks.

Regimen EQ: (I) administration at the loading dose of (I-i) 3 mg/kg of the antibody once every week (weekly) for four weeks, (I-ii) 4.5 mg/kg of the antibody once every week (weekly) for two weeks, or (I-iii) 6 mg/kg of the antibody once every two weeks for four weeks, followed by (II) administration at the maintenance dose of (II-i) 2.25 mg/kg of the antibody once every week (weekly), (II-ii) 4.5 mg/kg of the antibody once every two weeks, or (II-iii) 9 mg/kg of the antibody once every four weeks (every month), followed by (III) administration at the first modified maintenance dose of (III-i) 3 mg/kg of the antibody once every week (weekly), (III-ii) 6 mg/kg of the antibody once every two weeks, or (III-iii) 12 mg/kg of the antibody once every four weeks (every month), followed by (IV) administration at the second modified maintenance dose of (IV-i) 4.5 mg/kg of the antibody once every week (weekly), or (IV-ii) 9 mg/kg of the antibody once every two weeks, followed by (V) administration at the third modified maintenance dose of (V-i) 6 mg/kg of the antibody once every week (weekly), or (V-ii) 12 mg/kg of the antibody once every two weeks.

Regimen ER: (I) administration at the loading dose of (I-i) 3 mg/kg of the antibody once every week (weekly) for four weeks, (I-ii) 4.5 mg/kg of the antibody once every week (weekly) for two weeks, or (I-iii) 6 mg/kg of the antibody once every two weeks for four weeks, followed by (II) administration at the maintenance dose of (II-i) 2.25 mg/kg of the antibody once every week (weekly), (II-ii) 4.5 mg/kg of the antibody once every two weeks, or (II-iii) 9 mg/kg of the antibody once every four weeks (every month), followed by (III) administration at the first modified maintenance dose of (III-i) 3 mg/kg of the antibody once every week (weekly), (III-ii) 6 mg/kg of the antibody once every two weeks, or (III-iii) 12 mg/kg of the antibody once every four weeks (every month), followed by (IV) administration at the second modified maintenance dose of (IV-i) 6 mg/kg of the antibody once every week (weekly), or (IV-ii) 12 mg/kg of the antibody once every two weeks.

Regimen ES: (I) administration at the loading dose of (I-i) 3 mg/kg of the antibody once every week (weekly) for four weeks, (I-ii) 4.5 mg/kg of the antibody once every week (weekly) for two weeks, or (I-iii) 6 mg/kg of the antibody once every two weeks for four weeks, followed by (II) administration at the maintenance dose of (II-i) 2.25 mg/kg of the antibody once every week (weekly), (II-ii) 4.5 mg/kg of the antibody once every two weeks, or (II-iii) 9 mg/kg of the antibody once every four weeks (every month), followed by (III) administration at the modified maintenance dose of (III-i) 4.5 mg/kg of the antibody once every week (weekly), or (III-ii) 9 mg/kg of the antibody once every two weeks.

Regimen ET: (I) administration at the loading dose of (I-i) 3 mg/kg of the antibody once every week (weekly) for four weeks, (I-ii) 4.5 mg/kg of the antibody once every week (weekly) for two weeks, or (I-iii) 6 mg/kg of the antibody once every two weeks for four weeks, followed by (II) administration at the maintenance dose of (II-i) 2.25 mg/kg of the antibody once every week (weekly), (II-ii) 4.5 mg/kg of the antibody once every two weeks, or (II-iii) 9 mg/kg of the antibody once every four weeks (every month), followed by (III) administration at the first modified maintenance dose of (III-i) 4.5 mg/kg of the antibody once every week (weekly), or (III-ii) 9 mg/kg of the antibody once every two weeks, followed by (IV) administration at the second modified maintenance dose of (IV-i) 6 mg/kg of the antibody once every week (weekly), or (IV-ii) 12 mg/kg of the antibody once every two weeks.

In some embodiments, regimens of the invention can be applicable for patients who suffer from bleeding, or excessive bleeding. The regimens of the invention can be applicable in a method for preventing and/or treating bleeding in such patients, or for increasing blood clotting activity in such patients, or for reducing excessive bleeding in such patients. Here, "preventing" or "treating" bleeding refers to reducing the incidence of bleeding or reducing the likelihood of bleeding in a patient. In certain embodiments, excessive bleeding in such patients is caused by a decrease or deficiency in the activity of FVIII and/or FVIIIa. In a certain embodiment, patents who suffer from bleeding have hemophilia, which may be hemophilia A or severe hemophilia A.

In some embodiments, regimens of the invention can be applicable for patients with hemophilia A and preferably patients with hemophilia A having FVIII inhibitors and/or patients with hemophilia A not having FVIII inhibitors.

In some embodiment, regimens of the invention can be applicable for patients with severe hemophilia A.

In some embodiments, regimens of the invention can be applicable for adult patients, and/or pediatric patients and/or such special population of patients likely to exhibit lower exposure.

The dosage regimen is determined, for example, by considering the effects and safety. Furthermore, the dosage regimen is determined by considering the convenience of the patient, within the range that does not impair the effectiveness and safety. For example, the dosage regimen for a hemophilia A patient can be determined by considering the effects of preventing bleeding in patients and clinically acceptable safety.

A disease accompanying bleeding or a disease caused by bleeding may include a disease that develops and/or progresses due to a decrease or deficiency in the activity of FVIII and/or FVIIIa.

A disease that develops and/or progresses due to a decrease or deficiency in the activity of FVIII and/or FVIIIa is, for example, hemophilia A, hemophilia A with emergence of an inhibitor against FVIII/FVIIIa, acquired hemophilia A, and von Willebrand disease, but the disease is not particularly limited thereto.

In some embodiments, regimens of the invention can be applicable for preventing bleeding episodes and reducing the frequency of bleeding episodes in congenital FVlll-deficient patients with inhibitors.

In some embodiments, regimens of the invention can be applicable for preventing bleeding episodes and reducing the frequency of bleeding episodes in congenital FVlll-deficient patients without inhibitors.

In some embodiments, regimens of the invention can be applicable for preventing bleeding episodes and reducing the frequency of bleeding episodes in acquired FVlll-deficient patients with inhibitors.

In some embodiments, regimens of the invention can be applicable for preventing bleeding episodes and reducing the frequency of bleeding episodes in acquired FVlll-deficient patients without inhibitors.

In some embodiments, regimens of the invention can be applicable for preventing bleeding episodes and reducing the frequency of bleeding episodes in congenital von Willebrand factor-deficient patients.

In some embodiments, regimens of the invention can be applicable for preventing bleeding episodes and reducing the frequency of bleeding episodes in acquired von Willebrand factor-deficient patients.

The term "inhibitor patient" as used herein refers to a patient with hemophilia A having FVIII inhibitors.

The term "non-inhibitor patient" as used herein refers to a patient with hemophilia A not having FVIII inhibitors.

The present invention provides a product comprising at least (i) a container; (ii) a pharmaceutical composition in a container, which comprises a bispecific antigen-binding molecule that recognizes (a) FIX and/or FIXa and (b) FX and/or FXa; and (iii) a document instructing administration of the antigen-binding molecule according to any one of the dosing regimens described above. In addition, a label, syringe, syringe needle, pharmaceutically acceptable medium, alcohol-soaked cotton, adhesive bandage, and such may be packaged in the product. The container is, for example, a bottle, a glass bottle, or a syringe, and can be produced from various materials such as glass or plastic. Administration-supporting devices may be attached to the product. A pharmaceutical composition is stored in the container, and the mouth of the container is sealed with a rubber stopper or such. For example, a label indicating that the pharmaceutical composition is to be used for preventing or treating selected pathological conditions is attached to the container. The document of (iii) may include instructions that specify the loading dose, maintenance dose, administration frequency or intervals, according to the dosing regimens as described above.

Treatment of hemophilia refers to, for example, stopping bleeding by administering the composition to a hemophilia patient who is actually showing bleeding symptoms (treatment of bleeding) and/or reducing the bleeding frequency by administering the composition to a patient who had shown bleeding to prevent manifestation of bleeding symptoms in advance (prevention of bleeding), but it is not limited thereto. Treatment and prevention of bleeding may be understood as having the same meaning in certain cases and such treatment and prevention of bleeding may be called prophylaxis therapy or regular administration therapy of a therapeutic agent (the bispecific antigen-binding molecules of the present invention).

Prevention of hemophilia refers to, for example, reducing the incidence of hemophilia or reducing the likelihood of hemophilia.

Herein, bleeding that is examined and counted as the number of bleeding events in a patient is, for example, bleeding that required hemostatic treatment by coagulation factor formulations. Coagulation factor formulations refer to, for example, FVIII formulations and bypassing agents (activated prothrombin complex formulations, recombinant FVIIa formulations, and such).

The number of bleedings per year (the Annualized Bleeding Rate (ABR)) is calculated as, for example: (number of bleeding events×365.25)/number of days of observation.

The present invention provides a pharmaceutical composition comprising a bispecific antigen-binding molecule which recognizes (a) FIX and/or FIXa and (b) FX and/or FXa, as a more effective pharmaceutical composition for preventing and/or treating bleeding, a disease accompanying bleeding, or a disease caused by bleeding, the disease including those that develops and/or progresses due to a decrease or deficiency in the activity of FVIII and/or FVIIIa, or a dosage regimen thereof.

All prior art references cited herein are incorporated by reference into this description.

EXAMPLES

The present invention is specifically illustrated below with reference to Examples, but it is not construed as being limited thereto.

Example 1

Efficacious Dosing Regimens with Administration Interval Extension and/or Dose Up-Titration Dose-Exposure-Response Model Development A population pharmacokinetic (PopPK) model of emicizumab was developed using the quantifiable plasma emicizumab concentration data from 42 healthy subjects (NPL 8) and 18 patients with hemophilia A having or not having FVIII inhibitors (NPLs 9 and 10). In addition, the exposure-response relationship on the bleeding-prophylactic efficacy of emicizumab was quantitatively characterized based on a repeated time-to-event (RTTE) modeling approach using the bleeding onset data from the same 18 patients (NPLs 9 and 10).

A one-compartment model with first-order absorption and first-order elimination was employed as the structural PopPK model to describe the plasma emicizumab concentration-time profile. The parameter estimates of the PopPK model including covariate effects are listed in Table 1.

TABLE 1

Parameter Estimates of the Population Pharmacokinetic Model

| Parameter | Unit | Estimate[a] |
|---|---|---|
| Model structure | | |
| $CL/F^{b)}$ | L/day | 0.222 |
| $V_d/F^{b)}$ | L | 10.2 |
| $t_{1/2, abs}$ | day | 1.56 |
| Covariate effect | | |
| Onset time of the effect of influential ADA on CL/F after emicizumab administration | day | 33.4 |
| Effect of influential ADA on $CL/F^{c)}$ | — | 2.01 |
| Effect of BW on $CL/F^{d)}$ | — | 0.75 (fixed) |
| Effect of BW on $V_d/F^{d)}$ | — | 1 (fixed) |
| Effect of PAT on $CL/F^{c)}$ | — | 0.232 |
| Effect of PAT on $V_d/F^{c)}$ | — | 0.175 |
| Inter-individual variability[e] | | |
| Variance for CL/F | — | 0.0737 |
| Variance for $V_d/F$ | — | 0.0455 |
| Variance for $t_{1/2, abs}$ | — | 0.502 |
| Covariance for CL/F and $V_d/F$ | — | 0.0278 |
| Residual unexplained variability[f] | | |
| Additive error[g] | µg/mL | 0.0149 |
| Proportional error[h] | % | 12.8 |

CL/F: apparent total clearance,
$V_d/F$: apparent volume of distribution,
$t_{1/2, abs}$: first-order absorption half-life,
ADA: influential anti-drug antibodies,
BW: body weight,
PAT: patient.
[a] estimated using NONMEM software version 7.2.0 (ICON Development Solutions, Ellicott City, MD, USA),
[b] standardized by a typical body weight of 70 kg,
[c] parameterized as log-transformed geometric mean ratio,
[d] parameterized as allometric exponent (assumed to work in a power manner),
[e] assumed to follow an exponential error model,
[f] assumed to follow a combined additive plus proportional error model,
[g] parameterized as standard deviation,
[h] parameterized as coefficient of variation.

RTTE modeling dealt with the bleeding events that occurred both before (i.e., for approximately 6 months) and after the start of emicizumab administration and required the on-demand use of coagulation factor products, regardless of the bleeding site. A time-varying hazard model as the structural RTTE model consisted of a constant baseline hazard (lambda) to account for the bleeding rate when treated with the on-demand therapy with coagulation factor products and an $E_{max}$ model to account for the bleeding-prophylactic effect of emicizumab as a function of plasma emicizumab concentration. The model equation of the RTTE model is illustrated below, and the parameter estimates are listed in Table 2.

$$h(t) = \lambda \times \left(1 - \frac{\frac{C_p(t)}{EC_{50}} + E_{PLX}}{1 + \frac{C_p(t)}{EC_{50}} + E_{PLX}}\right) \quad \text{[Math. 1]}$$

$h(t)$: hazard on bleeding onset at a time of $t$, $C_p(t)$: population pharmacokinetic model-predicted plasma emicizumab concentration at a time of $t$, $\lambda$(lambda) : baseline hazard on bleeding onset (annual bleeding rate), $EC_{50}$: plasma emicizumab concentration to achieve a half of the maximum prophylactic effect on bleeding onset, $E_{PLX}$: effect of the prophylactic therapy with coagulation factor products when ongoing

TABLE 2

Parameter Estimates of the Repeated Time-to-Event Model

| Parameter | Unit | Estimate[a] |
|---|---|---|
| Model structure | | |
| λ (lambda) | count/year | 21.9 |
| $EC_{50}$ | μg/mL | 1.19 |
| $E_{PLX}$ | — | 0.314 |
| Inter-individual variability[b] | | |
| Variance for λ | — | 0.340 |
| Variance for $EC_{50}$ | — | 2.53 | lambda: baseline hazard on bleeding onset (annual bleeding rate),
$EC_{50}$: plasma emicizumab concentration to achieve a half of the maximum prophylactic effect on bleeding onset,
$E_{PLX}$: effect of the prophylactic therapy with coagulation factor products when ongoing.
[a]estimated using NONMEM software version 7.2.0 (ICON Development Solutions, Ellicott City, MD, USA),
[b]assumed to follow an exponential error model.

Determination of Efficacious Exposure and Justification of Dose Up-Titration

The RTTE model-simulated relationship between annual bleeding rate (ABR) and plasma emicizumab concentration is shown in FIG. 1. A plasma emicizumab concentration of 45 micro g/mL or more is expected to achieve a median ABR of zero indicating no bleeding onset for a year in 50% or more of patients.

Further improvement in bleeding-prophylactic efficacy outcome is not expected at plasma emicizumab concentrations of 45 micro g/mL or more in terms of median ABR. However, due to the inter-individual variability in drug effect and baseline ABR, there would remain considerable proportions of patients with ABR of >0 even at such plasma emicizumab concentrations. Therefore, it is likely that increasing plasma emicizumab concentration (emicizumab dose) results in further reduced ABR in patients with imperfect bleeding control. In addition, in case of a special population likely to exhibit lower exposure (e.g., pediatric patients), increasing emicizumab dose should make sense to provide increased plasma emicizumab concentration and accordingly further reduced ABR.

Determination of Efficacious Dose and Justification of Administration Interval Extension As doses to achieve the target exposure level of 45 micro g/mL, once-weekly loading dose of 3 mg/kg for the first 4 weeks followed by once-weekly maintenance dose of 1.5 mg/kg or once-every-two-week maintenance dose of 3 mg/kg were proposed. The repeated loading doses were intended to achieve the steady-state plasma concentration as early as possible. The PopPK model-simulated plasma emicizumab concentration-time profiles at the proposed dosing regimens are shown in FIG. 2 and FIG. 3. The simulations indicated that more than half of patients should achieve the target exposure level of 45 micro g/mL at steady state (i.e., after 4 weeks onwards) at both dosing regimens.

Another proposed dosing regimen of once-weekly loading dose of 3 mg/kg for the first 4 weeks followed by once-4-weekly maintenance dose of 6 mg/kg was not predicted to achieve the target exposure level of 45 micro g/mL as a median steady-state trough level, while providing a higher peak level due to a larger peak-trough fluctuation (FIG. 4). However, in terms of efficacy, the PopPK/RTTE model-simulated ABR distributions were predicted to be similar among the dosing regimens (FIG. 5, FIG. 6, and FIG. 7). This suggests that with a given dose per administration for maintenance dose which is higher than that for loading dose, extending the administration interval would result in a similar bleeding-prophylactic efficacy to other dosing regimens with a per-administration maintenance dose lower than or equal to the loading dose.

Example 2

A Randomized, Multi-Center, Open-Label Phase III Clinical Trial to Evaluate the Efficacy, Safety and Pharmacokinetics of Prophylactic Emicizumab Versus No Prophylaxis in Hemophilia A Patients with Inhibitors (HAVEN 1)

This multicenter, open-label study evaluated the safety, efficacy and pharmacokinetics of prophylactic emicizumab treatment or regular emicizumab administration therapy in patients previously treated with episodic or prophylactic bypassing agents. Episodic bypassing agent patients were randomized in a 2:1 fashion to receive emicizumab prophylaxis (Arm A) versus no prophylaxis (Arm B) and were stratified across Arms A and B according to the number of bleeds they had experienced over the last 24 weeks prior to study entry (less than [<] 9 or greater than or equal to [>=] 9 bleeds); Arm B patients had the opportunity to switch to emicizumab prophylaxis after 24 weeks on-study. Prophylactic bypassing agent patients switched to emicizumab prophylaxis (Arm C) from the start of the trial; enrollment was extended for 24 weeks after the last patient enrolled in Arms A or B or until approximately 50 patients enrolled in Arm C, whichever occurred first. Episodic or prophylactic bypassing agent patients who previously participated in a Non-Interventional Study (NIS) BH29768 but were unable to enroll in Arms A or B prior to their closure had the opportunity to enroll in Arm D until 24 weeks after the last patient enrolled in Arms A or B or until approximately 35 patients enrolled in Arm D, whichever occurred first. Like patients in Arms A and C, Arm D patients received emicizumab prophylaxis from the start of the trial. All patients continued to receive standard of care/background treatment with their usual episodic bypassing agent therapy to treat breakthrough bleeds, as needed.

Arm A: Episodic Treatment+Study Drug (Emicizumab Prophylaxis)

Patients with inhibitors (patients that meet the inclusion criteria of diagnosis of congenital hemophilia A of any severity and documented history of high-titer inhibitor (i.e., 5 or more Bethesda Units [BU])) who received episodic treatment with bypassing agents prior to study entry were randomized to receive emicizumab prophylaxis when they start the trial.

Arm B: Episodic Treatment (No Prophylaxis)

Patients with inhibitors who received episodic treatment with bypassing agents prior to study entry were randomized to continue episodic bypassing agent treatment when they start the trial; they had the opportunity to switch to emicizumab prophylaxis after 24 weeks on-study.

Arm C: Study Drug (Emicizumab Prophylaxis)+Episodic Treatment

Patients with inhibitors who received prophylactic treatment with bypassing agents prior to study entry received emicizumab prophylaxis when they start the trial.

Arm D: Study Drug (Emicizumab Prophylaxis)+Episodic Treatment

Episodic or prophylactic bypassing agent patients who previously participated in a Non-Interventional Study BH29768 but were unable to enroll in Arms A or B prior to their closure had the opportunity to enroll in Arm D, in which they received emicizumab prophylaxis when they started the trial.

Emicizumab was administered subcutaneously at a dose of 3 mg/kg/week for 4 weeks followed by 1.5 mg/kg/week up to the end of the study.

The primary endpoint was the reduction of frequency in bleeding for patients who received subcutaneously administered emicizumab at a dose of 3 mg/kg/week for 4 weeks followed by 1.5 mg/kg/week compared to patients without the drug. The number of bleeds was significantly reduced in patients with the drug as described in more detail below.

Study Population

One hundred and nine participants were enrolled. All participants were male and had a median age of 28 years (range, 12-75; Table 3); the median age in Arm C was lower, which was consistent with higher prior use of prophylactic BPAs in this younger group. While most had severe hemophilia, 7/109 participants had mild or moderate disease. Approximately 40% of participants in Arms A, B, and D received prior immune tolerance induction (ITI), while 67% of participants in Arm C previously underwent ITI. The majority of participants (69.7%) had target joints, with 69.7% having >1 target joint. Median (range) emicizumab treatment exposure was 24.0 weeks (3.0-47.9) overall. Median (range) duration of emicizumab treatment exposure were Arm A, 29.5 (3.3-47.9) weeks; Arm B, 8.0 (4.0-16.0) weeks; Arm C, 19.0 (5.9 45.0) weeks and Arm D, 5.8 (3.0-14.0) weeks.

TABLE 3

Participant demographics and baseline characteristics

| | Study arm | | | | |
|---|---|---|---|---|---|
| | A: Emicizumab prophylaxis (N = 35) | B: No prophylaxis (N = 18) | C: Emicizumab prophylaxis (N = 49) | D: Emicizumab prophylaxis (N = 7) | Total (N = 109) |
| Sex, n (%) | | | | | |
| Male | 35 (100) | 18 (100) | 49 (100) | 7 (100) | 109 (100) |
| Age, years | | | | | |
| Median (min-max) | 38.0 (12-68) | 35.5 (13-65) | 17.0 (12-75) | 26.0 (19-49) | 28.0 (12-75) |
| Age, n (%) | | | | | |
| <18 years | 4 (11.4) | 2 (11.1) | 26 (53.1) | 0 (0) | 32 (29.4) |
| ≥18 years | 31 (88.6) | 16 (88.9) | 23 (46.9) | 7 (100) | 77 (70.6) |
| Hemophilia severity at baseline, n (%) | | | | | |
| Mild | 2 (5.7) | 0 (0) | 1 (2.0) | 0 (0) | 3 (2.8) |
| Moderate | 2 (5.7) | 0 (0) | 1 (2.0) | 1 (14.3) | 4 (3.7) |
| Severe | 31 (88.6) | 18 (100) | 47 (95.9) | 6 (85.7) | 102 (93.6) |
| Bleeding events in 24 weeks prior to study entry, n (%) | | | | | |
| <9 | 11 (31.4) | 5 (27.8) | 23 (46.9) | 4 (57.1) | 43 (39.4) |
| ≥9 | 24 (68.6) | 13 (72.2) | 26 (53.1) | 3 (42.9) | 66 (60.6) |
| Target joints,* n (%) | | | | | |
| No | 10 (28.6) | 5 (27.8) | 15 (30.6) | 3 (42.9) | 33 (30.3) |
| Yes | 25 (71.4) | 13 (72.2) | 34 (69.4) | 4 (57.1) | 76 (69.7) |
| 1 | 7 (28.0) | 3 (23.1) | 10 (29.4) | 3 (75.0) | 23 (30.3) |
| >1 | 18 (72.0) | 10 (76.9) | 24 (70.6) | 1 (25.0) | 53 (69.7) |
| Highest historical inhibitor titer (BU) | | | | | |
| n | 32 | 16 | 47 | 6 | 101 |
| Mean (SD) | 288.9 (472.8) | 706.8 (1450.0) | 815.7 (1148.1) | 528.9 (793.4) | 614.5 (1037.9) |
| Median | 84.5 | 102.0 | 309.0 | 240.0 | 180.0 |
| Min-Max | 5-1570 | 18-4500 | 11-5000 | 28-2125 | 5-5000 |
| <5 BU, n/N (%) | 0/35 (0) | 0/18 (0) | 0/49 (0) | 0/7 (0) | 0/109 (0) |

TABLE 3-continued

Participant demographics and baseline characteristics

| | Study arm | | | | |
|---|---|---|---|---|---|
| | A: Emicizumab prophylaxis (N = 35) | B: No prophylaxis (N = 18) | C: Emicizumab prophylaxis (N = 49) | D: Emicizumab prophylaxis (N = 7) | Total (N = 109) |
| ≥5 BU, n/N (%) | 32/35 (91.4) | 16/18 (88.9) | 47/49 (95.9) | 6/7 (85.7) | 101/109 (92.7) |
| Unknown, n/N (%) | 3/35 (8.6) | 2/18 (11.1) | 2/49 (4.1) | 1/7 (14.3) | 8/109 (7.3) |
| Episodic coagulation product use in 24 weeks prior to study entry, n (%) | | | | | |
| Any products | 35 (100) | 18 (100) | 23 (47) | 7 (100) | 83 (76) |
| aPCC | 27 (77.1) | 13 (72.2) | 15 (65.2) | 5 (71.4) | 60 (72.3) |
| rFVIIa | 22 (62.9) | 17 (94.4) | 15 (65.2) | 5 (71.4) | 59 (71.1) |
| Factor VIII | 1 (2.9) | 0 (0) | 1 (4.3) | 2 (28.6) | 4 (4.8) |
| Other | 1 (2.9) | 0 (0) | 0 (0) | 1 (14.3) | 2 (2.4) |
| Prophylactic coagulation product use in 24 weeks prior to study entry, n (%) | | | | | |
| Any products | 0 (0) | 0 (0) | 49 (100) | 0 (0) | 49 (45) |
| aPCC | 0 (0) | 0 (0) | 36 (73.5) | 0 (0) | 36 (73.5) |
| rFVIIa | 0 (0) | 0 (0) | 15 (30.6) | 0 (0) | 15 (30.6) |
| Factor VIII | 0 (0) | 0 (0) | 1 (2.0) | 0 (0) | 1 (2.0) |
| Other | 0 (0) | 0 (0) | 1 (2.0) | 0 (0) | 1 (2.0) |

*% based on number of participants with target joints, all numbers are based on eCRF and not NIS data.
aPCC, activated prothrombin complex concentrates;
NIS, non-interventional study;
rFVIIa, recombinant factor VIIa.

Efficacy

There was a statistically significant and clinically meaningful 87% reduction in bleed rates between Arms A (emicizumab prophylaxis) versus B (no prophylaxis); ABR (95% CI) 2.9 (1.69; 5.02) versus 23.3 (12.33; 43.89), p<0.0001 (FIG. 8 and Table 4). Statistically significant and clinically meaningful reductions were also observed in all secondary bleed-related endpoints, including spontaneous, joint, and target joint bleeds, and all bleeds. Overall, 62.9% (22/35) of participants randomized to emicizumab prophylaxis experienced zero bleeds (FIG. 8 and Table 4).

TABLE 4

Bleeds across study arms

| | Study arms | | |
|---|---|---|---|
| Bleeds | A: Emicizumab prophylaxis (N = 35) | B: No prophylaxis (N = 18) | C: Emicizumab prophylaxis (N = 49) |
| Treated bleeds (with BPAs) | | | |
| ABR, model based$^a$ (95% CI) | 2.9 (1.69; 5.02) | 23.3 (12.33; 43.89) | 5.1 (2.28; 11.22) |
| % reduction (RR), p value | 87% (0.13), p < 0.0001 | | — |
| Median ABR, calculated (IQR) | 0.0 (0.0; 3.7) | 18.8 (13.0; 35.1) | 0.0 (0.0; 1.7) |
| All bleeds (treated/not treated with BPAs) | | | |
| ABR, model based$^a$ (95% CI) | 5.5 (3.58; 8.60) | 28.3 (16.79; 47.76) | 6.5 (3.43; 12.43) |
| % reduction (RR), p value | 80% (0.20), p < 0.0001 | | — |
| Median ABR, calculated (IQR) | 2.0 (0.0; 9.9) | 30.2 (18.3; 39.4) | 0.0 (0.0; 6.0) |
| Treated spontaneous bleeds | | | |
| ABR, model based$^a$ (95% CI) | 1.3 (0.73; 2.19) | 16.8 (9.94; 28.30) | 3.1 (1.20; 8.02) |
| % reduction (RR), p value | 92% (0.08), p < 0.0001 | | — |
| Median ABR, calculated (IQR) | 0.0 (0.0; 3.3) | 15.2 (6.6; 30.4) | 0.0 (0.0; 0.0) |
| Treated joint bleeds | | | |
| ABR, model based$^a$ (95% CI) | 0.8 (0.26; 2.20) | 6.7 (1.99; 22.42) | 0.6 (0.21; 1.48) |
| % reduction (RR), p value | 89% (0.11), 0.0050 | | — |
| Median ABR, calculated (IQR) | 0.0 (0.0; 0.0) | 1.0 (0.0; 14.4) | 0.0 (0.0; 0.0) |
| Treated target joint bleeds | | | |
| ABR, model based$^a$ (95% CI) | 0.1 (0.03; 0.58) | 3.0 (0.96; 9.13) | 0.3 (0.10; 0.95) |
| % reduction (RR), p value | 95% (0.05), 0.0002 | | — |

TABLE 4-continued

Bleeds across study arms

| Bleeds | Study arms | | |
|---|---|---|---|
| | A: Emicizumab prophylaxis (N = 35) | B: No prophylaxis (N = 18) | C: Emicizumab prophylaxis (N = 49) |
| Median ABR, calculated (IQR) | 0.0 (0.0; 0.0) | 1.0 (0.0; 6.5) | 0.0 (0.0; 0.0) |
| Participants with zero bleeds, % (95% CI) | 62.9 (44.9; 78.5) | 5.6 (0.1; 27.3) | 69.4 (54.6; 81.7) |

[a]Negative binomial model.
ABR, annualized bleeding rate;
BPA, bypassing agent;
CI, confidence interval;
IQR, interquartile range;
RR, relative risk The intra-participant comparison in those who had previously participated in the NIS showed that emicizumab prophylaxis significantly reduced bleed rate versus previous BPA prophylaxis (79%: RR 0.21; p=0.0003 [Arm C]); individual participant data are shown in FIG. 9 and corresponding data for the intra-participant comparison versus prior episodic BPAs (Arm A) are shown in FIG. 11. Intra-participant comparison for emicizumab prophylaxis versus prior episodic BPA treatment showed a significant reduction in the risk of treated bleeds (92%: RR 0.08; p<0.0001 [Arm A]).

Emicizumab prophylaxis was associated with statistically significant and clinically meaningful improvements in health-related quality of life (HRQoL) and health status compared with no prophylaxis. Differences in adjusted means observed in study and clinically important differences determined from published literature (Wyrwich et al. Interpreting important health-related quality of life change using the Haem-A-QoL. Haemophilia. 2015; 21(5):578-584; Walters and Brazier. Comparison of the minimally important difference for two health state utility measures: EQ-5D and SF-6D. Qual Life Res. 2005; 14(6):1523-1532; Pickard et al. Estimation of minimally important differences in EQ-5D utility and VAS scores in cancer. Health Qual Life Outcomes. 2007; 5:70), respectively, were as follows: Haem-A-QoL physical health subscale, 21.55 (p=0.0029) and 10 points; Haem-A-QoL total score, 14.01 (p=0.0019) and 7 points; EQ-5D-5L VAS, −9.72 (p=0.0171) and 7 points; and, EQ-5D-5L Index utility score, −0.16 (p=0.0014) and 0.07 points.

Pharmacokinetic and Pharmacodynamic Outcomes

Mean trough emicizumab concentrations of >50 micro g/mL in blood were achieved after 4 weeks with administrations of the loading dose of 3 mg/kg/week, and sustained over the course of the study with administrations of the maintenance dose of 1.5 mg/kg/week (FIG. 10). D-dimer and prothrombin fragment 1.2 were not affected by emicizumab treatment.

Example 3

Efficacy, Safety and Pharmacokinetics (PK) of Once-Weekly Prophylactic (Px) Emicizumab (ACE910) in Pediatric (<12 Years) Persons with Hemophilia A with Inhibitors (PwHAwI): Interim Analysis of Single-Arm, Multicenter, Open-Label, Phase 3 Study (HAVEN 2)

The study enrolled PwHAwI aged <12 years (or 12-17 years if <40 kg) previously treated with bypassing agents (BPAs) to receive emicizumab prophylaxis for 52 or more weeks. Efficacy objectives included annualized bleeding rate (ABR) and bleed reduction versus historical bleed rate (non-interventional study).

Participants received weekly subcutaneous (SC) administrations of emicizumab for a designated period of 52 weeks. All participants continued to receive standard of care/background treatment with their usual episodic bypassing agent therapy to treat breakthrough bleeds as needed.

Emicizumab was administered SC once weekly for 52 weeks, 3 milligrams per kilogram per week (mg/kg/week) for 4 weeks and 1.5 mg/kg/week thereafter. The regimen was to be adapted based upon efficacy/bleed control.

Interim analysis included 20 PwHAwI aged 3-12 years (median 8.5); 19 aged <12 years were included in the efficacy analyses (Table 5). The median observation time was 12.1 weeks (range 7.1-14.1). In total, 18/19 (94.7%) PwHAwI had zero treated bleeds and 12/19 (63.2%) did not bleed while on study. Overall, 14 bleeds were reported in 7 PwHAwI; with none occurring in a joint or muscle. A substantial reduction in ABR on study versus ABR from the NIS was observed in 8 PwHAwI included in the intra-participant comparison (FIG. 12); 8/8 had 100% reduction in number of treated bleeds, 5/8 had 100% reduction in number of all bleeds, and all PwHAwI had >75% reduction of all bleeds. Mean trough emicizumab concentrations of >50 micro g/mL were achieved after 4 weeks and sustained.

Emicizumab Px (prophylaxis) was safe and prevented/reduced bleeds in pediatric PwHAwI, showing clinically meaningful reductions in ABR compared with historical ABR. PK was similar to that seen in adult PwHA (persons with hemophilia A). These interim data show the potential for emicizumab to reduce the treatment and disease burden for pediatric PwHAwI.

TABLE 5

Bleeding events in HAVEN 2 study

| Bleeds[a] | Mean ABR[b] (95% CI) N= 10 | % PwHAwI with zero bleeds (95% CI) N = 19 |
|---|---|---|
| Treated bleeds | 0.4 (0.00; 4.51) | 94.7 (74.0, 99.9) |
| All bleeds | 3.7 (0.94; 9.81) | 63.2 (38.4; 83.7) |
| Treated spontaneous bleeds | 0.4 (0.00; 4.51) | 94.7 (74.0; 99.9) |

[a]Bleed/medication questionnaire completed by caregiver via an electronic handheld device. Bleed definitions based on ISTH criteria (Blanchette V S, et al. J Thromb Haemost 2014; 12: 1935-39). Treated bleeds: bleeds treated with BPAs. All bleeds: bleeds treated and not treated with BPAs.
[b]ABR calculated for persons on HAVEN 2 study 12 or more weeks.

Example 4

A Randomized, Multi-Center, Open-Label, Phase 3 Clinical Study in Participants Aged 12 Years or Older to Evaluate the Efficacy, Safety, and Pharmacokinetics of Prophylactic Emicizumab Versus No Prophylaxis in Participants with Severe Hemophilia A without Inhibitors Against FVIII (HAVEN 3)

This is a randomized, multicenter, open-label, Phase 3 clinical study in participants aged 12 years or older to evaluate the efficacy, safety, and pharmacokinetics of prophylactic emicizumab versus no prophylaxis in participants with severe hemophilia A without inhibitors against FVIII (HAVEN 3).

Participants received emicizumab prophylaxis at the specified dose subcutaneously until the end of the study (maximum up to 2 years).

Experimental: Emicizumab (Pre-Study FVIII Prophylaxis)

Participants who received FVIII prophylaxis prior to study entry received emicizumab prophylaxis at a dose of 3 mg/kg/week subcutaneously for 4 weeks, followed by 1.5 milligram per kilogram per week (mg/kg/week) emicizumab subcutaneously until the end of study (maximum up to 2 years).

Experimental: Emicizumab 1.5 mg/kg/Week

Participants who received episodic treatment with FVIII prior to study entry received emicizumab prophylaxis at a dose of 3 mg/kg/week subcutaneously for 4 weeks, followed by 1.5 mg/kg/week emicizumab subcutaneously until the end of study (maximum up to 2 years).

Experimental: Emicizumab 3 mg/kg/2 Weeks

Participants who received episodic treatment with FVIII prior to study entry received emicizumab prophylaxis at a dose of 3 mg/kg/week subcutaneously for 4 weeks, followed by 3 mg/kg once every 2 weeks (3 mg/kg/2 weeks) emicizumab subcutaneously until the end of study (maximum up to 2 years).

Active Comparator: No Prophylaxis

Participants who received episodic treatment with FVIII prior to study entry were randomized to continue episodic FVIII treatment when they started the trial; they had the opportunity to switch to emicizumab prophylaxis after 24 weeks on-study.

Primary Outcome Measures:
Number of bleeds over time
Secondary Outcome Measures:
Reduction in number of bleeds over time [Time Frame: Baseline, 24 weeks]
Reduction in number of joint bleeds over time [Time Frame: Baseline, 24 weeks]
Reduction in number of target joint bleeds over time [Time Frame: Baseline, 24 weeks]
Health related quality of life scores [Time Frame: 24 weeks]
Trough plasma concentration ($C_{trough}$) of emicizumab [Time Frame: (Pre-dose) Every week during Weeks 1-4, every 2 weeks during Weeks 5-8, every 4 weeks during Weeks 9-24, every 8 weeks during Weeks 25-48, every 12 weeks thereafter (maximum up to 2 years)]

Example 5

A Multicenter, Open-Label, Non-Randomized Study to Assess the Efficacy, Safety, Pharmacokinetics, and Pharmacodynamics of Emicizumab Administered at a Dose of 6 Milligrams Per Kilogram (Mg/Kg) Every 4 Weeks in Participants with Hemophilia A with or without Inhibitors Against FVIII (HAVEN 4)

This multicenter, open-label, non-randomized study has assessed the efficacy, safety, pharmacokinetics, and pharmacodynamics of emicizumab administered at a dose of 6 milligrams per kilogram (mg/kg) once every 4 weeks (Q4W) in participants with hemophilia A with or without inhibitors against factor VIII (FVIII). The study consisted of 2 parts: a pharmacokinetic (PK) run-in part followed by an expansion part.

Emicizumab was administered according to the dose and schedule described in respective arms.

Experimental: Emicizumab: Expansion Part

Participants received emicizumab at a loading dose of 3 mg/kg once every week subcutaneously for initial 4 weeks followed by a maintenance dose of 6 mg/kg once every 4 weeks subcutaneously for a minimum of 24 weeks.

Experimental: Emicizumab: PK Run-in Part

Participants received emicizumab at a dose of 6 mg/kg once every 4 weeks subcutaneously for a minimum of 24 weeks.

Primary Outcome Measures:

Expansion Part: Number of Bleeding Events Over Time [Time Frame: Expansion Part: Day 1 up to study completion (a minimum of 24 weeks, up to approximately 20 months)]

At the data cutoff of Apr. 10, 2017, 7 patients with severe hemophilia A had enrolled into the PK run-in cohort, 4 patients without inhibitors and 3 patients with inhibitors, of which 6 patients were aged 18 and over, and followed for a minimum of 6 weeks. Individual observed PK profiles were within the 95% prediction interval computed from a population PK model based on clinical data from a 1.5 mg/kg QW regimen (FIG. 13: gray bold solid lines indicate the upper and lower limits of the 95% prediction interval). Emicizumab PK parameters derived after a single SC administration of 6 mg/kg emicizumab (Table 6) were consistent with the values observed in previous studies with emicizumab (Uchida et al. Blood 2016; 127 (13):1633-1641). During the observation period (median, 8 weeks), 14 adverse events (AEs) were reported in 5 patients at the time of data cut-off, including 1 Grade 3 serious AE (worsening of hypertension); no AEs were considered related to the study drug. No anti-drug antibodies were detected. Also, 6 out of 7 patients had no bleeds while receiving Q4W emicizumab; 1 patient experienced 3 spontaneous nose bleeds on Study Days 12, 14, and 21, which did not require treatment.

TABLE 6

Summary of PK parameters after single SC dose of 6 mg/kg emicizumab

| | $T_{max}$ (day) | $C_{max}$ (µg/mL) | $AUC_{Day\ 28}$ (day*µg/mL) | $T_{1/2}$ (day) |
|---|---|---|---|---|
| Value* | 6.95 (3.99-7.18) | 31.8 (19.3) | 662.5 (19.7) | 30.2 (35.8) |

*Median (range) for $T_{max}$ and geometric mean (CV %) for all other parameters.

Preliminary data from the HAVEN 4 study showed that Q4W dosing of emicizumab at 6 mg/kg per administration exhibited a PK behavior that was consistent with prior predictions, leading to an expected steady-state concentration average similar to the clinically confirmed dosing regimen (i.e., 1.5 mg/kg/QW). The safety and efficacy results from this PK run-in cohort enabled the opening of the HAVEN 4 expansion cohort, and provided promising support for a Q4W emicizumab prophylaxis regimen for the management of hemophilia A. The HAVEN 4 study is fully enrolled (N=48, including the PK run-in cohort patients).

Example 6

A Multicenter, Open-Label, Phase III Clinical Trial to Evaluate the Efficacy, Safety, and Pharmacokinetics of Subcutaneous Administration of Emicizumab in Hemophilia A Pediatric Patients with Inhibitors The study protocol of HAVEN 2 (see Example 3) has been amended to evaluate additional two emicizumab dosing schedules (once every 2 weeks [Q2W] and once every 4 weeks [Q4W]) as well as the originally planned dosing schedule (once weekly [QW]).

Overall, this non-randomized, multicenter, open-label, Phase III clinical study enrolls children with hemophilia A who have inhibitors against FVIII. Children with hemophilia A and documented historical FVIII inhibitor titer (5 BU or more) must currently be receiving treatment with bypassing agents. The study enrolls at least 40 patients younger than 12 years of age and up to approximately 80 patients, with allowance of patients of 12 to 17 years of age who weigh less than 40 kg at the time of informed consent.

Patients enrolled in Cohort A receive emicizumab administration, with a loading dose of 3 mg/kg per administration once weekly (QW) for the first 4 weeks and a maintenance dose of 1.5 mg/kg per administration QW thereafter for a minimum of 52 weeks in total. Patients enrolled in Cohorts B and C receive emicizumab administration, with the same loading dose of 3 mg/kg QW for the first 4 weeks and a maintenance dose of 3 mg/kg Q2W (Cohort B) or 6 mg/kg Q4W (Cohort C) thereafter for a minimum of 52 weeks in total. During the 52-week treatment period, individual patients may have their dose up-titrated if they experience suboptimal bleeding control with emicizumab.

The efficacy analyses evaluate the clinical effect of prophylactic emicizumab on the number of bleeds over time (i.e., bleed rate), and characterize the efficacy of up-titration on an intra-patient level. Bleeds having different bleed definitions such as treated bleeds, all bleeds, treated spontaneous bleeds, treated joint bleeds, and treated target joint bleeds are analyzed separately. The primary analysis is performed 52 weeks after the last patient in the primary cohort, which consists of all patients enrolled in Cohort A prior to the close of enrollment for patients 2 years of age or older, has been enrolled or withdrawn prematurely, whichever occurs first. No formal hypothesis testing is planned in the study.

Results from an interim analysis in Cohort A are presented in Example 3.

Example 7

A Multicenter, Open-Label, Phase III Study Evaluating the Efficacy, Safety, and Pharmacokinetics of Emicizumab Administered Every 2 or 4 Weeks in Pediatric Patients Less than 12 Years Old with Hemophilia A without Factor VIII Inhibitors This study is a multicenter, open-label, non-randomized study designed to evaluate the efficacy, safety, and pharmacokinetics of emicizumab administered subcutaneously at a dose of 3 mg/kg per administration once every 2 weeks (Q2W cohort) or 6 mg/kg per administration once every 4 weeks (Q4W cohort) in pediatric patients with hemophilia A without inhibitors. The study enrolls a minimum of 6 patients less than 12 years old with hemophilia A without inhibitors in each cohort.

The Q2W cohort of the study receives a loading dose of 3 mg/kg of emicizumab administered subcutaneously once weekly (QW) for the first 4 doses, followed by a maintenance dose of 3 mg/kg administered subcutaneously once every 2 weeks (Q2W) for at least 24 weeks in total. The Q4W cohort receives a loading dose of 3 mg/kg of emicizumab administered subcutaneously once weekly (QW) for the first 4 doses, followed by a maintenance dose of 6 mg/kg administered subcutaneously once every 4 weeks (Q4W) for at least 24 weeks in total. After Week 12 of emicizumab treatment, a higher dose may be selected for patients who meet the insufficient bleeding control criteria.

The efficacy analyses evaluate the clinical effects of emicizumab prophylaxis based on the bleeding frequency (bleeding rate) during a specified period. Bleeds having various different definitions such as bleeds requiring use of coagulation factors for hemostasis, spontaneous bleeds, joint bleeds, target joint bleeds, and all bleeds are analyzed separately. The primary efficacy analysis is conducted in each cohort when all patients have completed the 24-week treatment or have been withdrawn from the study, whichever occurs first. No statistical hypothesis testing is planned.

The invention claimed is:

1. A method for treating or reducing the incidence of a disease in a subject, wherein the disease is selected from the group consisting of hemophilia A, acquired hemophilia A, von Willebrand disease, and hemophilia A with emergence of an inhibitor against blood coagulation factor VIII and/or activated blood coagulation factor VIII,
   the method comprising administering to the subject a bispecific antibody in a loading dose of 3 mg/kg administered once every week for four weeks, and thereafter administering to the subject a maintenance regimen comprising one or more maintenance doses of the antibody,
   wherein the amount of antibody in each maintenance dose totals 6 mg/kg over the course of a four week period,
   wherein each maintenance dose is given as a single administration once every four week period or is divided into two or more administrations spaced out over each four week period,
   wherein the antibody recognizes (a) blood coagulation factor IX and/or activated blood coagulation factor IX and (b) blood coagulation factor X and/or activated blood coagulation factor X, and
   wherein the antibody comprises a first polypeptide that is an antibody heavy (H) chain comprising an H chain variable region comprising complementarity determining regions (CDRs) 1, 2, and 3 comprising the amino acid sequences set forth in SEQ ID NOs: 1, 2, and 3, respectively; a second polypeptide that is an antibody H chain comprising an H chain variable region comprising CDRs 1, 2, and 3 comprising the amino acid sequences set forth in SEQ ID NOs: 6, 7, and 8, respectively; and a third and a fourth polypeptide that are identical antibody light (L) chains comprising an L chain variable region comprising CDRs 1, 2, and 3 comprising the amino acid sequences set forth in SEQ ID NOs: 11, 12, and 13, respectively.

2. The method of claim 1, wherein the H chain variable region of the first polypeptide comprises the amino acid sequence set forth in SEQ ID NO: 4; the H chain variable region of the second polypeptide comprises the amino acid sequence set forth in SEQ ID NO: 9; and the L chain variable region comprises the amino acid sequence set forth in SEQ ID NO: 14.

3. The method of claim 1, wherein the first polypeptide comprises the amino acid sequence set forth in SEQ ID NO: 5; the second polypeptide comprises the amino acid sequence set forth in SEQ ID NO: 10; and the third and fourth polypeptides both comprise the amino acid sequence set forth in SEQ ID NO: 15.

4. The method of claim 1, wherein the antibody is emicizumab.

5. The method of claim 1, wherein each 6 mg/kg maintenance dose of the antibody is administered once every four weeks.

6. The method of claim 1, wherein each 6 mg/kg maintenance dose of the antibody is divided into two biweekly administrations of 3 mg/kg each.

7. The method of claim 1, wherein each 6 mg/kg maintenance dose of the antibody is divided into four weekly administrations of 1.5 mg/kg each.

8. The method of claim 1, wherein the maintenance doses are administered to the subject over multiple four-week periods.

9. The method of claim 1, wherein the disease is hemophilia A.

10. The method of claim 1, wherein the disease is acquired hemophilia A.

11. The method of claim 1, wherein the disease is von Willebrand disease.

12. The method of claim 1, wherein the disease is hemophilia A with emergence of an inhibitor against blood coagulation factor VIII and/or activated blood coagulation factor VIII.

13. The method of claim 1, wherein the maintenance doses are administered until at least 52 weeks have elapsed after the first loading dose was administered.

\* \* \* \* \*